(12) United States Patent
Li et al.

(10) Patent No.: US 7,307,080 B2
(45) Date of Patent: *Dec. 11, 2007

(54) COMPOUNDS, METHODS AND PHARMACEUTICAL COMPOSITIONS FOR TREATING CELLULAR DAMAGE, SUCH AS NEURAL OR CARDIOVASCULAR TISSUE DAMAGE

(75) Inventors: Jia-He Li, Cockeysville, MD (US); Jie Zhang, Ellicott City, MD (US)

(73) Assignee: MGI GP, Inc., Baltimore, MD (US)

( * ) Notice: Subject to any disclaimer, the term of this patent is extended or adjusted under 35 U.S.C. 154(b) by 511 days.

This patent is subject to a terminal disclaimer.

(21) Appl. No.: 10/772,235

(22) Filed: Feb. 6, 2004

(65) Prior Publication Data

US 2005/0074470 A1    Apr. 7, 2005

Related U.S. Application Data

(62) Division of application No. 09/781,195, filed on Feb. 13, 2001, now Pat. No. 6,716,828, which is a division of application No. 09/387,767, filed on Sep. 1, 1999, now Pat. No. 6,291,425.

(51) Int. Cl.
*A01N 43/58* (2006.01)
*A01N 43/60* (2006.01)
*A61K 31/50* (2006.01)
*A61K 31/495* (2006.01)
*C07D 251/00* (2006.01)

(52) U.S. Cl. .............. 514/248; 514/285; 514/410; 544/233; 546/70; 548/421

(58) Field of Classification Search .............. None
See application file for complete search history.

(56) References Cited

U.S. PATENT DOCUMENTS

| | | |
|---|---|---|
| 932,290 A | 8/1909 | Kacer et al. |
| 1,001,325 A | 8/1911 | Ullman et al. |
| 1,253,252 A | 1/1918 | Kardos et al. |
| 1,880,441 A | 10/1932 | Heidenreich et al. |
| 1,895,105 A | 1/1933 | Rath et al. |
| 2,467,692 A | 4/1949 | Petrow et al. |
| 2,593,798 A | 4/1952 | Robinson |
| 2,612,503 A | 9/1952 | Ullyot |
| 2,638,472 A | 5/1953 | Grewe |
| 2,666,059 A | 1/1954 | Davis et al. |
| 2,700,040 A | 1/1955 | Ullyot |
| 2,892,841 A | 6/1959 | Rudner |
| 2,992,220 A | 7/1961 | Irving et al. |
| 3,247,212 A | 4/1966 | Johnson |
| 3,291,801 A | 12/1966 | Montgomery |
| 3,300,499 A | 1/1967 | Lesher et al. |
| 3,403,157 A | 9/1968 | Humber et al. |
| 3,507,872 A | 4/1970 | Hegar |
| 3,534,038 A | 10/1970 | Machatzke et al. |
| 3,557,119 A | 1/1971 | Humber et al. |
| 3,573,304 A | 3/1971 | Eberle et al. |
| 3,700,673 A | 10/1972 | Watson, Jr. |
| 3,719,684 A | 3/1973 | Unger et al. |
| 3,723,436 A | 3/1973 | Hollstein et al. |
| 3,759,924 A | 9/1973 | Jeanmart et al. |
| 3,830,816 A | 8/1974 | Gittos et al. |
| 3,838,134 A | 9/1974 | Glauthier |
| 3,899,529 A | 8/1975 | Witzel |
| 3,900,477 A | 8/1975 | Philipp et al. |
| 3,904,671 A | 9/1975 | Minatoya |
| 3,932,643 A | 1/1976 | Gauthier |
| 3,950,343 A | 4/1976 | Philipp et al. |
| 3,978,066 A | 8/1976 | Philipp et al. |
| 3,991,064 A | 11/1976 | Brown et al. |
| 4,031,097 A | 6/1977 | Bach et al. |
| 4,082,741 A | 4/1978 | Hunger et al. |
| 4,169,897 A | 10/1979 | Meyer et al. |
| 4,218,453 A | 8/1980 | Hannart |
| 4,309,543 A | 1/1982 | Keeley |
| 4,382,943 A | 5/1983 | Winter et al. |
| RE31,617 E | 6/1984 | Beverung, Jr. et al. |
| 4,472,401 A | 9/1984 | Kennewell et al. |
| 4,594,415 A | 6/1986 | Robins et al. |
| 4,639,454 A | 1/1987 | Hesson |
| 4,740,581 A | 4/1988 | Pruett et al. |
| 4,742,171 A | 5/1988 | Martin et al. |
| 4,902,695 A | 2/1990 | Ornstein |
| 4,902,798 A | 2/1990 | Nakamatsu et al. |
| 4,925,968 A | 5/1990 | Sestanj et al. |
| 5,032,617 A | 7/1991 | Lee et al. |
| 5,041,653 A | 8/1991 | Lee et al. |
| 5,077,035 A | 12/1991 | Wieland et al. |
| 5,177,075 A | 1/1993 | Suto et al. |

| | | | | | | |
|---|---|---|---|---|---|---|
| 5,215,738 A | 6/1993 | Lee et al. | | GB | 810108 | 3/1959 |
| 5,262,564 A | 11/1993 | Kun et al. | | GB | 838994 | 6/1960 |
| 5,274,097 A | 12/1993 | Schohe et al. | | GB | 1263044 | 2/1972 |
| 5,338,851 A | 8/1994 | Huff et al. | | GB | 1379111 | 1/1975 |
| 5,391,376 A | 2/1995 | Long, Jr. et al. | | GB | 1474775 | 5/1977 |
| 5,391,554 A | 2/1995 | Showalter | | GB | 1545767 | 5/1979 |
| 5,395,835 A | 3/1995 | Glase et al. | | JP | 3-205402 | 9/1991 |
| 5,414,001 A | 5/1995 | Ireland et al. | | JP | 032 05402 A2 | 9/1991 |
| 5,420,136 A | 5/1995 | Lewis et al. | | JP | 042 75296 A2 | 9/1991 |
| 5,434,188 A | 7/1995 | Boschelli et al. | | JP | 4-13684 | 1/1992 |
| 5,464,871 A | 11/1995 | Kun et al. | | JP | 040 13684 A2 | 1/1992 |
| 5,473,074 A | 12/1995 | Kun et al. | | JP | 4-275223 | 9/1992 |
| 5,480,631 A | 1/1996 | De Paulis et al. | | JP | 4-275296 | 9/1992 |
| 5,482,975 A | 1/1996 | Kun et al. | | JP | 042 75223 A2 | 9/1992 |
| 5,516,941 A | 5/1996 | Kun et al. | | WO | WO 90/07502 | 7/1990 |
| 5,587,384 A | 12/1996 | Zhang et al. | | WO | WO 92/00281 | 1/1992 |
| 5,589,483 A | 12/1996 | West | | WO | WO 92/05770 | 4/1992 |
| 5,618,813 A | 4/1997 | Chu et al. | | WO | WO 92/15286 | 9/1992 |
| 5,633,282 A | 5/1997 | Collins et al. | | WO | WO 93/05096 | 3/1993 |
| 5,635,506 A | 6/1997 | Alberts et al. | | WO | WO 93/18748 | 9/1993 |
| 5,652,260 A | 7/1997 | Kun et al. | | WO | WO 95/04720 | 2/1995 |
| 5,652,367 A | 7/1997 | Kun et al. | | WO | WO 95/24379 | 9/1995 |
| 5,656,638 A | 8/1997 | Gaeta et al. | | WO | WO 95/29895 | 11/1995 |
| 5,659,082 A | 8/1997 | Flitter et al. | | WO | WO 95/30409 | 11/1995 |
| 5,665,710 A | 9/1997 | Rahman et al. | | WO | WO 96/28167 | 9/1996 |
| 5,670,518 A | 9/1997 | Kun et al. | | WO | WO 96/33268 | 10/1996 |
| 5,703,089 A | 12/1997 | Brana et al. | | WO | WO 97/30054 | 8/1997 |
| 5,703,116 A | 12/1997 | Gaeta et al. | | WO | WO 97/38977 | 10/1997 |
| 5,719,151 A | 2/1998 | Shall et al. | | WO | WO 98/27975 | 7/1998 |
| 5,753,674 A | 5/1998 | Kun et al. | | WO | WO 99/59975 | 1/1999 |
| 5,756,510 A | 5/1998 | Griffin et al. | | WO | WO 99/11622 | 3/1999 |
| 5,760,062 A | 6/1998 | Gaeta et al. | | WO | WO 99/11623 | 3/1999 |
| 5,767,135 A | 6/1998 | Fernandez-Pol | | WO | WO 99/11624 | 3/1999 |
| RE36,397 E | 11/1999 | Zhang et al. | | WO | WO 99/11628 | 3/1999 |
| 6,121,278 A | 9/2000 | Jackson et al. | | WO | WO 99/11644 | 3/1999 |
| 6,197,785 B1 | 3/2001 | Jackson et al. | | WO | WO 99/11645 | 3/1999 |
| 6,201,020 B1 | 3/2001 | Zhang | | WO | WO 99/11649 | 3/1999 |
| 6,235,748 B1 | 5/2001 | Li et al. | | WO | WO 99/59973 | 11/1999 |
| 6,291,425 B1 | 9/2001 | Li et al. | | WO | PCT/US99/30971 | 3/2000 |
| 6,306,889 B1 | 10/2001 | Li et al. | | WO | WO 00/32579 | 6/2000 |
| 6,514,983 B1 * | 2/2003 | Li et al. ............ 514/285 | | WO | WO 00/39070 | 7/2000 |
| | | | | WO | WO 00/39104 | 7/2000 |
| FOREIGN PATENT DOCUMENTS | | | | WO | WO 00/42040 | 7/2000 |
| BE | 562948 | 6/1960 | | WO | WO 00/44726 | 8/2000 |
| BE | 628255 | 5/1963 | | WO | WO 00/64878 | 11/2000 |
| CA | 1000701 | 11/1976 | | WO | WO 00/67734 | 11/2000 |
| CA | 1274339 | 9/1990 | | WO | WO 00/68206 | 11/2000 |
| CA | 1278141 | 12/1990 | | WO | WO 01/16136 | 3/2001 |
| CH | 463 778 | 11/1968 | | WO | WO 01/16137 | 3/2001 |
| DE | 282711 | 3/1915 | | WO | WO 01/42219 | 6/2001 |
| DE | D.R.P. 282711 | 3/1915 | | WO | WO 01/44219 | 6/2001 |
| DE | 963 184 | 5/1957 | | | | |
| DE | A-2111910 | 10/1971 | | | | |
| DE | A-2429515 | 1/1975 | | | | |
| DE | 26 50 226 | 5/1978 | | | | |
| DE | 33 32 633 A | 4/1985 | | | | |
| EP | 0 005 232 A | 11/1979 | | | | |
| EP | 0 126 684 B1 | 11/1984 | | | | |
| EP | 0 197 718 B1 | 10/1986 | | | | |
| EP | 0 219 208 B1 | 4/1987 | | | | |
| EP | 0 212 959 B1 | 3/1988 | | | | |
| EP | 355 750 | 2/1990 | | | | |
| EP | 0 393 926 | 10/1990 | | | | |
| EP | 393926 | 10/1990 | | | | |
| EP | 0 539 805 | 5/1993 | | | | |
| EP | 0 555 750 | 8/1993 | | | | |
| EP | 0 638 309 A1 | 2/1995 | | | | |
| EP | 0676 201 | 10/1995 | | | | |
| FR | 1 199 252 | 12/1959 | | | | |
| FR | 7 723 M | 3/1970 | | | | |
| FR | 2 205 333 | 5/1974 | | | | |
| FR | 2 305 182 | 10/1976 | | | | |

OTHER PUBLICATIONS

Griffin et al, "The role of inhibitors of poly(ADP-ribose) polymerase as resistance-modifying agents in cancer therapy" Biochemie, vol. 77. pp. 408-422 (1995).*

Bowman et al, "Differential effects of the poly (ADP-ribose) polymerase (PARP) inhibitor NU1025 on topoisomerase I and II inhibitor cytotoxicity in L1210 cells in vitro" British Journal of Cancer, vol. 84(1), pp. 106-112 (2001).*

Virag and Szabo, "The Therapeutic Potential of Poly(ADP-ribose) Polymerase Inhibitors" Pharmacological Reviews, vol. 54, pp. 375-429 (2002).*

Cosi, "New inhibitors of poly(ADP-ribose) polymerase and their potential therapeutic targets" Expert Opinion on Therapeutic Patents, vol. 12(7), pp. 1047-1071 (2002).*

Al-Dabbagh and Smith, "Species differences in oxidative drug metabolism: some basic considerations." Archives of toxicology. Supplement. Archiv fur Toxikologie. supplement, vol. 7, pp. 219-231 (1984).*

Hans Bundgaard, Design of Prodrugs, p. 1. © 1985 Elsevier Science Publishers.*

Richard B. Silverman, The Organic Chemistry of Drug Design and Drug Action, pp. 352-400. © 1992 Academic Press, Inc.*
Sieglitz et al, "3-Hydroxyfluoroanthene-1-, -2-, and -19-carboxylic acids" Chemische Berichte, vol. 95, pp. 3013-3029 (1962), as abstracted by CAPLUS.*
Worker, Charlotte "A novel PARP inhibitor, ion channel modulation and AD therapies" IDrugs, vol. 2(9), pp. 859-860 (1999).*
Sieglitz et al, "3-Hydroxyfluoroanthene-1-, -2-, and -10-carboxylic acids" Chemische Berichte, vol. 95, pp. 3013-3029 (1962).*
Biochemical and Biophysical Research Communications, 278(3) Nov. 30, 2000, 590-598, Zhang et al.
Bioorganic & Medicinal Chem. Letters, 11 1687-1690, 2001, Li et al.
Brain Research, 842 109-118, 1999, Sauer et al.
Can. J. Chem., vol. 49, 2797-2802, 1971, Homing.
Chem. Lett., 39-42, 1990, Chiba et al.
Circ. Res., 83:85-94, 1998, Zingarelli et al.
Emerging Drugs—Ashley Pub., 4:209-221, 1999, Zhang et al.
ISR for PCT/US01/15571, 2001, PCT.
European Journal of Pharmacology, 351 p. 377, 1998, Endres et al.
Gastroenterology, 1999; 116: p. 335, Zingarelli et al.
Heterocycles, 2000, 52(1) 325-332, Zhao et al.
Heterocycles, 1990, 31(3) 419-422, Friary et al.
Idrugs, 2001 4(7):804-812, Li et al.
J. Chem. Soc., 812, 1956, McConnell et al.
J. Med. Pharm., 3; 1961; 157, 159, Gooties et al.
J. Mol. Cell Cardiol, 31, 297-303, 1999, Grupp et al.
J. Phys. Org. Chem, 10; 7; 1997; 499-513, Arnett et al.
Journal of Medicinal Chemistry, 35(5)823-832, 1992, Ocain.
Journal of Medicinal Chemistry, 1979, vol. 22, No. 7,845-849, Lazar et al.
Life Sciences, 63 (23) 2133, 1998, Szabo.
Neurological Research, vol. 17, Aug. 1995, (285-288), Zhang et al.
Nucleic Acids Research, 29(3) 841-849, 2001, Simbulan-Rosenthal et al.
Shock, 13(1) p. 80, 2000, Yang et al.
Shock, 9(5) p. 341, 1998, Szabo.
Soc. for Neuro., 28th Ann Meeting, L.A., CA#480.14, 1998, Zhang et al.
Soc. for Neuro., 28th Ann Meeting, L.A., CA#480.16, 1998, Lautar et al.
Soc. for Neuro., 28th Ann Meeting L.A. CA#433.9, 1998, Williams et al.
Tetrahedron, 48(4) 1253-1262, 1990, Duval et al.
Tetrahedron Letters, 33(45) 6775-6778, 1992, Lopes.
TIPS, Apr. 1999 (vol. 20) 171-181, Pieper et al.
Abstr Pap Am Chem Soc, 206 (2), 1993, Slama et al.
Abstract, 1994:425593, Zailsev et al.
Aldrich, Catalog #23, 559-8.
Angew. Chem., 76:1, 50, 1964, Baer et al.
Ann., 673:132-36, 1964, Reid et al.
Ann. Chem., 688:177-88, 1965, Reid et al.
Ann. N Y Acad Sci, 825:366-79, 1997, Cosi et al.
Annu. Rev. Neurosci, 13, 171-82, 1990, Choi et al.
Anticancer Drug Des., 7:107-17, 1991, Suto et al.
Anticancer Drug Design, 10(6):507-14, Sep. 1995, Griffin et al.
Anti-Cancer Drug Design, 10(6): 507-14, 1995, R. Griffin et al.
Anticancer Research, 11: 881-888, 1991, Sakagami et al.
Arch. Pharm. Ber. Dtsch. Pharm. Ges., 300:6, 533-39, 1967, Reisch.
Bellstein Handbook of Organic Chem., Reg. No. 158523, 1950.
Beilstein Handbook of Organic Chem., Reg. No. 233692, 1956.
Beilstein Handbook of Organic Chem., Reg. No. 618403, 1988, Dokunichin.
Beilstein Handbook of Organic Chem., Reg. No. 827161, 1988, Dokunichin.
Beilstein Handbook of Organic Chem., Reg. No. 821484, 1988, Dokunichin.
Beilstein Handbook of Organic Chem., Reg. No. 619108, 1988, Dokunichin.
Beilstein Handbook of Organic Chem., Reg. No. 657772, 1988, Dokunichin.
Beilstein Handbook of Organic Chem., Reg. No. 653888, 1988, Dokunichin.
Beilstein Handbook of Organic Chem., Reg. No. 807993, 1988, Sielitz.
Beilstein Handbook of Organic Chem. Reg. No. 746893, 1988, Dokunichin.
Beilstein Handbook of Organic Chem. Reg. No. 656117, 1988, Gomes.
Beilstein Handbook of Organic Chem., Reg. No. 1571164, 1988, Rokach.
Beilstein Handbook of Organic Chem., Reg. No. 1541605, 1988, Humber et al.
Beilstein Handbook of Organic Chem., Reg. No. 751834, 1988, Mavoungou Gomes.
Beilstein Handbook of Organic Chem., Reg. No. 670954, 1988, Mavoungou Gomes.
Beilstein Handbook of Organic Chem., Reg. No. 649696, 1988, Dokunikhin.
Beilstein Handbook of Organic Chem., Reg. No. 530731, 1988, Dokunichin.
Beilstein Handbook of Organic Chem., Reg. No. 660681, 1988, Dokunichin.
Beilstein Handbook of Organic Chem., Reg. No. 4483194, 1991, Oleinik.
Beilstein Handbook of Organic Chem., Reg. No. 4494786, 1991, Oleinik.
Beilstein Handbook of Organic Chem., Reg. No. 3140506, 1998.
Beilstein Handbook of Organic Chem., Reg. No. 56052, 1998.
Beilstein Handbook of Organic Chem., Reg. No. 332938, 1998.
Beilstein Handbook of Organic Chem., Reg. No. 254129, 1998.
Beilstein Handbook of Organic Chem., Reg. No. 245245, 1998.
Beilstein Handbook of Organic Chem., Reg. No. 244756, 1998.
Beilstein Handbook of Organic Chem., Reg. No. 222316, 1998.
Beilstein Handbook of Organic Chem., Reg. No. 207532, 1998.
Beilstein Handbook of Organic Chem., Reg. No. 207516, 1998.
Beilstein Handbook of Organic Chem., Reg. No. 165349, 1998.
Beilstein Handbook of Organic Chem., Reg. No. 161148, 1998.
Beilstein Handbook of, Reg. No. 2213597, 1999.
Beilstein Handbook of Organic Chem., Reg. No. 13823, 1999.
Biochem, J., 185, 775-77, 1980, Purnell et al.
Biochemical and Biophysical Research Communications, 136(3), 1110-15, 1986, Tanuma et al.
Biochemical and Biophysical Research Communications, 195, No. 2, 558-564, 1993, Jesser et al.
Biochemical and Biophysical Research Communications, 195(2), 558-64, 1993, Jesser et al.
Biochemical and Biophysical Research Communications, 210. No. 2, 329-337, 1995, Aoki et al.
Biochemical and Biophysical Research Communications, 220, 411-17, 1998, Uchiumi et al.
Biochemical and Biophysical Research Communications, 236, 265-69, 1997, Maruta et al.
Biochemical and Biophysical Research Communications, 245, 1-10, 1998, Rhun et al.
Biochemical Society Transactions, vol. 8 (2), 192-193, 1980, Whitby et al.
Biochemical Society Transactions, 21:330-334, 1993, Beckman et al.
Biochemistry, 30, 5907-5912, 1991, Maruta et al.
Biochemistry International, 16, No. 3, 397-403, 1988, Concha et al.
Biochemistry International, 19, No. 6, 1395-1402, 1989, Tanuma et al.
Biochemistry International, 18, No. 4, 701-708, 1989, Tanuma et al.
Biochemistry International, 24, No. 5, 889-897, 1991, Tsai et al.
Biochimica et Biophysica Acta, 827, 228-234, 1985, Tavassoli et al.
Biochimica et Biophysica Actas, 1158, 251-56, 1993, Aoki et al.
Biochimie, vol. 77 No. 6, pp. 408-422, 1995, Griffin et al.
Br. J. Pharm., 117:619-32, 1998, Southan et al.
Brain, 122,247-253, 1999, Love.
Brain Res., 809:58-67, 1998, Cosl et al.
Brain Res., 710: 169-77, 1998, Wallis et al.
Brain Res. 729:264-69, 1998, Cosl et al.
Brit. J. Pharm., 122:493-503, 1997, Cuzzocrea.
Bull. Chem. Soc. Jpn., 61(6):2238-40, 1988, Sato et al.
Bull. Soc. Chim. Fr., 233, 1962, Granger et al.
C. R. Acad. Sci., 275:17, 961-64, 1972, Michailidis et al.
Can. J. Chem, 73, 319-35, 1995, Desilets et al.
Cell, 94, 325-337, 1998, Kuida et al.
Cell, 94, 339-352, 1998, Hakem et al.
Cell Biology and Toxicology, 9, No. 2, 165-175, 1993, Clayson et al.
Cerebrovascular Disease, 319-25, 1997, Dawson et al.
Chem Abstracts, 52:17 (14606h) (Sep. 10, 1958), Ochiai et al.

Chem Abstracts, 55:6 (5491ce) (Mar. 20, 1961), Ochiai et al.
Chem Abstracts, 58:4 (3425d) (Feb. 18, 1963), Hayashi et al.
Chem Abstracts, vol. 126,No. 17,229493f (Apr. 28, 1997), Angeliki.
Chem. Abstracts, 64:695e, 1968, Ried et al.
Chem. Ber., 46, pp. 2087, 2089, 1913, Kardos.
Chemical Abstract, 54:22648a, Nikitskaya et al.
Chemical Abstract, vol. 51:1960, 1957, Taylor et al.
Chemical Abstract, vol. 52:5846a, 1958, Schmidt-Nickels.
Chemical Abstract, vol. 52:6285, 1958, Ohta.
Chemical Abstract, vol. 52:4646, 1958, Gilman et al.
Chemical Abstract, vol. 52:5846b, 1958, Gateff et al.
Chemical Abstract, vol. 54:22647, 1960, Campbell.
Chemical Abstract, vol. 55:12868a, 1961.
Chemical Abstract, vol. 55:12868b, 1961.
Chemical Abstract, vol. 55:12868c, 1961.
Chemical Abstract, vol. 58:7884, 1963, Sieglitz.
Chemical Abstract, vol. 59:10037b, 1963, Dokunikhin et al.
Chemical Abstract, vol. 59:10037c, 1963, Hazard et al.
Chemical Abstract, vol. 61:15194, 1964, Tsuboi.
Chemical Abstract, vol. 61:13305h, 1964, Quelet.
Chemical Abstract, vol. 61:9493g, 1964, Dokunikhin et al.
Chemical Abstract, vol. 61:9494a, 1964, Dokunikhin et al.
Chemical Abstract, vol. 61:9493f, 1964, Bodea et al.
Chemical Abstract, vol. 61:13305g, 1964, Badger et al.
Chemical Abstract, vol. 63:7006, 1965, Perrin.
Chemical Abstract, vol. 62:5259, 1965, Lakeside Lab., Inc.
Chemical Abstract, vol. 62:9129e, 1965, Kuehn.
Chemical Abstract, vol. 63:4258, 1965, Keene et al.
Chemical Abstract, vol. 62:9129g, 1965, Klosa.
Chemical Abstract, vol. 65:15320a, 1966, Kametani.
Chemical Abstract, vol. 64:3526h, 1966, Crossland.
Chemical Abstract, vol. 65:15319h, 1966, Humber et al.
Chemical Abstract, vol. 69:87767, 1968, Hofer.
Chemical Abstract, vol. 68:59420, 1968, Chandler et al.
Chemical Abstract, vol. 70:3629, 1969, Weis.
Chemical Abstract, vol. 70:67988, 1969, Resplandy et al.
Chemical Abstract, vol. 70:115926, 1969, Hofer.
Chemical Abstract, vol. 70:4079, 1969, Coyne et al.
Chemical Abstract, vol. 73:35200, 1970, Pan et al.
Chemical Abstract, vol. 72:121337, 1970, Pan et al.
Chemical Abstract, vol. 74:111797, 1971, Mavoungou-Gomes.
Chemical Abstract, vol. 75:98422, 1971, Campbell.
Chemical Abstract, 74:110112y (p. 252 May 10, 1971), Damas.
Chemical Abstract, vol. 77:61927, 1972, Zinchenko.
Chemical Abstract, vol. 76:14566, 1972, Rodway.
Chemical Abstract, vol. 76:85774, 1972, Mavoungou-Gomes.
Chemical Abstract, vol. 78:123624, 1973, Swenton et al.
Chemical Abstract, vol. 78:68700, 1973, Roehm et al.
Chemical Abstract, vol. 78:58193, 1973, Mondon et al.
Chemical Abstract, vol. 78:84227, 1973, Kraatz et al.
Chemical Abstract, vol. 78:29384, 1973, Forrester et al.
Chemical Abstract, vol. 78:29593, 1973, Cerbai et al.
Chemical Abstract, vol. 81:37489, 1974, Cerbai et al.
Chemical Abstract, vol. 81:37417, 1974, Baddar.
Chemical Abstract, vol. 82:171011, 1975, Rodway.
Chemical Abstract, vol. 82:170471, 1975, Mavoungou-Gomes.
Chemical Abstract, vol. 83:27978, 1975, Baddar.
Chemical Abstract, vol. 84:42754, 1976, Zaitsev.
Chemical Abstract, vol. 84:3986, 1976, Zaitsev.
Chemical Abstract, vol. 85:182, 1976, Tullar et al.
Chemical Abstract, vol. 84:16943, 1976, Minatoya et al.
Chemical Abstract, vol. 85:77216, 1976, Ege et al.
Chemical Abstract, vol. 84:4857, 1976, Cookson.
Chemical Abstract, 85(1976)159898a, 1976.
Chemical Abstract, vol. 86:171282, 1977, Humber.
Chemical Abstract, vol. 87:152015, 1977, Houlihan.
Chemical Abstract, vol. 87:5778, 1977, Fomenko et al.
Chemical Abstract, vol. 82:30602, 1978, Minatoya et al.
Chemical Abstract, vol. 90:64861, 1979, Takahashi.
Chemical Abstract, vol. 91:39035, 1979, Migachev.
Chemical Abstract, vol. 90:38734, 1979, Mavoungou-Gomes.
Chemical Abstract, vol. 92:181104e, 1980, Ryabukhina et al.
Chemical Abstract, vol. 92:146482, 1980, Rokach.
Chemical Abstract, vol. 92:41620, 1980, Migachev et al.
Chemical Abstract, vol. 92:41511, 1980, Migachev et al.
Chemical Abstract, vol. 93:26178, 1980, Gomes.
Chemical Abstract, vol. 92:198336, 1980, Cabares.

Chemical Abstract, 92:22393, 1980, Simmonds.
Chemical Abstract, vol. 95:80661, 1981, Narasimhan et al.
Chemical Abstract, vol. 95 (9):80666, 1981, Migachev et al.
Chemical Abstract, vol. 95:80688, 1981, Migachev et al.
Chemical Abstract, vol. 95:42867, 1981, Migachev et al.
Chemical Abstract, vol. 95:42866, 1981, Migachev et al.
Chemical Abstract, vol. 95:187120, 1981, Migachev et al.
Chemical Abstract, vol. 95:168911, 1981, Houlihan.
Chemical Abstract, vol. 96:6539m, p. 592, 1982, Singh et al.
Chemical Abstract, vol. 96:68519, 1982, Leardini et al.
Chemical Abstract, vol. 97:38635, 1982, Krapelka.
Chemical Abstract, vol. 97:126680, 1982, Grimshaw et al.
Chemical Abstract, vol. 100:103453, 1984, Prostakov et al.
Chemical Abstract, vol. 100:191713, 1984, Orlic-Nuber et al.
Chemical Abstract, vol. 100:139054, 1984, Oleinik.
Chemical Abstract, vol. 102:203854, 1985, Migachev et al.
Chemical Abstract, vol. 105:60505, 1986, Andrievskii et al.
Chemical Abstract, vol. 106 (67553), 1987, Pellefier.
Chemical Abstract, vol. 107:23262, 1987, Cabares.
Chemical Abstract, vol. 107:39655v, 1987, Bondarenko et al.
Chemical Abstract, vol. 108:21627, 1988, Duval.
Chemical Abstract, vol. 110:230971, 1989, Val'kova et al.
Chemical Abstract, vol. 113:190649, 1990, Val'kova et al.
Chemical Abstract, vol. 112:44716, 1990, Korol'kova et al.
Chemical Abstract, vol. 112:128235, 1990, Korol'kova et al.
Chemical Abstract, vol. 112:216749, 1990, Benson et al.
Chemical Abstract, vol. 114: 143456, 1991, Walser.
Chemical Abstract, vol. 115 (232107), 1991, Nagao.
Chemical Abstract, vol. 115:70731f, 1991, Donshikh et al.
Chemical Abstract, vol. 115:158338, 1991, Buckman et al.
Chemical Abstract, vol. 114:42543, 1991, Andrievskii et al.
Chemical Abstract, vol. 119:72127, 1993, Zaitsev et al.
Chemical Abstract, vol. 118:191567, 1993, Dow.
Chemical Abstract, vol. 118:80722, 1993, Dininno et al.
Chemical Abstract, vol. 118:101709, 1993, Dininno et al.
Chemical Abstract, vol. 120:134231, 1994, Rocca et al.
Chemical Abstract, vol. 121:220651v, 1994, Pawlowska et al.
Chemical Abstract, vol. 121:172572, 1994, Liu et al.
Chemical Abstract, vol. 120:95793, 1994, Kyota et al.
Chemical Abstract, vol. 121:57315, 1994, Dow et al.
Chemical Abstract, vol. 120:148508p, 1994, Barrow et al.
Chemical Abstract, vol. 123:505, 1995, Weltin et al.
Chemical Abstract, vol. 122:10865, 1995, Lamba et al.
Chemical Abstract, vol. 122:170499, 1995, Korol'kova et al.
Chemical Abstract, vol. 123:256711, 1995, Kalindjian et al.
Chemical Abstract, vol. 122:170250, 1995, Gorio et al.
Chemical Abstract, vol. 122:187249, 1995, Dininno et al.
Chemical Abstract, 122:316902, 1995, Desilets et al.
Chemical Abstract, 122:316901, 1995, Desilets et al.
Chemical Abstract, vol. 122:187526, 1995, Langlois et al.
Chemical Abstract, vol. 125:87882, 1996, Yamaguchi et al.
Chemical Abstract, vol. 124:331706, 1996, Silverman et al.
Chemical Abstract, vol. 124:131261, 1996, Richter.
Chemical Abstract, vol. 126:115554, 1996, Malhotra et al.
Chemical Abstract, vol. 125:246943, 1996, Korol'kova et al.
Chemical Abstract, vol. 125:277462, 1996, Ge et al.
Chemical Abstract, 124:202047, 1996, Fernandez et al.
Chemical Abstract, vol. 128:36109, 1997, Sakai et al.
Chemical Abstract, vol. 127:234258, 1997, Reddy et al.
Chemical Abstract, vol. 127:81282, 1997, Marek et al.
Chemical Abstract, vol. 128:34752, 1997, Jones et al.
Chemical Abstract, vol. 127:80243, 1997, Banister et al.
Chemical Abstract, abstract No. 17462, 1998, Yoshida et al.
Chemical Abstract, vol. 129:104224, 1998, West.
Chemical Abstract, vol. 126:138099, 1998, Weltin et al.
Chemical Abstract, vol. 130:24816, 1998, Park et al.
Chemical Abstract, vol. 128:75320, 1998, Jones et al.
Chemical Abstract, vol. 128:185850, 1998, Cookson et al.
Chemical Abstract, vol. 129:54301, 1998, Albright et al.
Chemical Abstract, No. 816103, 1998, Albright et al.
Chemical Abstracts, vol. 51 (21) 18420d, 1958, Tanida.
Chemical Abstracts, vol. 82, No. 5, 5271c, Mar. 1965.
Chemical Abstracts, vol. 76 (25) 153704b, 1972, Pozharskii et al.
Chemical Abstracts, vol. 88 (7) 49887, 1978, Szadowski.
Chemical Abstracts, 88, No. 13, 505 (88:89502c), 1978, Dokunikhin et al.
Chemical Abstracts, 94, No. 12, 637(192098y), 1981, Migachev.

Chemical Abstracts, Registry No. 17 1399-15-8, 1998.
Chemical Abstracts, Registry No. 14223 8-47-9, 1998.
Chemical Abstracts, 85:159898a, 85, No. 21, 531, 1974, Upadysheva et al.
Chemical and Pharmaceutical Bulletin, vol. 26, No. 12, pp. 3682-3694, 1978, Hamada et al.
Chemische Berichte, vol. 102, 1161-1176, 1969, Kauffmann et al.
Eur. J. Biochem., vol. 244, pp. 15-20, 1997, Van Gool et al.
Eur. J. Med Chem. 29, 925-40, 1994, Langlois et al.
Eur. J. Pharm. 204, 339-40, 1991, Nowicki et al.
Gazz, Chim. Ital., 91:1345-51, 1962, Di Maio et al.
Gazz. Chim. Ital., 91:1124-32, 1962, Di Maio et al.
Gazz. Chim. Ital., 94:5, 590-94, 1964, Di Maio et al.
Hawleys Chemical Condense Dictionary, Sax (ED) 11th Ed, 1987 p898, 1987, Hawley's.
Heterocycles, 22:2, 237-40, 1984, Naito et al.
Int. J. Immunopharmac, 17, No. 4, 265-271, 1995, Weltin et al.
Int. J. Radiat. Biol., vol. 72, No. 6, pp. 685-692, 1997, Weltin et al.
Int. J. Radiat. Biol. Relat. Stud. Phys. Chem. Med., vol. 48, No. 5, pp. 675-680, 1985, Harris.
Int. J. Oncol, 8:239-52, 1996, Bauer et al.
IPER for PCT/US98/18189.
IS&T's Tenth Int'l, 246-248, 1941, Richter et al.
ISR for PCT/US98/18185.
ISR for PCT/US98/18186.
ISR for PCT/US98/18187.
ISR for PCT/US98/18188.
ISR for PCT/US98/18189.
ISR for PCT/US98/18195.
ISR for PCT/US98/18196.
ISR for PCT/US98/18226.
ISR for PCT/US99/30971.
ISR for PCT/US99/30979.
Itsu Kenkusho Nempo, 16:15-23, 1971, Ochiai et al.
J Cerebral Flood Flow Metabol., 17(11):1143-51, 1997, Endres et al.
J Chem. Soc., 11:1293-97, 1978, Davies et al.
J. Am. Chem. Soc., 78:5104-8, 1956, Taylor et al.
J. Biol. Chem, 270:19, 11176-80, 1995, Heller et al.
J. Biol. Chem., 246(20), 6362-64, 1972, Miwa et al.
J. Biol. Chem., 261(32), 14902-11, 1986, Hatakeyama et al.
J. Biol. Chem., 262(36), 17641-50, 1987, Ikejima et al.
J. Biol. Chem., 263(23), 11037-40, 1988, Ikejima et al.
J. Biol. Chem., 267(20), 14436-42, 1992, Tsai et al.
J. Biol. Chem., 267:3, 1569-75, 1992, Banasik et al.
J. Biol. Chem., 272:9030-36, 1997, Szabo et al.
J. Chem. Soc., 12:2231-2241, 1971, Barton.
J. Chem. Res., Synop., 8:302, 1995, Mueller et al.
J. Chem. Res., Synop., 2:126, 1996, Mueller et al.
J. Chem. Soc., pp. 1979-1984, 1929, Blount et al.
J. Chem. Soc. 1624-28, 1958, Johnson.
J. Chem. Soc., 4295-98, 1962, Brown et al.
J. Chem. Soc., 1:14, 1747-51, 1974, Ninomiya et al.
J. Chem. Soc., 1:7, 763-70, 1974, Bailey et al.
J. Exp Med., vol. 186, No. 7, Oct. 6, 1997, 1041-9, Szabo.
J. Het. Chem, vol. 7, pp. 597-605, 1970, Pan et al.
J. Heterocycl. Chem., 20:5, 1407-9, 1983, Rougeot et al.
J. Immuno., 153:3319-25, 1994, Hughes et al.
J. Med. Chem., 38, 389-393, 1995, Slama et al.
J. Med. Chem., 38, 4332-4336, 1995, Slama et al.
J. Neurochem, 65:3, 1411-14, 1995, Zhang et al.
J. Neurosci., 13:6, 2651-61, 1993, Dawson et al.
J. Neurosci., 16:8, 2479-87, 1996, Dawson et al.
J. Neuroscience Res., 47: 372-383, 1997, Ceruti et al.
J. of Biological Chemistry, 261(2), 965-69, 1986, Tanuma et al.
J. Org Chem., 29:3, 681-85, 1964, Masamune et al.
J. Org Chem., 47, 2043-2047, 1982, Taylor et al.
J. Org. Chem., vol. 23, pp. 1071-1072 Jul. 1958, Robinson, et al.
J. Org. Chem., 29:11, 3180-85, 1964, Baer et al.
J. Org. Chem., 43:11, 2190-96, 1978, Eisch et al.
J. Urol., vol. 150, pp. 1526-1532, 1993, Sklar et al.
JACS, 71:937-8 (Mar. 1949), Wilson et al.
JACS, 76:4396-8 (Sep. 5, 1954), Wright.
Japanese J. Pharm., 75, Supp. 1:102, 1997, Szabo et al.
Japanese J. Pharm., 75, Supp. 1:15, 1997, Satzman et al.
JCS, pp. 4067-4075, 1952, Peak et al.
JCS, pp. 1294-1304, 1956, Albert et al.
JCS, pp. 2384-2396, 1959, Albert et al.
Journal of Cellular Biochemistry, 29:361-372, 1985, Bolander, Jr.
Journal of Cerebral Blood Flow and Metabolism, 17 No. 11, 1137-1142, 1997, Takahashi et al.
Journal of Heterocyclic Chemistry, vol. 3, pp. 466-469, Dec. 1966, Aparajithan.
Journal of Heterocyclic Chemistry, vol. 15, pp. 1513-1514, 1978, Nuvole et al.
Journal of Medicinal Chemistry, vol. 20 (3) 449-452, 1977, Diana et al.
Journal of Neurochemistry, 70, No. 2, 501-508, 1998, Cookson et al.
Journal of Organic Chemistry, vol. 11, No. 3, 239-246, 1946, Bergstrom et al.
Journal of Organic Chemistry, 53(20):4650-3, 1988, D. Dumas.
Journal of the Chemical Society, pp. 1799-1803, 1972, Singh et al.
Journal of the Chemical Society, vol. 9, 944-950, 1976, Loewenthal et al.
Justus Liebigs Ann. Chem., 388, p. 212, 1912, Ullmann et al.
Med Chem. Res., 6:2, 81-101, 1996, Castan et al.
Molec. Cell. Biochem., 138:185-97, 1994, Banasik et al.
Mutation Research, 218, 67-74, 1989, Gonzalez et al.
Mutation Research, 350, 25-34, 1996, Wachsman.
Nature Medicine, JHU, 1997, Eliasson et al.
Neuron, 1, 623-634, 1988, Choi.
NeuroReport, 5:3, 245-48, 1993, Wallis et al.
Oncol. Res., 6:9, 399-403, 1994, Weltin et al.
PNAS, 96:5774-5779 (May 1999), Mandir et al.
Pain, vol. 72, pp. 355-368, 1997, Mao et al.
Pharm. Bull. 5:289-91, 1957, Ochiai et al.
Phosphorus Sulfur, vol. 14, No. 1, pp. 131-138, 1983, Becher et al.
Proc. Natl. Acad Sci. USA, 88:6368-71, 1991, Dawson et al.
Proc. Natl. Acad. Sci. USA, 93:1753-58, 1996, Szabó et al.
Proc. Natl. Acad Sci. USA, 94:679-83, 1997, Thiemermann et al.
Proc. Natl. Acad. Sci. USA, vol. 93, pp. 7481-7485, 1996, Ruf et al.
Radiat. Res., 101:29-46, 1985, Olelnick.
Radiat. Res., vol. 116 No. 3, pp. 442-452, 1988, Paaphorst et al.
Res. Comm. Mol. Pathol. Pharmacol., vol. 95 No. 3, pp. 241-252, 1997, Lam.
Ric. Sci., 38:3, 231-33, 1968, Di Maio et al.
Rocz. Chem., 41:1,89-101, 1967, Schoen et al.
Science, 223:589-91, 1984, Milam et al.
Science, 263:687-89, 1994, Zhang et al.
Science, 265:1883-1885, 1994, Huang et al.
Science, 282, 1484-1487, 1998, Smith et al.
Shock, 5(4):258-64, 1996, Zingarelli et al.
Spin Label Analogue of ATP, 246, No. 20, 6362-6364, 1971, Miwa et al.
Switzerland Patent, 601 246, 1978.
Terato., Carcino., and Muta., 16:219-27, 1998, Cristovao et al.
Tetrahedron, supp. 8, part 1, pp. 305-312, 1966, Tamayo et al.
Tetrahedron Letters, 32, No. 35, 4525-4528, 1991, Chida et al.
Tetrahedron Letters, 36:33, 5983-86, 1995, White et al.
Tetrahedron Letters, 52:9, 3117-34, 1998, White et al.
The EMBO Journal, vol. 16 No. 19, pp. 6018-6033, 1997, Vaziri et al.
The Journal of Biological Chemistry, 242, No. 22, 5301-5307, 1967, Futai et al.
The Journal of Biological Chemistry, vol. 257, No. 21, 12872-12877, 1982, Wielckens et al.
The Journal of Biological Chemistry, 259, No. 2, 986-995, 1984, Oka et al.
The Journal of Biological Chemistry, 261, No. 2, pp. 965-969, 1986, Tanuma et al.
The Journal of Biological Chemistry, 263, No. 23, 11037-11040, 1988, Ikejima et al.
The Journal of Biological Chemistry, 272, No. 18, 11895-11901, 1997, Lin et al.
TiPS, 11, 379-387, 1990, Meldrum et al.
TIPS, in press, 1998, Pieper et al.
Trends Neurosci., 20:3, 132-139, 1997, Iadecola.
Vertex Pharmaceuticals Inc., PR Newswire, 1998.

* cited by examiner

Primary Examiner—Zachary C Tucker
(74) Attorney, Agent, or Firm—Connolly Bove Lodge Lodge & Hutz LLP
(57) ABSTRACT
The disclosure relates to compounds, pharmaceutical compositions and methods for inhibiting PARP by use of the disclosed compositions. The compounds of the disclosure have the following structures I, II and III:
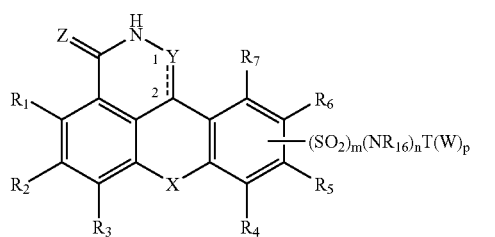
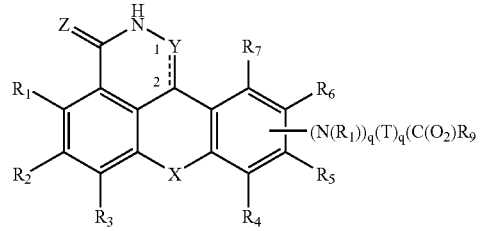
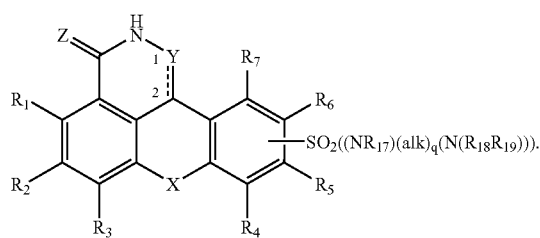
23 Claims, 2 Drawing Sheets

COMPOUNDS, METHODS AND PHARMACEUTICAL COMPOSITIONS FOR TREATING CELLULAR DAMAGE, SUCH AS NEURAL OR CARDIOVASCULAR TISSUE DAMAGE

The present application is a divisional of application Ser. No. 09/781,195, filed Feb. 13, 2001 (which issued as U.S. Pat. No. 6,716,828 on Apr. 4, 2004), which is a divisional of application Ser. No. 09/387,767, filed Sep. 1, 1999 (which issued as U.S. Pat. No. 6,291,425 B1 on Sep. 18, 2001), the entire contents of each of which are incorporated herein by reference.

FIELD OF THE INVENTION

The present invention relates to inhibitors of the nuclear enzyme poly(adenosine 5'-diphospho-ribose) polymerase ["poly(ADP-ribose) polymerase" or "PARP". which is also referred to as ADPRT (NAD:protein (ADP-ribosyl transferase (polymersing)). pADPRT (poly(ADP-ribose) transferase) and PARS (poly(ADP-ribose) synthetase) and provides compounds and compositions containing the disclosed compounds. Moreover, the present invention provides methods of using the disclosed PARP inhibitors to prevent and/or treat tissue damage resulting from cell damage or death due to necrosis or apoptosis; neural tissue damage resulting from, for example, ischemia and reperfusion injury, such as cerebral ischemic stroke, head trauma or spinal cord injury; neurological disorders and neurodegenerative diseases, such as, for example, Parkinson's or Alzheimer's diseases and multiple sclerosis; to prevent or treat vascular stroke; to treat or prevent cardiovascular disorders, such as, for example, myocardial infarction; to treat other conditions and/or disorders such as, for example, age-related muscular degeneration, AIDS and other immune senescence diseases, arthritis, atherosclerosis, cachexia, cancer, degenerative diseases of skeletal muscle involving replicative senescence. diabetes (such as diabetes mellitus), inflammatory bowel disorders (such as colitis and Crohn's disease). acute pancreatitis, mucositis, hemorrhagic shock, splanchnic arter occlusion shock, multiple organ failure (such as involving any of the kidney, liver, renal, pulmonary, retinal, pancreatic and/or skeltal muscle systems), acute autoimmune thyroiditis, muscular dystrophy, osteoarthritis, osteoporosis, chronic and acute pain (such as neuropathic pain), renal failure, retinal ischemia, septic shock (such as endotoxic shock), local and/or remote endothelial cell dysfunction (such are recognized by endo-dependent relaxant responses and up-regulation of adhesion molecules), inflammation and skin aging; to extend the lifespan and proliferative capacity of cells, such as, for example, as general mediators in the generation of oxidants, proinflammatory mediators and/or cytokines, and general mediators of leukocyte infiltration, calcium ion overload, phospholipid peroxidaion, impaired nitric oxide metabolism and/or reduced ATP production; to alter gene expression of senescent cells; or to radiosensitize hypoxic tumor cells.

BACKGROUND OF THE INVENTION

PARP (EC 2.4.2.30), also known as PARS (for poly(ADP-ribose) synthetase), or ADPRT (for NAD:protein (ADP-ribosyl) transferase (polymerising)), or pADPRT (for poly (ADP-ribose) transferase), is a major nuclear protein of 116 kDa. It is present in almost all eukaryotes. The enzyme synthesizes poly(ADP-ribose), a branched polymer that can consist of over 200 ADP-ribose units from NAD. The protein acceptors of poly(ADP-ribose) are directly or indirectly involved in maintaining DNA integrity. They include histones, topoisoinerases, DNA and RNA polymerases, DNA ligases, and $Ca^{2-}$- and $Mg^{2+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. Among the many functions attributed to PARP is its major role in facilitating DNA repair by ADP-ribosylation and therefore co-ordinating a number of DNA repair proteins. As a result of PARP activation, NAD levels significantly decline. While many endogenous and exogenous agents have been shown to damage DNA and activate PARP, peroxynitrite, formed from a combination of nitric oxide (NO) and superoxide, appears to be a main perpetrator responsible for various reported disease conditions in vivo. e.g., during shock and inflammation Extensive PARP activation leads to severe depletion of NAD in cells suffering from massive DNA damage. The short life of poly(ADP-ribose) (half-life<1 min) results in a rapid turnover rate. Once poly(ADP-ribose) is formed it is quickly degraded by the constitutively active poly(ADP-ribose) glycohydrolase (PARG), together with phosphodiesterase and (ADP-ribose) protein lyase. PARP and PARG form a cycle that converts a large amount of NAD to ADP-ribose. In less than an hour, over-stimulation of PARP can cause a drop of NAD and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to NAD depletion due to poly(ADP-ribose) turnover. Thus, PARP or PARG inhibition is expected to preserve the cellular energy level to potentiate the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages. P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues. (Zhang, J. "PARP inhibition: a novel approach to treat ischaemia/reperfusion and inflammation-related injuries". Chapter 10 in *Emerging Drugs* (1999) 4:209-221 Ashley Publications Ltd., and references cited therein.)

PARP production is activated by damaged DNA fragments which, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are constuned for every molecule of NAD (the source of ADP-ribose and PARP substrate) regenerated. NAD is depleted by massive PARP activation and, in the efforts to re-synthesize NAD, ATP may also be depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency (Zhang et al., "Nitric Oxide Activation of Poly(ADP-Ribose) Synthetase in Neurotoxicity". Science, 263:687-89 (1994) and Wallis et al., "Neuroprotection Against Nitric Oxide Injury with Inhibitors of ADP-Ribosylation". NeuroReport, 5:3. 245-48 (1993)). The potential role of PARP inhibitors in treating neurodegenerative diseases and head trauma has thus been recognized even if the exact mechanism of action has not yet been elucidated (Endres et al., "Ischemic Brain Injury is Mediated by the Activation of Poly(ADP-Ribose)Polymerase". J. Cereb. Blood Flow Metabol., 17:1143-51 (1997) and Wallis et al., "Traumatic Neuroprotection with Inhibitors of Nitric Oxide and ADP-Ribosylation, Brain Res., 710:169-77 (1996)).

Similarly, it has been demonstrated that single injections of PARP inhibitors have reduced the infarct size caused by ischemia and reperfusion of the heart or skeletal muscle in rabbits. In these studies, a single injection 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). Thiemerrmann et al., "Inhibition of the Activity of Poly(ADP Ribose) Synthetase Reduces Ischemia-Reperfusion Injury in the Heart and Skeletal Muscle". Proc. Natl. Acad. Sci. USA. 94:679-83 (1997). These results make it reasonable to suspect that PARP inhibitors could salvage previously ischemic heart or skeletal muscle tissue.

PARP activation can also be used as a measure of damage following neurotoxic insults following over-exposure to any of glutamate (via NMDA receptor stimulation), reactive oxygen intermediates, amyloid β-protein. N-methyl-4-phenyl-1,2,3,6-tetrahydropyridine (MPTP) or its active metabolite N-methyl-4-phenylpyridine ($MPP^-$), which participate in pathological conditions such as stroke, Alzheimer's disease and Parkinson's disease. Zhang et al., "Poly(ADP-Ribose) Synthetase Activation: An Early Indicator of Neurotoxic DNA Damage". J. Neurochem., 65:3, 1411-14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP inhibitors as Possible Neuroprotective Agents". Ann. N.Y. Acad. Sci., 825:366-79 (1997); and Cosi et al., "Poly(ADP-Ribose) Polymerase Inhibitors Protect Against MPTP-induced Depletions of Striatal Dopamine and Cortical Noradrenaline in C57B1/6 Mice", Brain Res., 729:264-69 (1996). Excessive neural exposure to glutamnate, which serves as the predominate central nervous system neurotransmitter and acts upon the N-methyl-D-aspartate (NMDA) receptors and other subtype receptors, most often occurs as a result of stroke or other neurodegenerative processes. Oxygen deprived neurons release glutamate in great quantities during ischemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Dawson et al., "Protection of the Brain from Ischemia". Cerebrovascular Disease. 319-25 (H. Hunt Batjer ed., 1997). Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro. Dawson et al., "Nitric Oxide Mediates Glutamate Neurotoxicity in Primary Cortical Cultures". Proc. Natl. Acad. Sci. USA. 88:6368-71 (1991); and Dawson et al., "Mechanisms of Nitric Oxide-mediated Neurotoxicity in Primary Brain Cultures". J. Neurosci., 13:6, 2651-61 (1993), Dawson et al., "Resistance to Neurotoxicity in Cortical Cultures from Neuronal Nitric Oxide Synthase-Deficient Mice", J. Neurosci., 16:8. 2479-87 (1996). Iadecola, "Bright and Dark Sides of Nitric Oxide in Ischemic Brain Injury". Trends Neurosci., 20:3, 132-39 (1997). Huang et al., "Effects of Cerebral Ischemia in Mice Deficient in Neuronal Nitric Oxide Synthase". Science, 265:1883-85 (1994). Beckman et al., "Pathological Implications of Nitric Oxide, Superoxide and Peroxyntrite Formation", Biochem. Soc. Trans., 21:330-34 (1993), and Szabó et al., "DNA Strand Breakage, Activation of Poly(ADP-Ribose) Synthetase, and Cellular Energy Depletion are Involved in the Cytotoxicity in Macrophages and Smooth Muscle Cells Exposed to Peroxynitrite", Proc. Natl. Acad. Sci. USA. 93:1753-58 (1996).

It is also known that PARP inhibitors, such as 3-amino benzamide, affect DNA repair generally in response, for example, to hydrogen peroxide or gamma-radiation. Cristovao et al., "Effect of a Poly (ADP-Ribose) Polymerase Inhibitor on DNA Breakage and Cytotoxicity Induced by Hydrogen Peroxide and γ-Radiation." Terato., Carcino., and Muta., 16:219-27 (1996). Specifically, Cristovao et al, observed a PARP-dependent recovery of DNA strand breaks in leukocytes treated wvith hydrogen peroxide.

PPRP inhibitors have been reported to be effective in radiosensitizing hypoxic tumor cells and effective in preventing tumor cells from recovering from potentially lethal damage of DNA after radiation therapy, presumably by their ability to prevent DNA repair. U.S. Pat. Nos. 5,032,617; 5,215,738; and 5,041,653.

Evidence also exists that PARP inhibitors are useful for treating inflammatory bowel disorders, such as colitis. Salzman et al., "Role of Peroxynitrite and Poly(ADP-Ribose) Synthase Activation Experimental Colitis." Japanese J.

Pharm., 75. Supp. 1:15 (1997). Specifically, Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology, and the energetc status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform". Br. J. Pharm., 117:619-32 (1996); and Szabó et al., "Mercaptoethylguanidine and Guanidine Inhibitors of Nitric Oxide Synthase React with Peroxynitrite and Protect Against Peroxynitrite-induced Oxidative Damage". J. Biol. Chem., 272:9030-36 (1997).

Evidence also exists that PARP inhibitors are useful for treating arthritis. Szabó et al., "Protective Effects of an Inhibitor of Poly(ADP-Ribose)Synthetase in Collagen-Induced Arthritis." Japanese J. Pharm., 75. Supp. 1:102 (1997): Szabó et al., "DNA Strand Breakage, Activation of Poly(ADP-Ribose)Synthetase, and Cellular Energy Depletion are Involved in the Cytotoxicity in Macrophages and Smooth Muscle Cells Exposed to Peroxynitrite." Proc. Natl. Acad. Sci. USA, 93:1753-58 (March 1996); and Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone (INH2BP)". Intl. J. Oncol., 8:239-52 (1996); and Hughes et al., "Induction of T Helper Cell Hyporesponsiveness in an Experimental Model of Autoimmunity by Using Nonmitogenic Anti-CD3 Monoclonal Antibody". J. Immuno., 153:3319-25 (1994).

Further, PARP inhibitors appear to be useful for treating diabetes. Heller et al., "Inactivation of the Poly(ADP-Ribose)Polymerase Gene Affects Oxygen Radical and Nitric Oxide Toxicity in Islet Cells." J. Biol. Chem., 270:19, 11176-80 (May 1995). Heller et al, used cells from mice with inactivated PARP genes and found that these mutant cells did not show $NAD^+$ depletion after exposure to DNA-damaging radicals. The mutant cells were also found to be more resistant to the toxicity of NO.

PARP inhibitors have been showvn to be useful for treating endotoxic shock or septic shock. Zingarelli et al., "Protective Effects of Nicotinamide Against Nitric Oxide-Mediated Delaved Vascular Failure in Endotoxic Shock: Potential Involvement of PolyADP Ribosyl Synthetase." Shock. 5:258-64 (1996), suggests that inhibition of the DNA repair cycle triggered by poly(ADP ribose) synthetase has protective effects against vascular failure in endotoxic shock. Zingarelli et al, found that nicotinamide protects against delayed. NO-mediated vascular failure in endotoxic shock. Zingarelli et al, also found that the actions of nicotinainide may be related to inhibition of the NO-mediated activation of the energy-consuming DNA repair cycle, triggered by poly(ADP ribose) synthetase. Cuzzocrea, "Role of Peroxynitrite and Activation of Poly(ADP-Ribose) Synthetase in the Vascular Failure Induced by Zvmosan-activated Plasma" Brit. J. Pharm., 122:493-503 (1997).

PARP inhibitors have been used to treat cancer. Suto et al., "Dihydroisoquinolinones: The Design and Synthesis of a New Series of Potent Inhibitors of Poly(ADP-Ribose) Polymerase". Anticancer Drug Des., 7:107-17 (1991). In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly(ADP-ribose) Polymerase, on Cultured Tumor Cells". Oncol. Res., 6:9, 399-403 (1994), discusses the inhibition of PARP activity, reduced proliferation of tumor cells, and a marked synergistic effect when tumor cells are co-treated with an alklating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. Mao et al., Pain, 72:355-366 (1997).

PARP inhibitors have also been used to extend the lifespan and proliferative capacity of cells including treatment of diseases such as skin aging. Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence diseases; and to alter gene expression of senescent cells, WO 98/27975.

Large numbers of known PARP inhibitors have been described in Banasik et al., "Specific Inhibitors of Poly (ADP-Ribose) Synthetase and Mono(ADP-Ribosyl)-Transferase", J. Biol. Chem., 267:3, 1569-75 (1992), and in Banasik et al., "Inhibitors and Activators of ADP-Ribosylation Reactions", Molec. Cell. Biochem., 138:185-97 (1994). However, effective use of these PARP inhibitors, in the ways discussed above, has been limited by the concurrent production of unwanted side-effects (Milam et al., "Inhibitors of Poly(Adenosine Diphosphate-Ribose) Synthesis: Effect on Other Metabolic Processes", Science, 223: 589-91 (1984)).

There continues to be a need for effective and potent PARP inhibitors which produce minimal side-effects. The present invention provides compounds, compositions for, and methods of inhibiting PARP activity for treating and/or preventing cellular, tissue and/or organ damage resulting from cell damage or death due to, for example, necrosis or apoptosis. The compounds and compositions of the present invention are specifically useful in ameliorating, treating and/or preventing neural tissue or cell damage, including that following focal ischemia and reperfusion injury. Generally, inhibition of PARP activity spares the cell from energy loss, preventing irreversible depolarization of the neurons and, thus, provides neuroprotection. While not wishing to be bound by any mechanistic theory, the inhibition of PARP activity by use of the compounds, compositions and methods of the present invention is believed to protect cells, tissue and organs by protection against the ill-effects of reactive free radicals and nitric oxide. The present invention therefore also provides methods of treating and/or preventing cells, tissue and/or organs from reactive free radical and/or nitric oxide induced damage or injury.

SUMMARY OF THE INVENTION

The present invention provides compunds which inhibit poly(ADP-ribose) polymerase ("PARP"), compositions containing these compounds and methods for using these PARP inhibitors to treat, prevent and/or ameliorate the effects of the conditions described herein.

In one embodiment, the present invention provides compounds of Formula I:

(I)

or a pharmaceutically acceptable salt, hydrate, prodrug, or mixtures thereof, wherein:
m is zero or one;
n is zero or one;
p is one or two;
Y is a direct bond, >C=O, —O—, —N($R_{10}$)—, N, or —C($R_8$)$_p$—;
Z is O, or S;
X is $NR_{11}$, —O—, —S—, $CR_{12}R_{13}$, a bond, —$CR_{12}$=$CR_{13}$—, or —C($R_{12}R_{13}$)C($R_{14}R_{15}$)—;
W is selected from —CN, —C($R_9$)$_2$, —(N($R_9$)$_2$) where the $R_9$ substituents may be combined to form a heteroaryl or $C_3$-$C_8$ cycloalkyl optionally containing at least one hetero atom in place of a carbon atom, —P(O)$_2$—$OR_9$, —P(O)(OR$_9$)$_2$, —S(O)$_2$—$R_9$, —S(O)$_3R_9$, —C(O)—$R_9$, —C(O)—N($R_9$)$_2$, —S(O)$_2NR_9$, $C_3$-$C_8$ cycloakyl optionally containing at least one heteroatom in place of a carbon atom, and heteroaryl;
$R_1$, $R_2$, $R_3$, $R_4$, $R_5$, $R_6$, $R_7$, $R_8$, $R_{12}$, $R_{13}$, $R_{14}$, and $R_{15}$, when present, are independently: hydrogen, lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, $C_5$-$C_7$ cycloalkenyl, lower ($C_1$-$C_4$) alkoxy, aryl, heteroaryl, aralkyl, heteroaralkyl, alkaryl, alkheteroaryl, hydroxy, amino, nitro, halo, nitroso, sulfo, sulfonic acid, or carboxy;
$R_9$ is hydrogen, lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, heteroaralkyl, alkaryl, alkheteroaryl, hydroxy, lower ($C_1$-$C_4$) alcohol, lower ($C_1$-$C_4$) alkoxy, amino, or carboxy; and
$R_{10}$ and $R_{11}$ are independently: hydrogen, lower ($C_1$-$C_9$ straight or branched chain) alkyl, lower ($C_2$-$C_9$ straight or branched chain) alkenyl, aryl, aralkyl, alkaryl, halo, hydroxy, lower ($C_1$-$C_4$) alkoxy, amino, or carboxy;
each $R_{16}$ is independently hydrogen or lower ($C_1$-$C_9$ straight or branched chain) alkyl; and
T, when present, is a divalent or trivalent organic residue independently selected from the group consisting of: lower ($C_2$-$C_9$ straight or branched chain) alkylene, lower alkenylene, arylene, aralkylene, and alkarylene;
wherein one, two or three of the hydrogen atoms of said divalent or trivalent organic residue can be substituted by a moiety selected from the group consisting of: lower ($C_1$-$C_9$ straight or branched chain) alkyl, cycloalkyl, lower ($C_2$-$C_9$ straight or branched chain) alkenyl, cycloalkenyl, aryl, heteroaryl, aralkyl, heteroaryalkyl, alkaryl, alkheteroaryl, halo, trifluoromethyl, hydroxy, lower ($C_1$-$C_4$) alkoxy, amino, nitro, trifluoromethyl, alkenyloxy, phenoxy, and benzyloxy;

wherein one, two, or three carbon atoms in the divalent or trivalent organic residue can be replaced by a hetero-atom-containing-moiety selected from the group consisting of: phenol, phenoxymethyl, phenoxycarbonyl, benzyloxy, —O—, >C=O, —S—, —SO$_2$—, —$NR_1SO_2$—, —SO$_2NR_1$—, —$NR_1$—, and —PO$_2$—;
wherein any of the lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, and alkaryl groups can be independently substituted with one, two or three substituents selected from the group consisting of: lower ($C_1$-$C_9$ straight or branched chain) alkyl, $C_3$-$C_4$ cycloalkyl optionally containing at least one heteroatom in place of a carbon atom, lower ($C_2$-$C_9$ straight or branched chain) alkenyl, cycloalkenyl, aryl, heteroaryl, aralkyl, heteroaralkyl, alkaryl, alkheteroaryl, halo, trifluoromethyl, hydroxy, lower ($C_1$-$C_4$) alkoxy, carboxy (such as methoxy or ethoxy), carbonyl, lower alkyl ester (such as methylester or ethylester), amino, nitro, trifluoromethyl, alkenyloxy, phenoxy, benzyloxy,
wherein one, two, or three carbon atoms of any of the lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, and alkaryl groups can be replaced by a hetero-atom-containing-moiety selected from the group consisting of: —O—, >C=O, —S—, —SO$_2$—, —$NR_1SO_2$—, —SO$_2NR_1$—, N, —$NR_1$—, and —PO$_2$—.
The dotted line between positions 1 and 2 in chemical formulas herein will be recognized to represent a single or double bond.
In another embodiment, the present invention provides compounds of Formula (II)

(II)

or a pharmaceutically acceptable salt, hydrate, prodrug, or mixtures thereof, wherein:
q is zero or one;
Y is N, —CH— or —CH$_2$;
Z is O;
X is —O—, or a bond;
$R_1$, $R_2$, $R_3$, $R_4$, $R_5$, $R_6$, and $R_7$, when present, are independently: hydrogen, lower ($C_1$-$C_9$ straight or branched chain) alkyl, lower ($C_2$-$C_9$ straight or branched chain) alkenyl, $C_3$-$C_8$ cyloalkyl optionally containing at least one heteroatom in place of a carbon atom. $C_5$-C-cycloalkenyl, lower ($C_1$-$C_4$) alkoxy, aryl, heteroaryl, aralkyl, heteroaralkyl, alkaryl, alkheteroarly, hydroxy, amino, nitro, halo, nitroso, or carboxy;
$R_9$ is hydrogen, lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, heteroaralkyl, alkaryl, alkheteroaryl, hydroxy, lower ($C_1$-$C_4$) alcohol, lower ($C_1$-$C_4$) alkoxy, amino, or carboxy; and T, when present, is a divalent or trivalent organic radical independently selected from the group consisting of: lower alkylene, lower alkenylene, $C_2$-$C_4$ alkenyloxy, arylene, aralkylene, and alkarylene;

wherein one, two or three of the hydrogen atoms of said divalent or trivalent organic radical can be substituted by a moiety selected from the group consisting of lower ($C_1$-$C_9$ straight or branched chain) alkyl, lower ($C_2$-$C_9$ straight or branched chain) alkenyl, aryl, aralkyl, alkaryl, halo, trifluoromethyl, hydroxy, lower ($C_1$-$C_4$) alkoxy, amino, nitro, trifluoromethyl, alkenyloxy, phenoxy, and benzyloxy;

wherein one, two, or three carbon atoms in the divalent or trivalent organic radical can be replaced by a hetero-atom-containing-moiety selected from the group consisting of: phenoxy, phenoxycarbonyl, benzyloxy, —O—, >C=O, —S—, —$SO_2$—, —$NR_1SO_2$—, —$SO_2NR_1$—, —$NR_1$—, and —$PO_2$—;

wherein the lower alkyl, cyloalkyl optionally containing at least one heteroatom, lower ($C_2$-$C_9$ straight or branched chain) alkenyl, aryl, heteroaryl, aralkyl, heteroaralkyl, alkaryl, and alkheteroaryl groups can be independently substituted with one, two or three substituents selected from the group consisting of: lower ($C_1$-$C_9$ straight or branched chain) alkyl, $C_3$-$C_8$ cycolalkyl optionally containing at least one heteratom, lower ($C_2$-$C_9$ straight or branched chain) alkenyl, aryl, heteroaryl, aralkyl, heteroaralkyl, alkaryl, alkheteroaryl, halo, trifluoromethyl, hydroxy lower ($C_1$-$C_4$) alkoxy, carboxy (such as methoxy or ethoxy), carbonyl, lower alkyl ester (such as methylester or ethylester), amino, nitro, trifluoromethyl, alkenyloxy, phenoxy, benzyloxy, wherein one, two, or three carbon atoms thereof can be replaced by a hetero-atom-containing-moiety selected from the group consisting of: —O—, >C=O, —S—, —$SO_2$—, —$NR_1SO_2$—, —$SO_2NR_1$—, N, —$NR_1$—, and —$PO_2$—.

In a further embodiment, the present invention provides compounds of Formula (III)

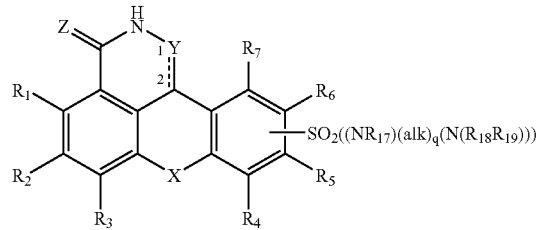

(III)

wherein
Z and X are oxygen;
q is zero or one;
"alk" is lower alkylene;
$R_1$—, $R_{18}$ and $R_{19}$ are independently hydrogen or lower alkyl; or
$R_{17}$ and $R_{18}$ or $R_{18}$ and $R_{19}$ taken together can be a lower alkylene to form a heterocyclic ring; and
$R_1$, $R_2$, $R_3$, $R_4$, $R_5$, $R_6$ and $R_7$ are independently: hydrogen, lower ($C_1$-$C_9$ straight or branched chain) alkyl, $C_3$-$C_8$ cycloalkyl optionally containing at least one hetero atom, lower ($C_2$-$C_9$ straight or branched chain) alkenyl, lower ($C_1$-$C_4$) alkoxy, aryl, heteroaryl, aralkyl, heteroaralkyl, alkaryl, alkheteroaryl, hydroxy, amino, nitro, halo, nitroso, or carboxy.

In yet a further embodiment the present invention provides compounds of Formulas (IV) and (V)

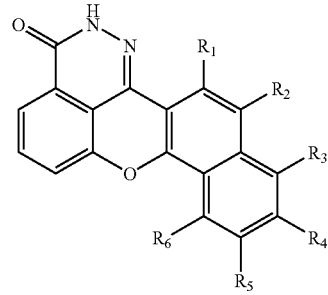

(IV)

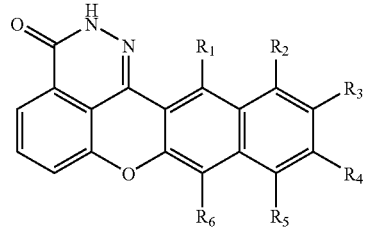

(V)

wherein $R_1$-$R_6$ are as defined above. Preferably, $R_1$-$R_6$ are each independently any of hydrogen, methyl, ethyl, propyl, isopropyl, butyl, isobutyl, hydroxyl, amino, nitro, nitroso, carboxy, trifluoromethyl, phenoxy, and benzyloxy.

Preferred embodiments of the present invention include compounds wherein X and Z are oxygen and Y is nitrogen. The preferred forms of the following specific embodiments include, but are not limited to, compounds wherein X and Z are oxygen and Y is nitrogen.

Preferred embodiments of the present invention include compounds wherein each of V is —CN, m and n are zero and p is one. Of these, further preferred embodiments include compounds where T is —$CH_2$—, Z and X are oxygen, Y is N and $R_1$ to $R_7$ are hydrogen. Preferably, each of T is —$CH_2$—, Z and X are oxygen and Y is N Further preferred embodiments of the present invention include compounds wvhere each of W is —$(N(R_9)_2)$, preferably W is —$N(R_9)_2$, m and n are zero and p is one, X is preferably oxygen or a bond, Z is oxygen and Y is nitrogen. Of these, preferred embodiments include those compounds where each $R_9$ is independently selected from hydrogen, methyl, ethyl, propyl, isopropyl, butyl, isobutyl, pentyl, isopentyl, methoxy, ethoxy or amino or where the $R_9$ substituents combine with the N to form a 5- or 6-membered substituted or unsubstituted heterocycloalkyl, optionally subsituted with an additional oxygen or nitrogen, or combine with the N to form a 5- or 6-membered substituted or unsubstituted heteroaryl. The substitutions of these preferred embodiments preferably including methyl, ethyl, propyl, isopropyl, butyl, isobutyl, methylester, ethylester, benzyl, phenyl, benzoxy, phenoxy, phenoxycarbonyl, one or two additional heterocycloalkyls or heteroaryl rings and/or one or two fused benzene rings. Preferred forms of this embodiment include compounds where T is absent, —$CH_2$— or —$CH_2$—$CH_2$—$CH_2$S, $CH_2SCH_2$, $CH_2SCH_2CH_2$, methoxy or phenoxymethyl. Particularly preferred forms of this embodiment include compounds wherein $R_9$ substituents combine, with the N of W, to form a

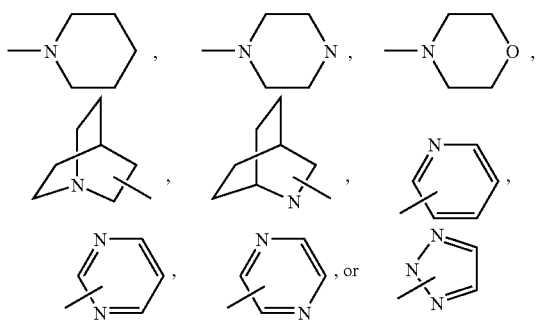

group, which may be optionally substituted by the above-noted substitutions, such as, for example, pyridyl, benzyl, phenyl methyl ester or ethyl ester, and/or fused with 1-2 additional benzene rings.

In a further preferred embodiment of the present invention, each of W is —N($R_9$)$_2$, m is one and n is one, X is oxygen or a bond, Z is oxygen and Y is nitrogen. Of these, prefered embodiments include those compounde where each $R_9$ is independently selected from hydrogen, methyl, ethyl, propyl, isopropyl, butyl, isobutyl, mehanol, ethanol, methoxy, ethoxy or amino or where the $R_9$ substituents combine with the N to form a 5- or 6-membered substituted or unsubstituted heterocycloalkyl, optionally subsituted with an additional oxygen or nitrogen, or combine with the N to form a 5- or 6-membered substituted or unsubstituted heteroaryl. The substitutions of these preferred embodiments preferably including methyl, ethyl, propyl, isopropyl, butyl, isobutyl, methyl ester, ethyl ester, benzyl, phenyl, benzoxy, phenoxy, phenoxycarbonyl and pyridyl. Preferred forms of this embodiment include compounds where T is absent, —$CH_2$— or —$CH_2$—$CH_2$—. Particularly preferred forms of this embodiment includes compounds wherein $R_9$ substituents form with the N of W to form a

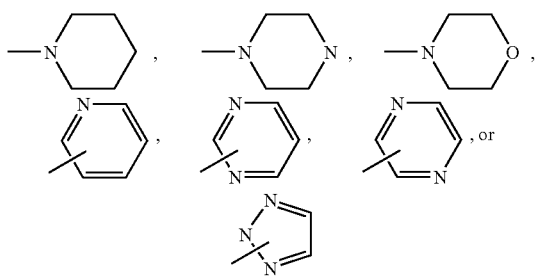

group, which may be optionally substituted by pyridyl, benzyl or phenyl and/or fused with 1-2 additional benzene rings. $R_1$-$R_7$ are preferably hydrogen.

Other preferred embodiments of the present invention includes compounds wherein W is either —P(O)$_2$—O$R_9$ or —P(O)(O$R_9$)$_2$, m is zero and p is one. Of these, each $R_9$ is preferably independently hydrogen, methyl, ethyl, propyl, isopropyl, butyl or isobutyl. Preferably, in these embodiments, Y is nitrogen, Z is oxygen and X is oxygen. Preferably, m is zero and when n is one, $R_{16}$ is preferably hydrogen, T is preferably —$CH_2$— or —$CH_2CH_2$— in these preferred embodiments.

Further preferred embodiments of the present invention include compounds wherein W is either —S(O)$_2$—$R_9$, —S(O)$_2$—$R_9$ or —S(O)$_2$N$R_9$, m is zero and p is 1. Of these, preferred embodiments include where $R_9$ is hydrogen, or substituted or unsubstituted methyl, ethyl, propyl, isopropyl, butyl or isobutyl, wherein the optional substitution is a 5- or 6-membered cycloalkyl, optionally subsituted with at least one oxygen or nitrogen or a 5- or 6-membered heteroaryl. Further preferred forms of these embodiments include compounds where X is oxygen or a bond, Z is oxygen, T is absent or —$CH_2$—, $R_1$-$R_7$ are hydrogen, Y is nitrogen and $R_9$ is hydrogen, methyl, ethyl, propyl, isopropyl, butyl, isobutyl, benzyl, benzylcarbonyl, phenyl.

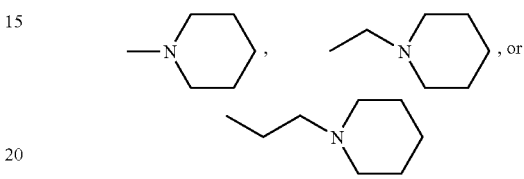

Preferably, $R_9$ is hydrogen, methyl, ethyl, propyl, isopropyl, butyl, isobutyl, benzyl, or benzylcarbonyl.

Further preferred embodiments of the present invention include compounds wherein W is either —C(O)—$R_9$ or —C(O)N($R_9$), and m is zero Preferably, n=1 when W is C(O)$R_9$. Of these, preferred embodiments include compounds where each $R_9$ is independently hydrogen, methyl, ethyl, propyl, isopropyl, butyl, isobutyl, hydroxyl, methanol, ethanol, —(CH(OQ))$_p$COOH (where Q is hydrogen, hydroxyl, ethoxy or methoxy), or amino, and T is (—$CH_2$—)$_{1-4}$, wherein optionally one of the methenyl units is replace with phenoxy, carbonyl or oxygen. Prefered forms of these embodiments include compounds where X is oxygen or a bond, Z is oxygen, Y is nitrogen and $R_1$ to $R_7$ are hydrogen, $R_{16}$, when present is preferably hydrogen.

Further preferred embodiments of the present invention include compounds wherein W is an optionally substituted 5- or 6-membered cycloalkyl optionally containing at least one heteroatom selected from S, O or N, or a heteroaryl, wherein the cycloakyl or heteraryl may be substituted or attached to a further 5- or 6-membered cycloalkyl which may optionally contain at least one heteroatom, a 5- or 6-membered heteraryl or a 5- or 6-membered aryl.

Preferably, the compounds of the invention exhibit an IC$_{50}$ for inhibiting PARP in vitro, as measured by the methods described herein, of about 20 μM or less, preferably less than about 10 μM, more preferably less than about 1 μM, most preferably less than about 0.1 μM.

Preferred embodiments of the present invention include the following compounds, and neutral forms thereof, where appropriate.

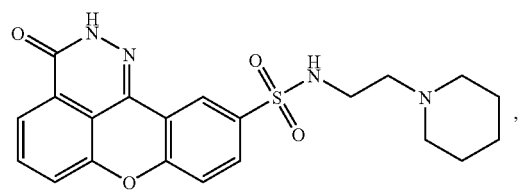

-continued
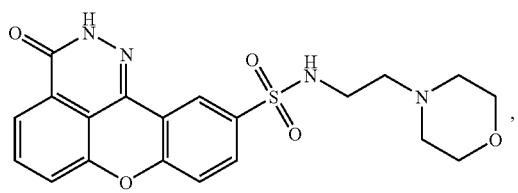
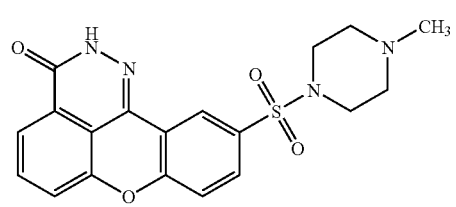
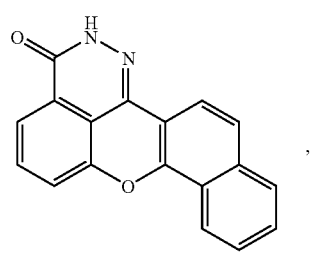
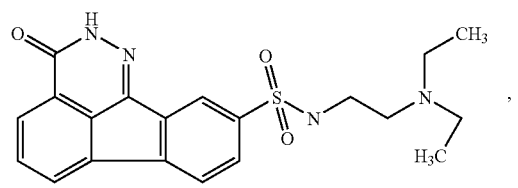
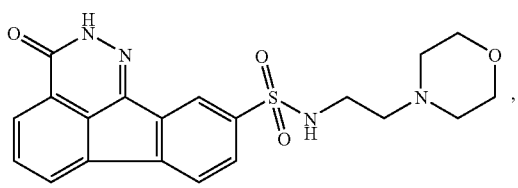
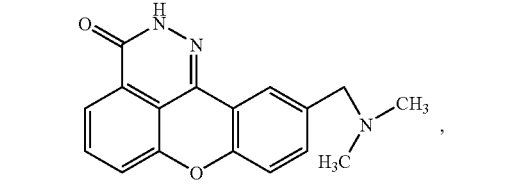
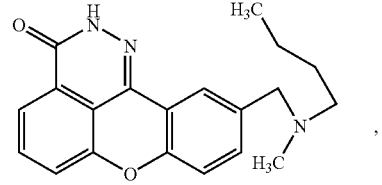
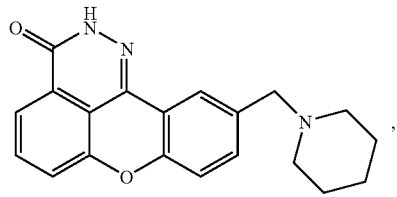
-continued
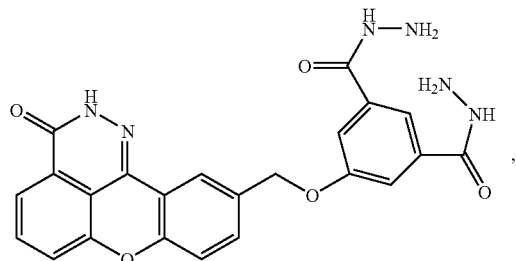
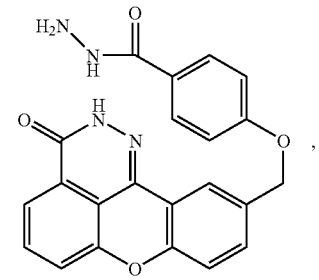
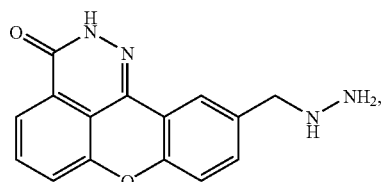
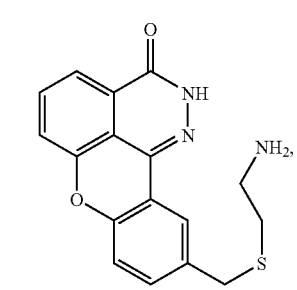
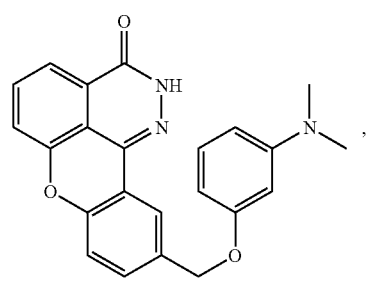
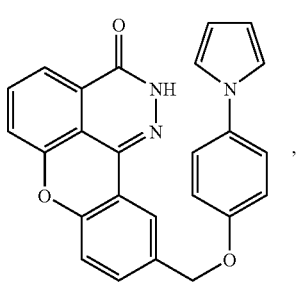

-continued
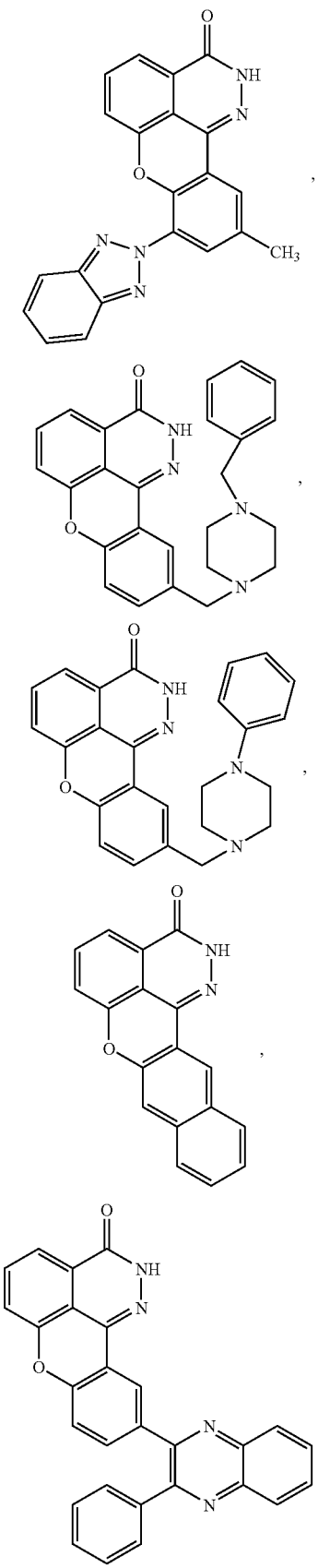
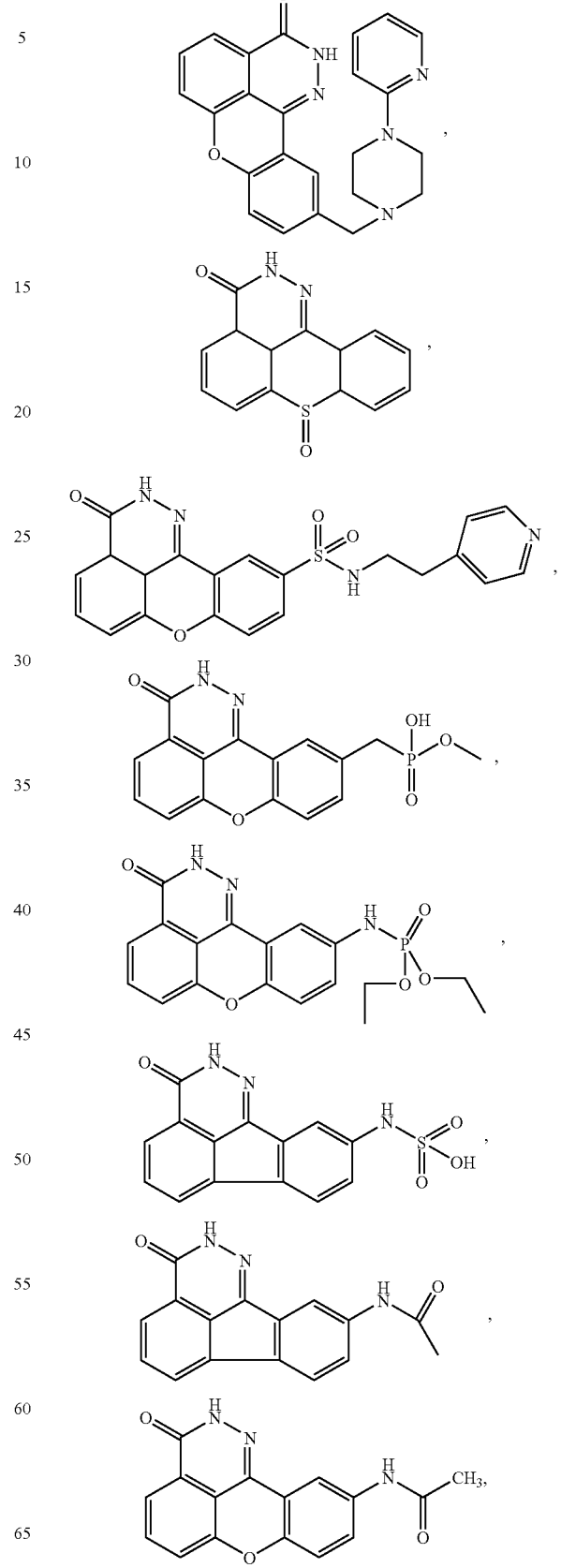

-continued
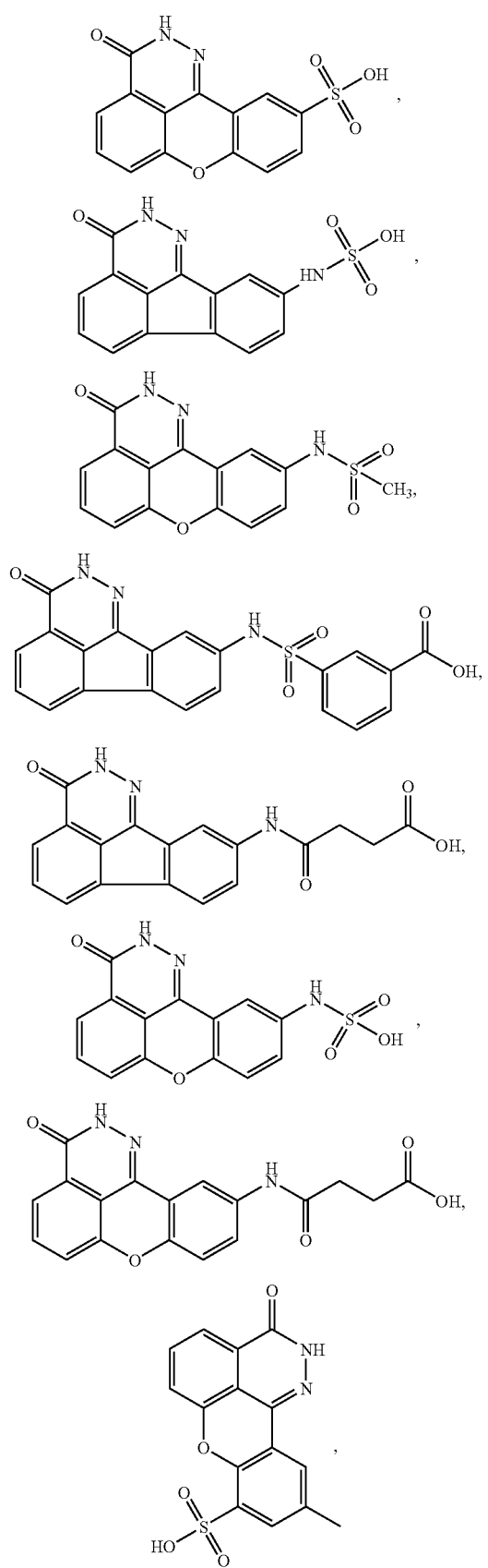
-continued
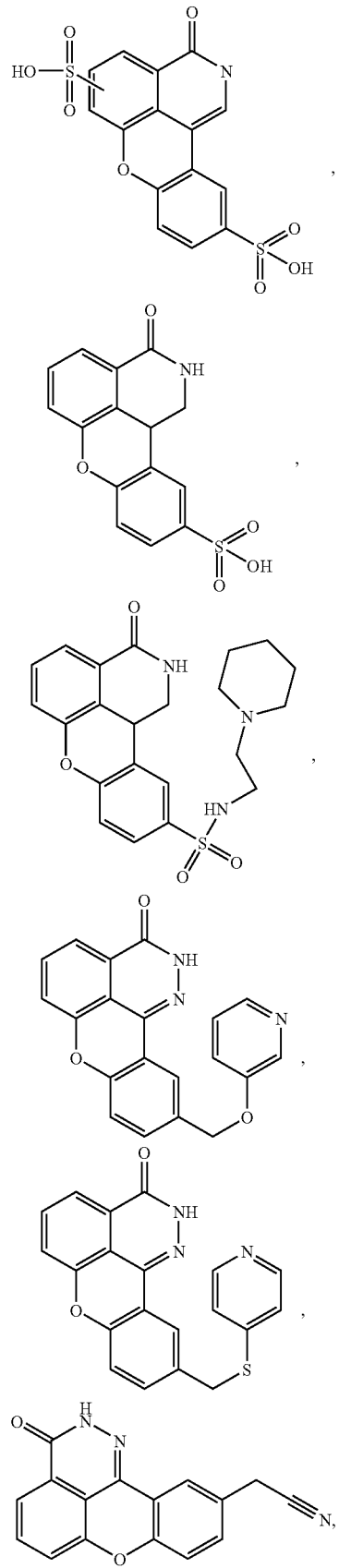

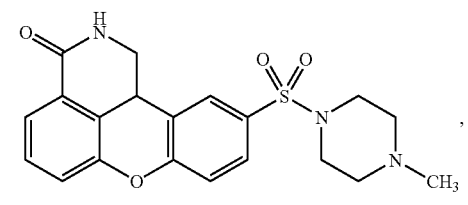,
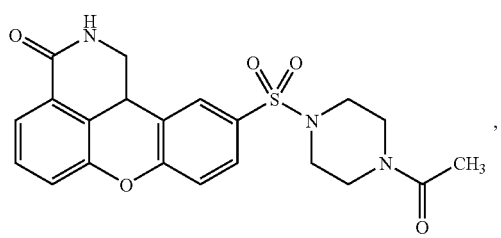,
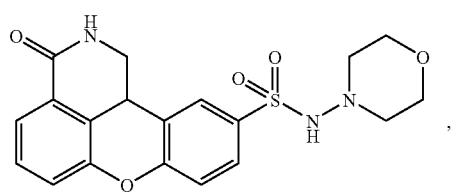,
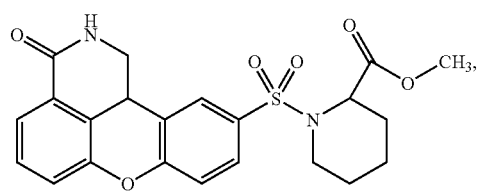,
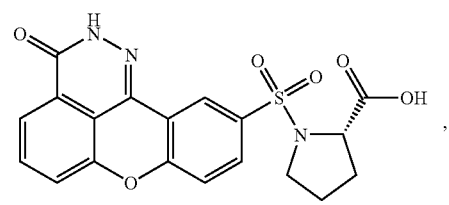,
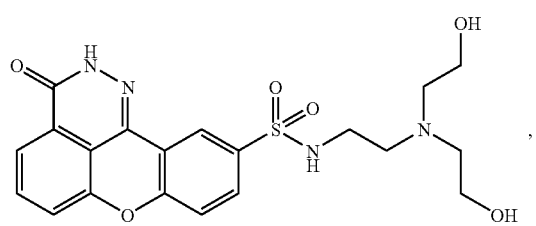,
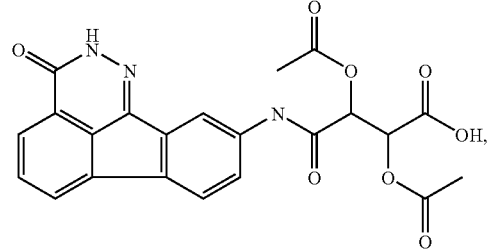,
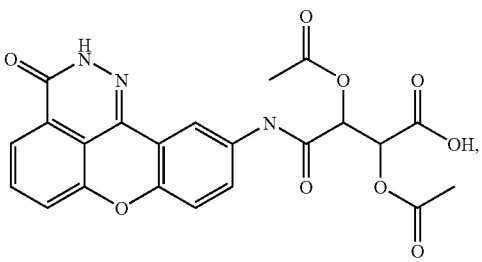,
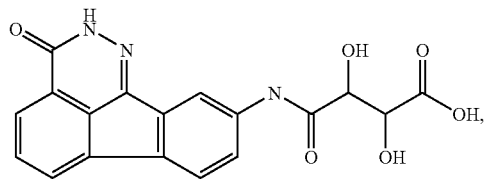,
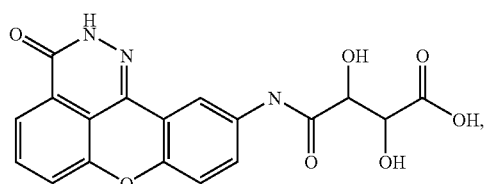,
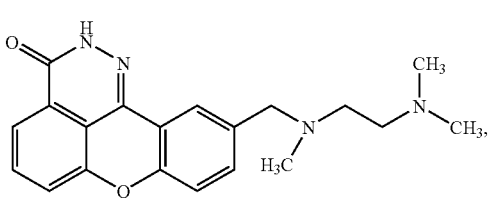,
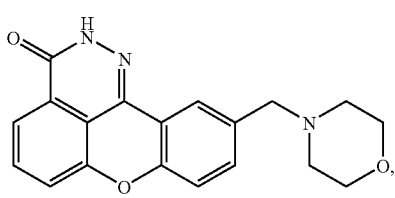,
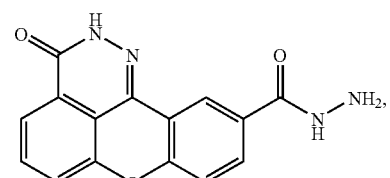,
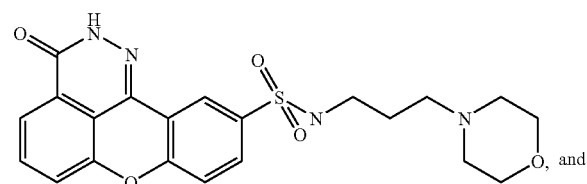 and
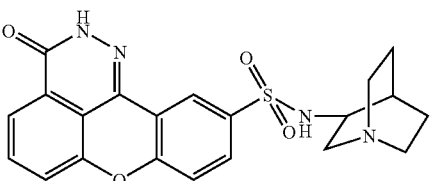.

Broadly, the compounds and compositions of the present invention can be used to treat or prevent cell damage or death due to necrosis or apoptosis, cerebral ischemia and reperfusion injury or neurodegenerative diseases in an animal, such as a human. The compounds and compositions of the present invention can be used to extend the lifespan and proliferative capacity of cells and thus can be used to treat or prevent diseases associated therewith; they alter gene expression of senescent cells; and they radiosensitize hypoxic tumor cells. Preferably, the compounds and compositons of the invention can be used to treat or prevent tissue damage resulting from cell damage or death due to necrosis or apoptosis, and/or effect neuronal activity, either mediated or not mediated by NMDA toxicity. The compounds of the present invention are not limited to being useful in treating glutamate mediated neurotoxicity and/or NO-mediated biological pathways. Further, the compounds of the invention can be used to treat or prevent other tissue damage related to PARP activation, as described herein.

The present invention provides compounds which inhibit the in vitro and/or in vivo polymerase activity of poly(ADP-ribose) polymerase (PARP), and compositions containing the disclosed compounds.

The present invention provides methods to inhibit, limit and/or control the in vitro and/or in vivo polymerase activity of poly(ADP-ribose) polymerase (PARP) in any of solutions, cells, tissues, organs or organ systems. In one embodiment, the present invention provides methods of limiting or inhibiting PARP activity in a mammal, such as a human, either locally or systemically.

The present invention provides methods to treat and/or prevent diseases, syndromes and/or conditions exacerbated by or involving the increased generation of PARP. These methods involve application or administration of the compounds of the present invention to cells, tissues, organs or organ systems of a person in need of such treatment or prevention.

In one embodiment, the present invention provides methods to treat and/or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse and these methods involve administration of the compounds and compositions of the present invention preferably prior to, or immediately subsequent to reperfusion, such that reperfusion injury is prevented, treated or reduced. The present invention also provides methods of preventing and/or treating vascular stroke, cardiovascular disorders In another embodiment, the present invention provides in vitro or in vivo methods to extend or increase the lifespan and/or proliferation capacity of cells and thus also methods to treat and/or prevent diseases associated therewith and induced or exacerbated by cellular senescence including skin aging, atherosclerosis, osteoarthritis, osteoporosis, muscular dystrophy, degenerative diseases of skeletal mnuscle involving replicative senescence, age-related muscular degeneration, immune senescence, AIDS and other immune senescence diseases, and other diseases associated with cellular senescence and aging, as well as to alter the gene expression of senescent cells.

In a further embodiment, the present invention provides methods of treating or preventing or ameliorating the effect of cancer and/or to radiosensitize hypoxic tumor cells to render the tumor cells more susceptible to radiation therapy and thereby to prevent the tumor cells from recovering from potentially lethal damage of DNA after radiation therapy. A method of this embodiment is directed to specifically and preferentially radiosensitizing tumor cells rendering the tumor cells more susceptible to radiation therapy than non-tumor cells.

In yet another embodiment the present invention provides methods of preventing and/or treating vascular stroke, cardiovascular disorders; to treat other conditions and/or disorders such as age-related muscular degeneration. AIDS and other immune senescence diseases, arthritis, atherosclerosis, cachexia, cancer, degenerative diseases of skeletal muscle involving replicative senescence, diabetes, head trauma, spinal chord injury, immune senescence, inflammatory bowel disorders (such as colitis and Crohn's disease), acute pancreatitis, mucositis, hemorrhagic shock, splanchnic arter occlusion shock, multiple organ failure (such as involving any of the kidney, liver, renal, pulmonary, retianl, pancreatic and/or skeletal muscles systems), acute autoimmune thyroiditis, muscular dvstrophy, osteoarthritis, osteoporosis, chronic and/or acute pain (such as neuropathic pain), renal failure, retinal ischemia, septic shock (such as endotoxic shock), local and/or remote entothelial cell dysfunction (such are recognized by endo-dependent relaxant responses and up-regulation of adhesion molecules), inflammation and skin aging.

In one embodiment of the present invention, a person diagnosed wvith acute retinal ischemia or acute vascular stroke is immediately administered parenterally, either by intermittent or continuous intravenous administration, a compound of any of formulas I, II, III, IV or V either as a single dose or a series of divided doses of the compound. After this initial treatment, and depending on the person's presenting neurological symptoms, the person optionally may receive the same or a different compound of the invention in the form of another parenteral dose. The compound of the invention can be admnistered by intermittent or continuous administration via implantation of a biocompatible, biodegradable polymeric matrix deliven system containing a compound of formula I, II, III, IV or V, or via a subdural pump inserted to administer the compound directly to the infarct area of the brain.

In a further embodiment the present invention provides methods to extend the lifespan and proliferative capacity of cells, such as, for example, in using the compounds of the invention as general mediators in the generation of oxidants, proinflammatory mediators and/or cytokines, and/or general mediators of leukocyte infiltration, calcium ion overload, phospholipid peroxidaion, impaired nitric oxide metabolism and/or reduced ATP production

DETAILED DESCRIPTION OF THE INVENTION

Figure 1:
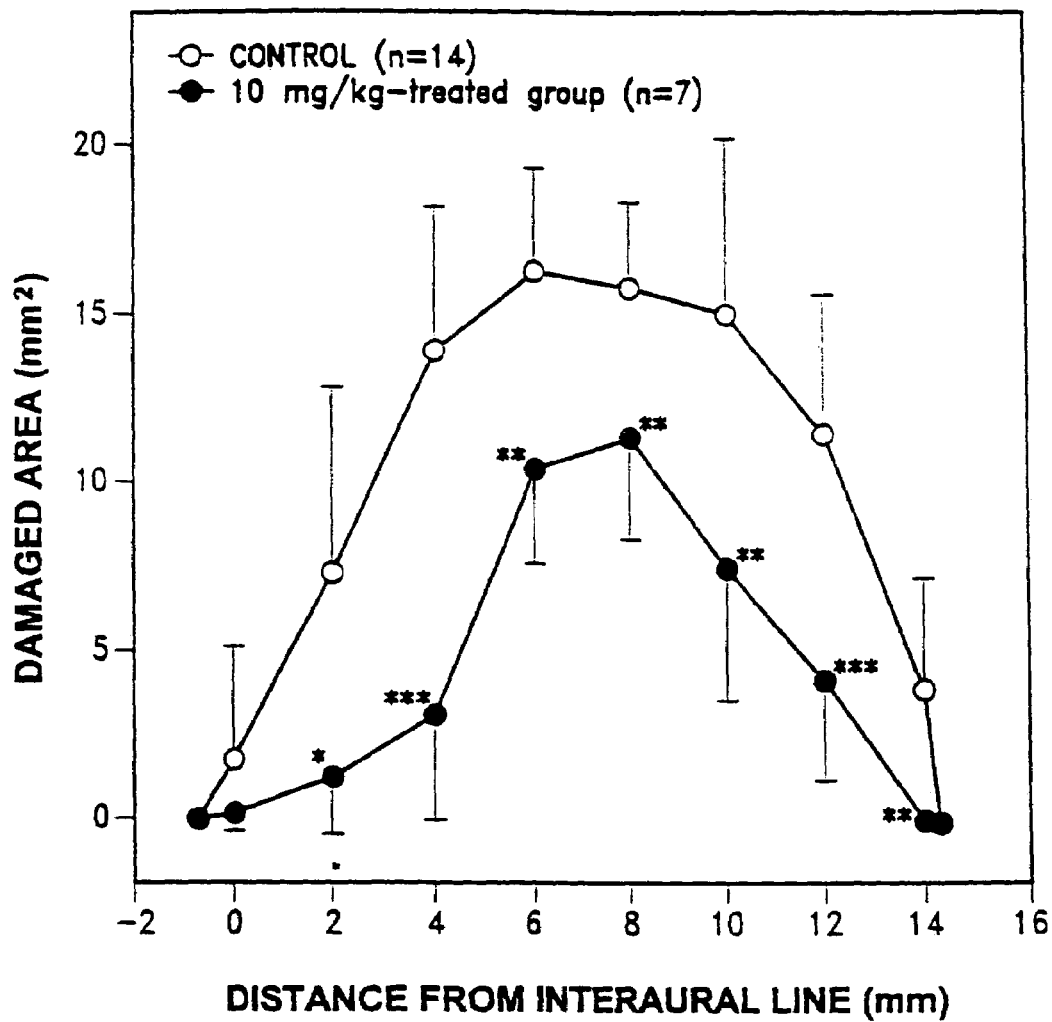
FIG. 1. Shows the distribution of the cross-sectional infarct area at representative levels along the rostrocaudal axis, as measured from the interaural line in non-treated animals and in animals treated with 10 mg/kg of 3,4-dihydro-5-1-(1-piperidinyl)-botoxyl]-1(2H)-isoquinolinone.

The present invention pertains to compounds, pharmaceutical compositions containing the same, methods of using the same, and process of making the same, wherein such compounds are useful as inhibitors of poly(ADP-ribose)

polymerase (PAPP). As such, they treat or prevent neural tissue damage resulting from cell damage or death due to necrosis or apoptosis, cerebral ischemia and reperfusion injury or neurodegenerative diseases in an animal; they extend the lifespan and proliferative capacity of cells and thus can be used to treat or prevent diseases associated therewith, they alter gene expression of senescent cells; and they radiosensitize hypoxic tumor cells. Preferably, the compounds of the invention treat or prevent tissue damage resulting from cell damage or death due to necrosis or apoptosis, and/or effect neuronal activity, either mediated or not mediated by NMDA toxicity. These compounds are thought to interfere with more than the glutamate neurotoxicity and NO-mediated biological pathsways. Further, the compounds of the invention can treat or prevent other tissue damage related to PARP activation.

For example, the compounds of the invention can treat or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse.

The compounds of the present invention can also be used to extend or increase the lifespan or proliferation of cells and thus to treat or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related muscular degeneration, immune senescence. AIDS and other immune senescence diseases, and other diseases associated with cellular senescence and aging, as well as to alter the gene expression of senescent cells. These compounds can also be used to treat cancer and to radiosensitize hypoxic tumor cells to render the tumor cells more susceptible to radiation therapy and to prevent the tumor cells from recovering from potentially lethal damage of DNA after radiation therapy, presumably their ability to prevent DNA repair. The compounds of the present invention can be used to prevent or treat vascular stroke; to treat or prevent cardiovascular disorders; to treat other conditions and/or disorders such as age-related muscular degeneration, AIDS and other immune senescence diseases, arthritis, atherosclerosis, cachexia cancer, degenerative diseases of skeletal muscle involving replicative senescence, diabetes, head trauma, immune senescence, inflammatory bowel disorders (such as colitis and Crohn's disease), muscular dystrophy, osteoarthitis, osteoporosis, chronic and/or acute pain (such as neuropathic pain), renal failure, retinal ischemia, septic shock (such as endotoxic shock), and skin aging.

Preferably, the compounds of the invention act as PARP inhibitors to treat or prevent tissue damage resulting from cell death or damage due to necrosis or apoptosis; to treat or prevent neural tissue damage resulting from cerebral ischemia and reperfusion injury or neurodegenerative diseases in an animal; to extend and increase the lifespan and proliferative capacity of cells; to alter gene expression of senescent cells; and to radiosensitize tumor cells.

Another especially preferred embodiment of the invention is a pharmacutical composition which comprises (i) a therapeutically effective amount of the compound of formula I, II or III; and (ii) a pharmaceutically acceptable carrier.

As used herein, "alkyl" means a branched or unbranched saturated hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentl, n-hexyl, and the like, unless otherwise indicated.

"Alkenyl" means a branched or unbranched unsaturated hydrocarbon chain comprising a designated number of carbon atoms. For example, $C_2$-$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR wherein R is alkyl as herein defined. Preferably, R is a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless othenwise indicated.

"Amino" compounds include amine ($NH_2$) as well as substituted amino groups comprising alkyls of one through six carbons.

"Ar", "aryl" or "heteroaryl" means a moiety which is substituted or unsubstituted, especially a cyclic or fused cyclic ring and includes a mono-, bi-, or tricyclic, carbo- or heterocyclic ring, wherein the ring is either unsubstituted or substituted in one to five position(s) with halo, haloalkyl, hydroxyl, nitro, trifluoromethyl, $C_1$-$C_6$ straight or branched chain alkyl, $C_2$-$C_6$ straight or branched chain alkenyl. $C_1$-$C_6$ alkoxy, $C_1$-$C_6$ alkenyloxy, phenoxy, benzyloxy, amino, thiocarbonyl, ester, thioester, cyano, imino, alklainino, aminoalkyl, sulfhydryl, thioalkyl, and sulfonyl; wherein the individual ring sizes are preferably 5-8 members; wherein the heterocyclic ring contains 1-4 heteroatom(s) selected from the group consisting of O, N, or S; wherein aromatic or tertiary alkyl amines are optionally oxidized to a corresponding N-oxide. Heteroaryls may be attached to other rings or substituted through the heteroatom and/or carbon atom of the ring. Particularly preferred aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstiruted or multi-substituted with substituents selected from the group consisting of amino, trifluoromethyl, $C_1$-$C_6$ straight or branched chain alkyl, $C_2$-$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, ($C_1$-$C_6$)-straight or branched chain alkyl, ($C_3$-$C_6$) straight or branched chain alkenyl or alkynyl, and ($C_1$-$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

Cycloalkyl optionally containing at least one heteroatom includes saturated $C_3$-$C_8$ rings, preferably $C_5$ or $C_6$ rings, wherein at 14 heteroatoms selected from O, N or S may be optionally substituted for a carbon atom of the ring. Cycloalkyls optionally containing at least one heteroatom, as described above, may be substituted by or fused to at least one 5 or 6 membered aryl or heteroaryl. Prefered cycloalkyls containing a heteroatom include pyrrolidinyl, imidazolidinyl, pyrazolidinyl, piperidinyl, piperazinyl, morpholino and thiomorpholino.

The compounds of the present invention possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of any of formulas I, II, III, IV and V. It is understood that the individual stereoisomers as well as mixtures (racemic and non-racemic) of stereoisomers are encompassed by the scope of the present invention. The S-stereoisomer at atom 1 of formula (I) is most preferred due to its greater activity.

"Isomers" are different compounds that have the same molecular formula and includes cyclic isomers such as (iso)indole and other isomeric forms of cyclic moieties. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The compounds of the invention are useful in a free base form, in the form of pharmaceutically acceptable salts, pharmaceutically acceptable hydrates, pharmaccutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound. "Pharmaceutically acceptable salt", "hydrate", "ester" or "solvate" refers to a salt, hyydrate, ester, or solvate of the inventive compounds which possesses the desired pharmacological activity and which is neither biologically nor otlienwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylantine, triethylamine and dicyclohexylamine, mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," J. Pharm. Sci., 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solyates of the basic compounds may be prepared either by dissolving the free base of a PARP inhibitor of the present invention in an aqueous or an aqueous alcohol solution or other suitable solyent containing the appropriate acid or base, and isolating the salt by evaporating the solution. Alternatively, the free base of the PARP inhibitor of the present invention can be reacted with an acid, as well as reacting the PARP inhibitor having an acid group thereon with a base, such that the reactions are in an organic solyent, in which case the salt separates directly or can be obtained by concentrating the solution, "Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1. pp. 172-178, 949-982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since most drugs undergo metabolic transformation of some kind, the biochemical reactions that play a role in drug metabolism may be numerous and diverse. The main site of drug metabolism is the liver, although other tissues may also participate.

The term "neurodegenerative diseases" includes Alzheimer's disease. Parkinson's disease and Huntington's disease.

The term "nenrous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent neurodegeneration in patients diagnosed as having a neurodegenerative disease or who are at risk of developing a neurodegenerative disease. The term also encompasses preventing further neurodegeneration in patients who are already suffering from or have symptoms of a neurodegenerative disease.

The term "treating" refers to:

(i) preventing a disease, disorder or condition from occurring in an animal that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

The term "neural tissue damage resulting from ischemia and reperfusion injury and neurodegenerative diseases" includes neurotoxicity, such as seen in vascular stroke and global and focal ischemia.

A feature characteristic of many of these transformations is that the metabolic products are more polar than the parent drugs, although a polar drug does sometimes yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are each transformed within the body to a more polar and more effective metabolite, p-hydroxyacetanilid (acetaminophen), which is widely used today. When a dose of acetanilid is given to a person, the successive metabolites peak and decay in the plasma sequentially. During the first hour, acetanilid is the principal plasma component. In the second hour, as the acetanilid level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

The reactions involved in drug metabolism are often classified into two groups, as shown in the Table II. Phase I (or functionalization) reactions generally consist of (I) oxidative and reductive reactions that alter and create new functional groups and (2) hldrolytic reactions that cleave esters and amides to release masked functional groups. These changes are usually in the direction of increased polarity.

Phase II reactions are conjugation reactions in which the drug, or often a metabolite of the drug, is coupled to an endogenous substrate, such as glucuronic acid, acetic acid, or sulfuric acid.

TABLE II

Phase I Reactions (functionalization reactions):
(1) Oxidation via the hepatic microsomal P450 system:

Aliphatic oxidation
Aromatic hydroxylation
N-Dealkylation
O-Dealkylation
S-Dealkylation
Epoxidation
Oxidative deamination
Sulfoxide formation
Desulfuration
N-Oxidation and N-hydroxylation
Dehalogenation
(2) Oxidation via nonmicrosomal mechanisms:

Alcohol and aldehyde oxidation
Purine oxidation
Oxidative deamination (monoamine oxidase and diamine oxidase)
(3) Reduction:

Azo and nitro reduction
(4) Hydrolysis:

Ester and amide hydrolysis
Peptide bond hydrolysis
Epoxide hydration
Phase II Reactions (conjugation reactions):

(1) Glucuronidation
(2) Acetylation
(3) Mercapturic acid formation
(4) Sulfate conjugation
(5) N-, O-, and S-methylation
(6) Trans-sulfuration The compounds of the present invention exhibit pharmacological activity and are, therefore, useful as pharmaceuticals. In particular, the compounds exhibit central nervous and cardiac vesicular system activity.

It is understood that tautomeric forms, when possible, are included in the invention. For example, the tautomeric forms of the following compounds are exemplary:

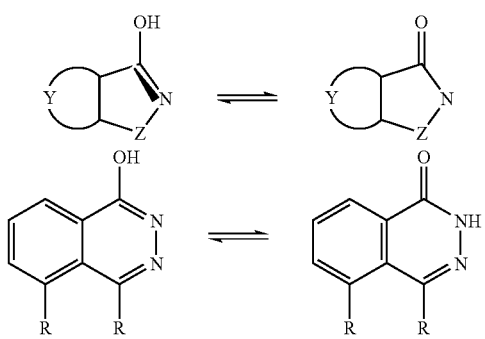

Many of the PARP inhibitors are known and thus, can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly(ADP-ribose) Polymerase", Anticancer Drug Des., 6:107-17 (1991), which discloses processes for synthesizing a number of different PARP inhibitors.

Typically, the PARP inhibitors used in the composition of the invention will have an $IC_{50}$ for inhibiting poly(ADP-ribose) polymerase in vitro of about 20 μM or less, preferably less than about 10 μM, more preferably less than about 1 μM, most preferably less than about 0.1 μM.

The PARP inhibitor 3,4dihydro-5-[4-(1-piperidinyl)butoxy]-1(2H)-isoquinolinone, for example, has been reported to inhibit PARP with an $IC_{50}$ of 40 nM by Suto et al., cited above.

There are multiple routes which may be undertaken to prepare the compounds of the present invention. Two of these routes for the preparation of the xanthene derivatives of this invention are demonstrated below by schemes 1-3 and 4-7.

The xanthene ring may be generically substituted as set forth in formula I. Such xanthene starting derivatives are known in the chemistry literary and are accessible by processes known to one skilled in the art. The process sequence set forth herein does not present an exact sequence of reactions by which the compound must be made; that is, the sequence of reactions can be rearranged in several ways to reach the target molecule.

DETAILED DESCRIPTION OF PREFERRED EMBODIMENTS

The xanthene and thioxanthene derivatives of this invention are represented by previously defined formulas I-V. As an example, the xanthene derivatives of this invention can be prepared in a conventional manner as illustrated below by Schemes 1-5. The xanthene ring may be generically substituted as set forth in formula I. Such xanthene starting derivatives are known in the chemistry literature and accessible by processes known to one skilled in the art. The process sequence set forth herein does not present an exact sequence of reactions by which the compound must be made; that is, the sequence of reactions can be rearranged in several ways to reach the target molecule. Scheme 1 below illustrates schematically the preparation of compounds Example 1 through Examples 4.

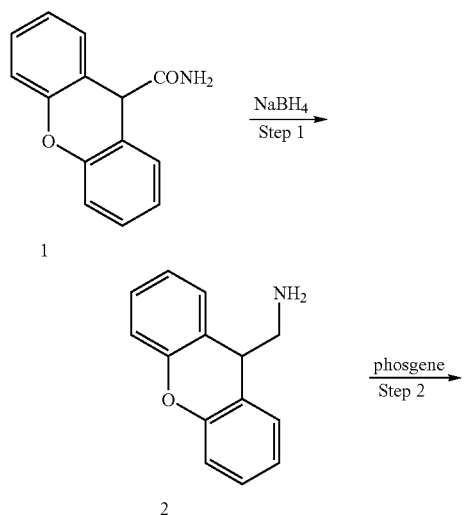

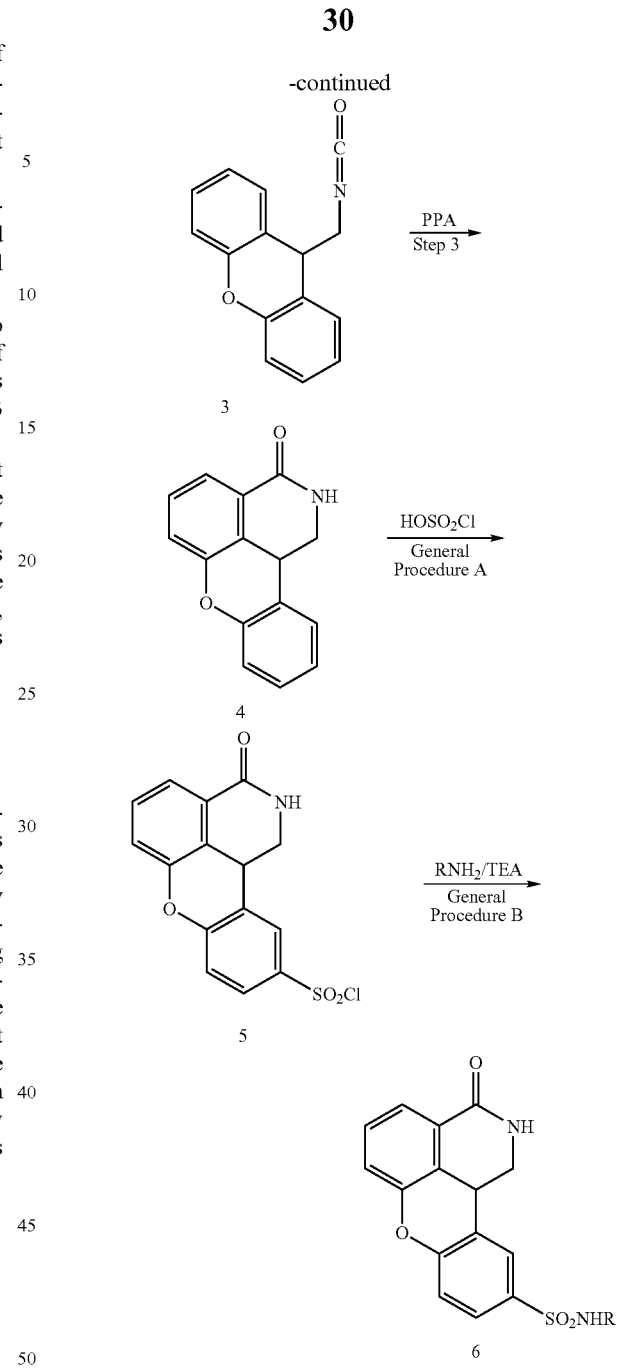

Step 1

9-Aminomehtylxanthene 2 is available by reduction of 9-carboxamide 1 using sodium boronhydride in dioxane. Other reduction methods can be substituted include lithium aluminum hydride and other boronhydrides. The solvent can also be varied. DMSO, tetrahydrofuran, diethylether and other organic solvent can be used. The temperature of the reaction is general between 0° C. and 200° C. For example, 9-aminomethylxanthene can be made as follows: To a stirred suspension of sodium boronhydride (1.89 g, 50 mmol) and 9-xanthenecarboxamide (2.25 g, 10 mmol) in dioxane (20 ml) is added acetic acid (3.0 g, 50 mmol) in dioxane (10 mL) over a period of 10 minutes at 10° C. The reaction mixture is stirred at reflux for 2 hours and concentrated to dryness in vacuo. The excess reductive reagent is decomposed with water and the mixture is extracted with chloroform. The chloroform layer is washed wvith water, dried over anhydrous sodium sulfate and evaporated in vacuo. The residue is purified by silica gel column chromatography (ethylacetate:methanol, 9:1 as eluant) to give a white solid (1.6 g, 7.6 mmol) in 76.2% yield.

Step 2

The 9-isocyanomehtylxanthenes 3 is obtained by condensation of the amino group with phosgene in a heated solution of toluene. Other solvents, such as p-nitrobenzene, can also be used. The new formed isocyano functionality serves as an electrophile for intermolecular Friedle-Crafts reaction in next step. Other functionalities include N-carbonylimidazole, N-carbonylbenzotriazole and N-ethylformate can also be applied in this type of reactions. These functionalities can be formed by reactions of the 9-aminomethylxanthenes 2 with carbonyldiimidazole, carbonyldibenzotrazole and ethyl chloroformate respectively.

Step 3

The desired xanthane product, 3,4-dihydrobenzopyrano[4,3,2-de]isoquinoli-1-one 4 can be obtained by an intramolecular Friedle-Crafts acmlation using acid as catalyst. Zinc chloride, aluminum chloride, titanium (IV) chloride, hydrochloric acid or acetic acid may be used, but polyphosphoric acid is often preferred for this type of intramolecular cycloadditions. The temperature can vary from 0-150° C. For example, 3,4-dihydrobenzopyrano[4,3,2-de]isoquinolin-1-one 4 can be prepared as follows: To a liquid of 12 g of polyphosphoric acid in a 500 mL beaker is added 9-xanthenemethylisocyanide 3 (2.37 g, 10 mmol) portion wise with manual stirring at 90° C. The mixture is stirred for three minutes and then 100 g of more polyphosphoric acid is added. Vigorous stirring is applied for four minutes when temperature is kept ait 90° C. The mixture is allowed to cool to 60° C. and 40 g of crushed ice is added until the polyphophoric acid is completely hydrolyzed and a brown solid is separated. The solid is collected by vacuum filtration and then recrystallized in chloroform to afford a unsaturated product (0.15 g 0 0.63 mmol) in 6.3% yield.

The solid is dissolved in lacial acetic acid (100 mL) and the solution is placed in a hydrogenation bomb. Palladium (10% on carbon, 500 mg) is added. The bomb is set pressure at 2000 psi. The mixture of the content is stirred for 20 hours under the pressure and poured through a fluted filter paper to remove the catalyst. The solvent of the filtrate is removed in vacuo to give a yellow solid, which is recrystallized in chloroform to afford desired product (0.95 g 4.0 mmol) in 80% yield.

Monosulfonation of 3,4-dihydrobenzopyrano[4,3,2-de]isoquinoli-1-one 4 can be achieved using chorosulfonic acid neat to give compound 5. The temperature can vary from −20 to 100° C. Amidation of compound 5 can be carried out by a variets of conditions known to those skilled in the art, including reaction with first or secondary amines using pyridine or triethyl amine as base. Typical solvents include chlorinated solvents, various ethers, and dipolar aprotic solvents like DMF. Thus final products of compounds 6 can be prepared from 3,4-dihydrobenzopyrano[4,3,2-de]isoquinoli-1-one 4 using General procedure A and B.

Scheme 2 below illustrates schematically the preparation of compounds Example 5 through Example 9.

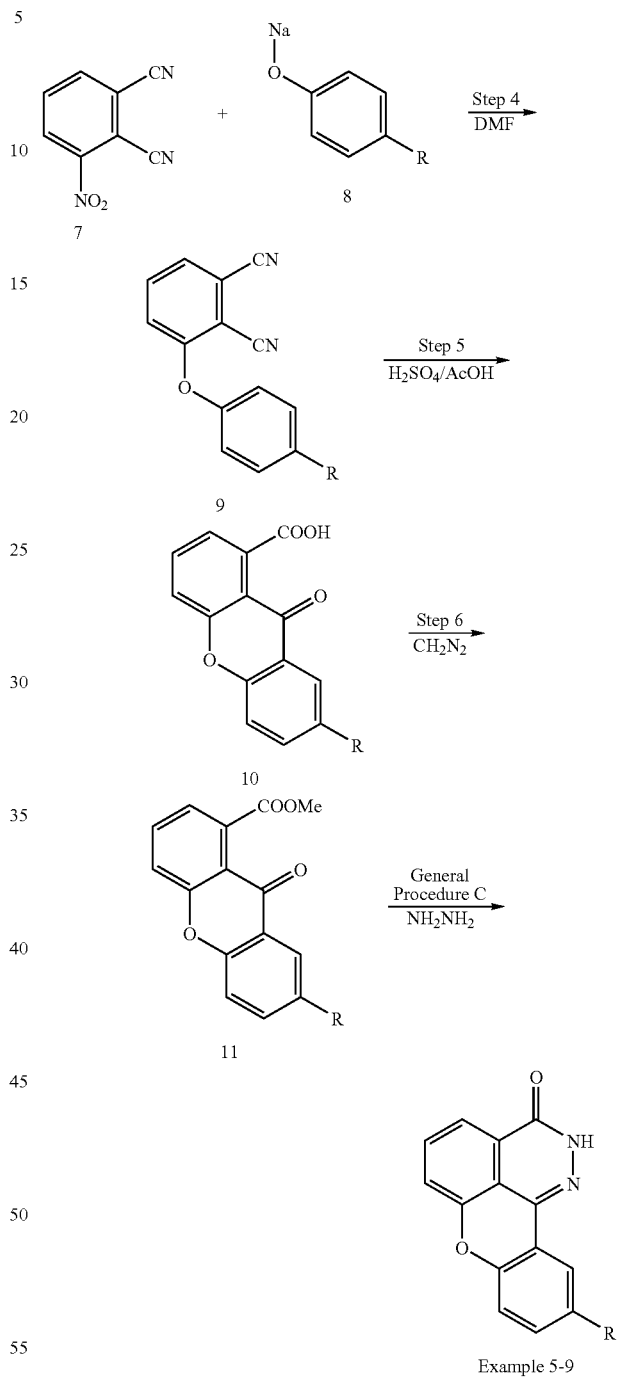

Step 4

Preparation of 3-phenoxyphthalonitrile 7. The starting materials 3-nitrophthalonitrile 7 and or p-substituted phenoxide 8 are either readily available from commercial sources or can be prepared by known methods by those skilled in the art. The desired compound can be easily obtained by coupling the orthodinitrile with the phenoxide salt in dipolar aprotic solvent, such as DMF, low dialkyl ketones, lower alkyl nitriles.

Temperature range can be 0-150° C. For example, a mixture of 0.1 Mol of 3-nitrophthalonitrile and 0.14 Mol of sodium phenoxide (or p-substituted phenoxide) in 120 ml of dry DMF is mechanically stirred for 2.5 hours at room temperature and then poured into water. The precipitate is collected by filtration, washed with water, and dried under vacuum to give 19 g (0.086 Mol. 86%) of the compound 9, mp 110-112° C.

Step 5

Preparation of 9-oxoxanthene-1-carboxylic acid 10. The formation of orthocarboxylic acid groups from the cyano groups can be achieved by hydrolysis of the aryl nitrile with either mineral acids, include sulfuric acids and hydrochloric acids, or strong inorganic base. These conditions are understood by those skilled in the art. An intramolecular Friedle-Crafts acylation can occur as soon as the diacids are formed to afford 9-oxoxanthene-1-carboxylic acid 10. For example, a solution of 0.1 Mol of 3-phenoxyphthalonitrile is dissolyed in 150 ml of a mixture of 60 per cent sulfuric acid and glacial acid. The mixture is refltled for 6 hours and then poured into 1000 mL of ice-cold water. pH value of the suspension is adjusted to 10 with sodium carbonate. Impurities are extracted out by partitioning of the basified solution wvith ethyl acetate. Precipitation is formed upon adding hydrogen chloride (to pH5) to the aqueous solution, and collected by filtration to give a designed acid in 70% yield.

Step 6

Preparation of 9-oxoxanthene-1carboxylic acid methyl ester 11.

Esterification of acid can be achieved by several conventional methods by those skilled in the art. These procedures include utilizing diazomethane or methyl alcohol catalyzed by mineral acids. For example, ethereal diazomethane solution can be prepared from N-methyl-N-nitrosotoluene-p-sulphonamide and potassium hydroxide from a water bath. 9-Oxoxanthene-1-carboxylic acid (1.29 g, 5 mmol) in absolute methanol is added to this ethereal diazomethane solution at 0° C. until a pale yellow color formed. Removal of the solvent provides the desired ester solid in 100% yield. Thus the final products, Examples 5-9, can be prepared by condensation hydrazine with the ketonester 11 as described in General procedure C.

Scheme 3 below illustrates schematically the preparation of compounds Example 10 through Example 11.

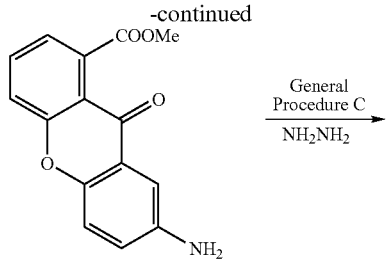

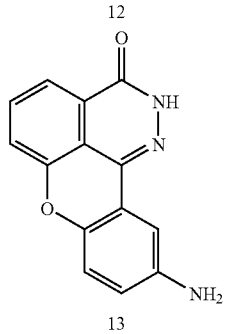

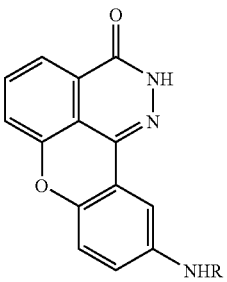

Example 10-11

Step 7

Preparation of 7-amino-9-oxoxanthene-1-carboxylic acid methyl ester 12. Reduction of the nitro group can be carried out under catalytic hydrogenation conditions utilizing metal catalysts described in aldrichimica Acta 1979:12, or with hydrazine, metal hydride reducing agents such as $NaBH_4$, $B_2H_6$, and the like. Suitable solvents include water, lower alcohol, ethers, THF, lower alkyl organic acids such as acetic acid. Temperature can vary from 0-100° C. Desired final products, Examples 11-12, can be prepared by condensing the ketonester 12 with hyddrazine using General procedure C, followed by an amide bond formation of the phthalazine derivative 13 using General procedure F.

Scheme 4 below illustrates schematically the preparation of Example 12 through Examples 24.

Scheme 3

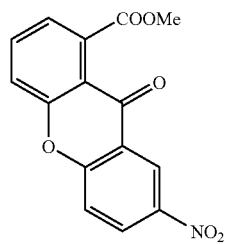

Step 7
Pd—C, $H_2$, R = $NO_2$

Scheme 4

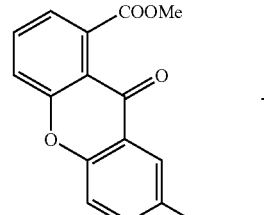

Step 9
NBS

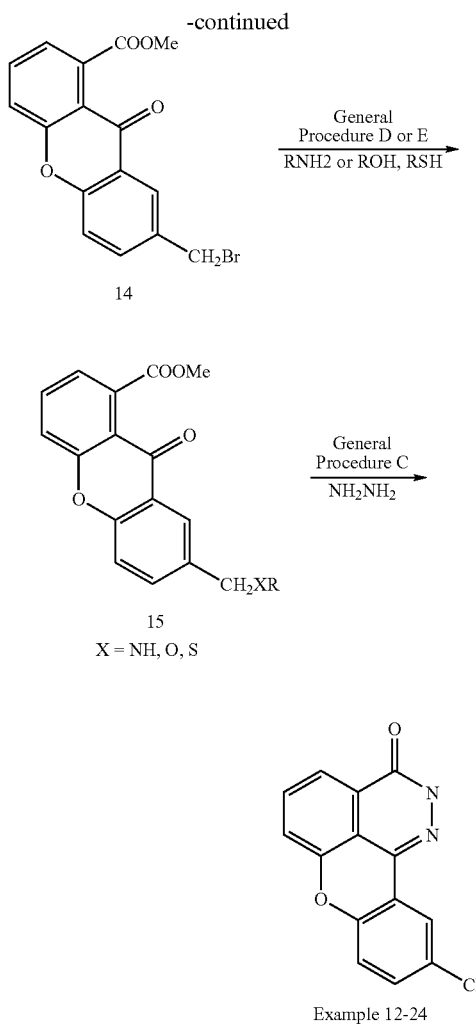

Example 12-24

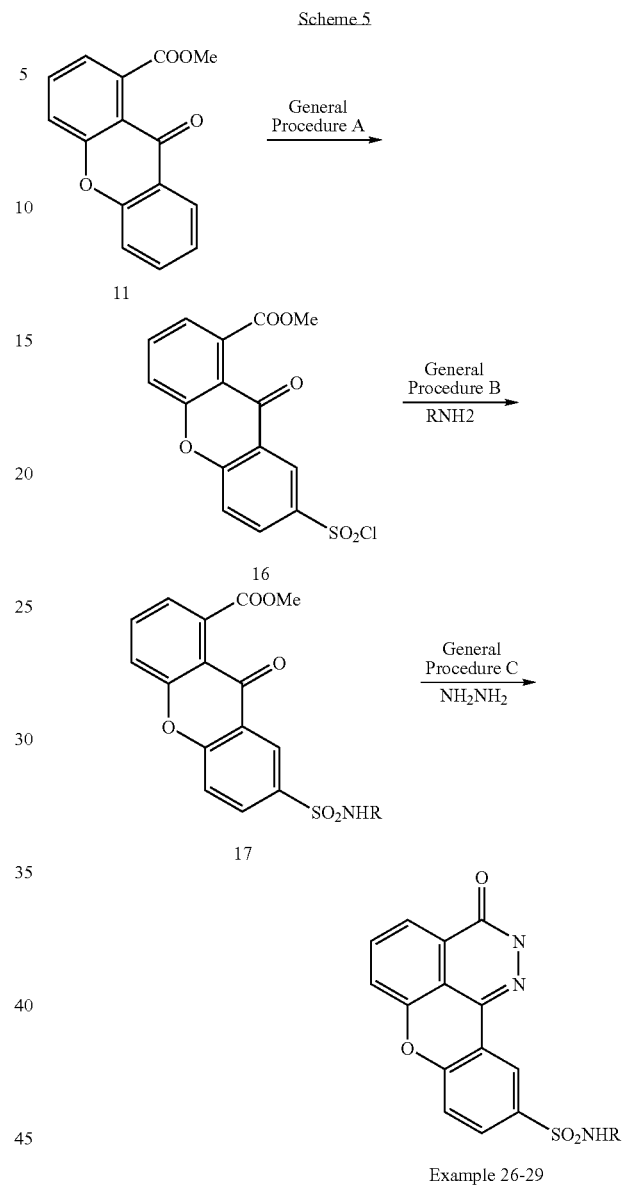

Example 26-29

Step 9

Preparation of 7-bromomethyl-9-oxoxanthene-1-carboxylic acid methyl ester 14. Brominating agents include N-bromosuccinimide, bromine, complexed bromine such as pyridinium bromide, perbromide, and the like can be used to convert 7-methyl-9-oxoxanthene-1-carboxylic acid methyl ester 11 to 7-bromomethyl-9-oxoxanthene-1-carboxylic acid methyl ester 14. Solvents include chlorinated hydrocarbones, dipolar aprotic solvents, and various ethers. Temperature can range from 0-100° C. For example, a suspension of 7-methyl-9-oxoxanthene-1-carboxylic acid methyl ester (0.1 Mol), N-bromosuccinimide (0.12 Mol), and benzoylperoxide (10 mg) in dry carbon tetrachloride (300 mL) is stirred at 60° C. for 6 hours. The mixture is filtered, the solid is washed successively with small amounts of chloroform, water and ether, and then dried to leave a desired product as white solid.

Displacement of the bromo group of compound 14 with nucleophiles such as anine or alcohol, thiol using General procedure D or E provides the compound 15. The ketonester 15 can be cyclized with hydrazine using General procedure C to give desired final products, Example 12-24.

Scheme 5 below illustrates schematically the preparation of Example 26 through Example 29.

Monosulfonation of the ketone ester 11 to give compound 16 can be achieved using neat chorosulfonic acid to react wvith the substrate 11. The temperature can vary from −20 to 100° C. Amidation of compound 16 can be carried out by a variety of conditions known to those skilled in the art, including reaction with first or secondary amines using pyridine or triethyl amine as base. Typical solvents include chlorinated solvents, various ethers, and dipolar aprotic solvents like DMF. Thus final product of compounds can be prepared from compound 17 and hydrazine as described in General procedure C.

General procedure A:

To a liquid of chlorosulfonic acid (10 mL) is added the compound 5 or ketone ester (11, 7.37 mmol) under nitrogen at 0° C. The resulting mixture is allowed to warm to room temperature, continuously stirred for about 2 days and poured onto 100 g of ice. The residue is collected by filtration and washed with water, ethanol to afford the product 5 or 16 as solid in >80% of yield.

General procedure B:

To a suspension of the sulfonyl chloride 5 or (16, 5.67 mmol) in methylene chloride (100 mL) is added triethyl amine (1.6 mL) and amine compound (5 mmol) under nitrogen at 0° C. The reaction mixture is allowed to warm to room temperature, stirred continuously for 1 hour and poured into 100 mL of water. The organic layer is collected, washed with water, brine and concentrated in vacuo. The product is purified via crystallization or silica column chromatography using methanol/methylene chloride as eluent to afford solid product in 60-90% of yield.

General procedure C:

A benzopyrano[4,3,2-de]phthalazine ring can be formed by condensation of the ketone ester with hydrazine. To a solution of the ketonester 11 or 15, (17.5 mmol) in absolute ethanol (10 mL) is added anhydrous hydrazine in ethanol (1 mL) drop wise at room temperature. The solution is refluxed for overnight and cooled to room temperature. Ice-cold water (100 mL) is added and brown solid is separated. The solid is collected by vacuum filtration and washed with water, small amount of methanol to give a solid product in 10-80% of yield.

General procedure D:

To a solution of the bromo compound (14.10 mmol) in dry DMF (100 mL) is added potassium carbonate (100 mmol) and secondary amine (10 mmol). The reaction mixture is heated to 70° C. for 6 hours and cooled to 0° C. Water (100 mL) is added to the reaction mixture, followed by ethyl acetate (200 mL). The organic layer is collected, washed with water, brine and dried over sodium sulfate. The solvent is removed in vacuo. The residue is purified by column chromatography on silica gel using ethyl acetate/hexane as eluent to give the product 15 in 60-90% of yield.

General procedure E:

To a stirred solution of the bromo compound 14 (10 mmol) and phenol derivative or thiol derivative (10 mmol) in acetone (150 mL) is added potassium carbonate (100 mmol). The reaction mixture is heated to reflux for 6 hours. The solvent is then removed in vacuo, and water (100 mL) and ethylacetate (100 mL) are added to the residue. The organic layer is collected, washed with water, brine and dried over sodium sulfate. The solvent is removed in vacuo. The residue is purified by column chromatography on silica gel using ethyl acetate/hexane as eluent to give the product 15 in 60-80% of yield.

General procedure F:

To a suspension of compound phthalazine derivative 13 (10 mmol) in dry DMF (20 mL) is added succinic or acetic anhydride (11 mmol). The mixture is heated to 110° C. for 3 hours and cooled to room temperature. The mixture is continuously stirred for 2 hours after addition of THF (100 mL). The solid is collected by filtration, washed with methanol to afford a desired product without further purification.

Other manners, variations or sequences of preparing the compounds of Formula I will be readily apparent to those skilled in the art.

The compounds of formula I may be useful in the free base form, in the form of base salts where possible, and in the form of addition salts, as well as in the free acid form. All these forms are within the scope of this invention. In practice, use of the salt form amounts to use of the base form. Pharmaceutically acceptable salts within the scope of this invention are those derived from mineral acids such as hydrochloric acid and sulfturic acid; and organic acids such as ethanesuifonic acid, benzenesuifonic acid, p-toluenesulfonic acid, and the like, giving the hydrochloride, sulfonate, ethanesulfonate, benzenesulfonate, p-toluenesulfonate, and the like respectively, or those derived from bases such as suitable organic and inorganic bases. Examples of pharmaceutically acceptable base addition salts with compounds of the present invention include organic bases which are nontoxic and strong enough to form such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methyligiucamine; L-glutamine; N-methylpiperazine; morpholine; ethylenedianane; N-benzylphenethylamine; tris (hydroxymethyl)antinoethane; and the like.

The acid addition salts of the basic compounds may he prepared by dissolving the free base of the compound of formula I in aqueous or aqueous alcohol solution or other suitable solvents containing the appropriate acid or base and isolating the salt by evaporating the solution, or by reacting the free base of the compound of formula I with an acid as well as reacting the compound of formula I having an acid group thereon with a base such that the reactions are in an organic solvent, in which case the salt separates directly or can be obtained by concentration of the solution.

The compounds of this invention contain one or more aminetric carbon atoms. Therefore, the invention includes the individual stereoisomers and mixtures thereof as well as the racemic compounds. The individual isomers may be prepared or isolated by methods known in the art.

The compounds of the invention exhibit pharmacological activity and are, therefore, useful as pharmaceuticals. In particular the compounds exhibit central nervous and cardiac vesicular system activity.

EXAMPLE 1

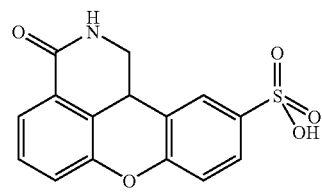

To a solution of 0.3 g of compound 4 in 7.5 mL of concentrate sulfuric acid (98%) is dropwise-added 2.0 mL of fuming sulftric acid at 0° C. The mixture is stirred for 3 hours at 0° C. and poured into 100 mL of ice-cold water. The precipitation is collected by filtration, washed with water to give 0.17 g of a white solid, mp>300 (dec.). $^1$H-NMR (400 MHz, DMSO-d6); 8.20(d, 1H 4 Hz); 7.62(d, 1H, 8 Hz); 7.53(s, 1H); 7.51(d, 1H, 8 Hz); 7.41(t, 1H, 8 Hz); 7.30(d, 1H, 8.0 Hz); 7.09(d, 1H, 8.0 Hz); 4.50-4.55(dd, 1H, 8 Hz, 12 Hz); 4.02-3.96(m, 1H); 3.46(t, 1H, 12 Hz).

EXAMPLE 2

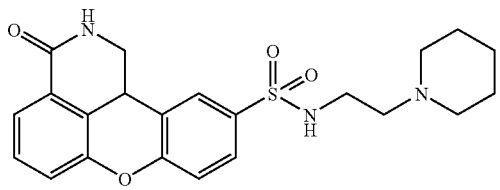

Prepared from compound 5 and N-(2-aminoethyl)piperidine according to General Procedure B. Purification of compound by crystallization in water-acetone gives a white solid, mp 265-269° C. $^1$H-NMR (400 MMz, DMSO-d6); 8.35(m, 1H), 7.82 (s, 1H), 7.75 (m, 1H), 7.67 (m, 1H), 7.46-7.43 (m, 1H), 7.37 (m, 1H), 4.58-4.54 (m, 1H), 4.10 (m, 1H), 3.5-3.47 (m, 1H), 3.39 (m, 2H), 3.06 (bs, 2H), 3.02 (bs, 2H), 2.32 (s, 2H), 1.44-1.19 (m, 6H).

EXAMPLE 3

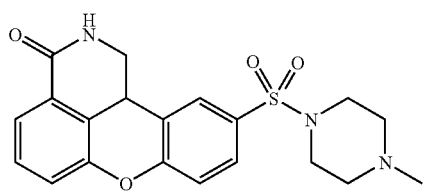

Prepared from compound 5 and N-methylpiperazine according to General Procedure B. Purification of compound by crystallization in acetic acid gives a white solid, mp 300° C. (dec.). $^1$H-NMR (400 MHz, CDCl$_3$); 7.78-7.84 (d, J=8 Hz, 1H), 7.58-7.64 (d, J=8 Hz, 1H), 7.53 (s, 1H), 7.32-7.40 (t, J=8, 16 Hz, 1H), 7.16-7.26 (m, 2H), 6.30 (br s, 1H), 4.36-4.50 (q, J=6, 14, 20 Hz, 1H), 4.02-4.12 (m, 1H), 3.60-3.74 (t=12, 24 Hz, 1H), 3.01 (br s, 4H), 2.46 br s, 4H), 2.24, (s, 3H).

EXAMPLE 4

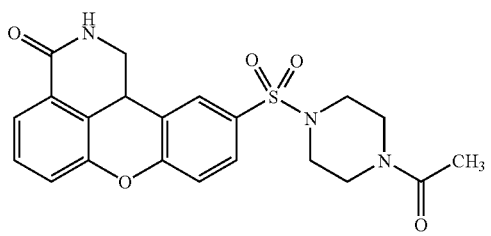

Prepared from compound 5 and N-acetylpiperazine according to General Procedure B. Purification of compound by crystallization in acetic acid gives a white solid (45% yield), mp 290° C. (dec.). $^1$H-NMR (400 MHz, CDCl$_3$); 7.88-7.93 (d, J=8 Hz, 1H), 7.67-7.72 (dd, J=4, 12 Hz, 1H), 7.62 (s, 1H), 7.43-7.49 (t, J=8, 16 Hz, 1H), 7.27-7.36 (m, 2H), 4.54-4.62 (dd, J=8.20 Hz, 1H), 4.15-4.25 (m, 1H), 3.70-3.85 (m, 3H), 3.59(s, 2H), 3.04 (s, 4H), 2.06 (s, 3H).

EXAMPLE 5

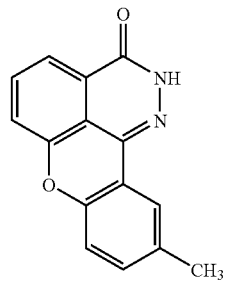

Prepared from the compound 11 (R=Me) and hydrazine according to General Procedure C. Purification of compound by crystallization in ethanol gives a whit flake solid (44% yield), mp 332-334° C. $^1$H-NMR (400 MHz, DMSO-d$_6$); 12.5 (s, br, 1H); 7.90-7.87 (m, 3H); 7.69 (dd, J=7.2, 1.9 Hz, 1H; 7.38 (dd, J=8.8, 1.9 Hz, 1H); 7.31 (d, J=8.4 Hz, 1H); 2.39 (s, 3H).

EXAMPLE 6

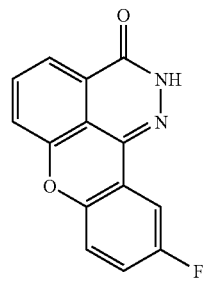

Prepared from the compound 11 (R=F) and hydrazine according to General Procedure C. Purification of compound by crystallization in ethanol gives a whit solid (20% yield), mp 355° C. (dec.). $^1$H-NMR (400 MHz, DMSO-d$_6$); 12.7(s, br, 1H); 8.42 (d, J=2.0 Hz, 1H); 7.91 (m, 2H), 7.73(dd, J=2.0, 6.8 Hz, 1H); 7.41(m, 2H)

EXAMPLE 7

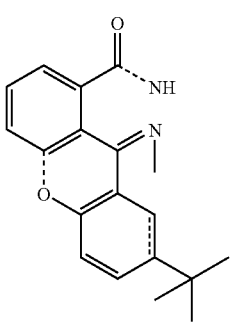

Prepared from the compound 11 (R=t-Bu) and hydrazine according to General Procedure C. Purification of compound by crystallization in ethanol gives a solid (30% yield), mp 380° C. (dec.). ¹H-NMR (400 MHz, DMSO-d₆); 8.07 (d, J=2.5 Hz, 1H); 7.91 (dd, J=7.6, 7.0 Hz, 1H), 7.89 (d, J=7.6 Hz, 1H), 7.72(dd, J=7.0, 2.0 Hz, 1H), 7.65 (dd, J=9.0, 2.5 Hz, 1H); 7.37 (d, J=9.0 Hz, 1H), 1.38 (s, 9H)

EXAMPLE 3

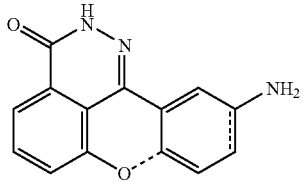

Prepared from the compound 11 (R=NH₂) and hydrazine according to General Procedure C. Purification of compound by crystallization in ethanol gives a yellowish solid (60% yield), mp 300° C. (dec.). ¹H-NMR (400 MHz, DMSO-d₆); 5.29-5.31 (d, 2H, J=7.8 Hz), 6.81-6.83 (dd, 1H, J=8.8, 2.4 Hz), 7.14-7.16 (d, 1H, J=8.8 Hz), 7.26-7.27 (d, 1H, J=2.2 Hz), 7.63-7.65 (d, 1H, J=7.3 Hz), 7.83-7.89 (dd, J=7.5, 15.5 Hz), 7.85 (s, 1H), 12.52(s, br, 1H).

EXAMPLE 9

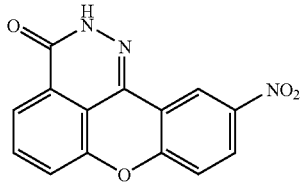

Prepared from the compound 11 (R=NO₂) and 1.5 equivalent of hydrazine according to General Procedure C. Purification of compound by crystallization in a cetic acid gives a yellowish solid (20% yield), mp>300° C. (dec.). ¹H-NMR (400 MHz, DMSO-d₆); 7.46-7.49 (d, 1H, J=9.2 Hz,), 7.75-7.77 (d, 1H, J=8.1 Hz), 7.97-8.01 (dd, 1H, J=8.1 Hz), 8.13-8.15 (d, 1H, J=7.9 Hz,), 8.38-8.42 (dd, 1H, J=9.5 Hz), 9.07-9.08 (d 1H, J=2.6 Hz).

EXAMPLE 10

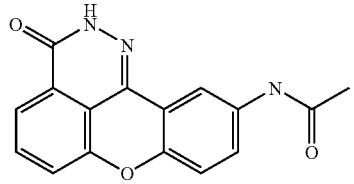

Prepared from the amino compound 13 and acetic anhydride according to General Procedure F. Purification of the compound by crystallization in ethanol to gives a yellow solid in 80% yield, mp 350° C. (dec.). ¹H-NMR (400 MHz, DMSO-d₆); 2.08 (s, 1H), 7.36-7.38 (d, 1H, J=8.9), 7.66-7.70 (dd, 1H, J=2.6. 16.1 Hz), 7.68-7.69 (d, 1H, J=2.2 Hz), 7.88-7.91 (d, 1H, J=8.6 Hz), 7.89 (s, 1H), 8.49 (d, 1H, J=2.5 Hz), 10.15 (s, 1H, NHCO), 12.62 (s, 1H).

EXAMPLE 11

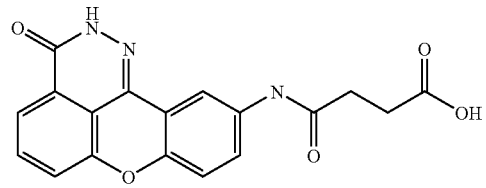

Prepared from the amino compound 13 and succinic anhydride according to General Procedure F. Purification of the compound by crystallization in ethanol to gives a yellow solid in 20% yield, mp 320° C. (dec.). ¹H-NMR (400 MHz, DMSO-d₆); 2.50-2.60 (m, 4H), 7.45-7.47 (d, 1H, J=8.9 Hz), 7.74-7.77 (dd, 1H, J=9.2, 2.5 Hz), 7.76-7.79 (dd, 1H, J=7.2, 2.1), 7.96-7.98 (d, 1H, J=9.3 Hz), 7.97 (s, 1H), 8.56-8.57 (d, 1H, J=2.5 Hz) 10.29(s, 1H), 12.72 (s, 1H).

EXAMPLE 12

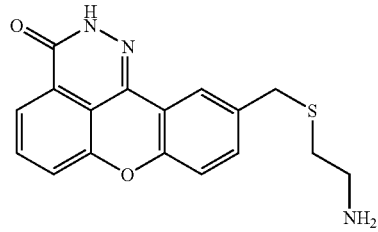

Prepared from the compound 14 and cysteamine according to General Procedure E. Puinfication of compound by crystallization in ethanol gives white solid product in 30% of yield mp 255-275° C. (methylsulfonic acid salt). ¹H-NMR (400 MHz, DMSO-d₆); 2.29 (s, 3H), 2.64 (t, 2H, J=7.3 Hz), 3.01 (br s, 2H), 3.92 (s, 2H), 7.42 (d, 1H, J=8.5 Hz), 7.54-7.57 (dd, 1H, J=2.1 Hz, 8.6 Hz), 7.71-7.76 (m, 4H), 7.89-7.95 (m, 2H), 8.0 (d, 1H, J=2.1 Hz), 12.69 (s, 1H).

EXAMPLE 13

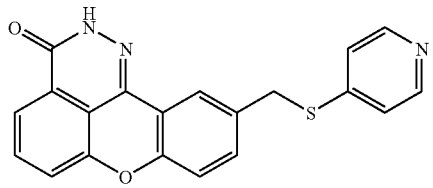

Prepared from the compound 14 and 4-mercaptopyridine according to General Procedure E. Purification of compound by crystallization in ethanol gives white solid product in 38% of yield, mp 237-240° C. ¹H-NMR (400 MHz, DMSO-d₆); 12.68 (s, 1H), 8.61 (m, 2H), 8.24 (d, 1H, J=2.2 Hz), 7.92-7.85 (m, 4H), 7.70 (m, 2H), 7.44 (d, 1H, J=8.5 Hz, 4.70 (s, 2H), 2.30 (s, 3H).

EXAMPLE 14

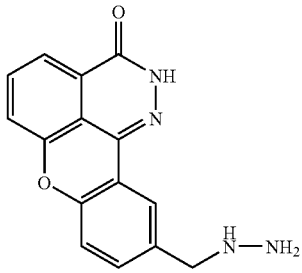

Prepared from the compound 14 and hydrazine according to General Procedure D. Purification of compound by crystallization in acetic acid gives a yellow solid product in 78% of yield. Mp>300° C. $^1$H-NMR (400 MHz, DMSO-d$_6$); 12.64 (s, br, 1H), 8.04 (d, J=2 Hz, 1H), 7.93-7.88 (m, 2H), 7.71 (dd, J=1.9 Hz, and 7.3 Hz, 1H), 7.51 (dd, J=2.1 Hz, and 8.5 Hz, 1H), 7.37 (d, J=8.4 Hz, 1H), 3.82 (s, 2H).

EXAMPLE 15

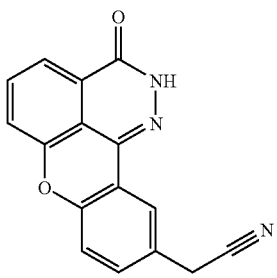

Prepared from the compound 14 and potassium cyanide according to General Procedure D. Purification of compound by crystallization in acetic acid gives a light yellow solid product in 70% of yield, mp>300° C. $^1$H-NMR (400 MHz, DMSO-d$_6$); 12.70 (s, 1H, NH), 8.10 (d, J=2.0 Hz, 1H), 7.91 (m, 2H), 7.72 (dd, J=1.8, 7.2 Hz, 1H), 7.53 (dd J=2.2, 8.6 Hz, 1H), 7.46 (d, J=8.6 Hz, 1H), 4.18 (s, 2H).

EXAMPLE 16

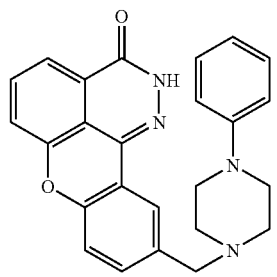

Prepared from the compound 14 and 1-phenylpiperazine according to General Procedure D. Purification of compound by crystallization in ethanol gives a white solid product in 89% of yielcl mp >300° C. (dec.), $^1$H-NMR (400 MHz, DMSO-d$_6$); 12.63 (s, br, 1H), 8.06 (d, J=1.9 Hz, 1H), 7.90 (m, 2H), 7.72 (dd, J=7.1 and 1.9 Hz, 1H), 7.53 (dd, J=8.5 and 2.0 Hz, 1H), 7.40 (d, J=8.5, 1H), 7.19 (m, 2H), 6.92 (d J=8.0 Hz, 2H), 6.76 (t, J=7.3 Hz, 1H), 3.61 (s, 2H), 3.14 (t, J=4.3 Hz, 2H), 2.56 (t, J=4.2 Hz, 2H).

EXAMPLE 17

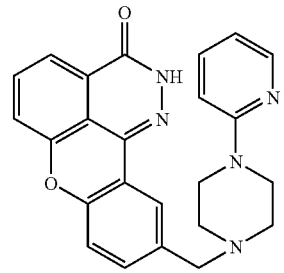

Prepared from the compound 14 and 1-(2-pyridyl)piperazine according to General Procedure D. Purification of compound by crystallization in ethanol gives a white solid product in 89% of yield, mp>300° C. (dec.). $^1$H-NMR (400 MHz, DMSO-d$_6$); 12.64 (s, br, 1H), 8.09 (m, 2H), 7.90 (m, 2H), 7.71 (dd, J=7.2 and 1.8 Hz, 1H), 7.52 (m, 2H), 7.40 (d, J=3.5 Hz, 1H), 6.80 (d, J=8.6 Hz, 1H), 6.62 (m, 1H), 3.60 (s, 2H), 3.49 (s, 4H), 3.30 (s, 4H).

EXAMPLE 18

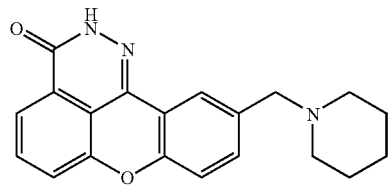

Prepared from the compound 14 and piperidine according to General Procedure D. Purification of compound by crystallization in ethanol gives a white solid product in 69% of yield, mp 195-200° C. $^1$H-NMR (400 MHz, DMSO-d$_6$); 1.30-1.45 (m, 1H) 1.53-1.75 (m, 3H), 1.75-1.90 (m, 2 H), 2.35 (s, 3H), 2.82-3.0 (2 H), 3.30-3.4 (m, 2H), 4.39 (d, 2H, J=5.2 Hz), 7.51 (d, 1H, J=8.5 Hz), 7.65-7.68 (dd, 1H, J=2.1 Hz, 8.5 Hz), 7.74-7.76 (m, 1H), 7.91-7.96 (m, 2H), 8.29 (d, 1H, J =2.1 Hz), 9.33 (bs, 1H), 12.79 (s, 1H).

EXAMPLE 19

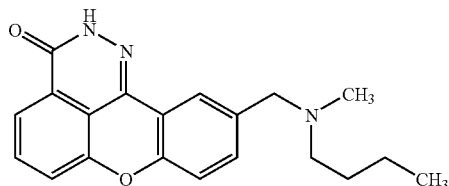

Prepared from the compound 14 and N-methylbutylamine according to General Procedure D. Purification of compound by crystallization in ethanol gives a white solid product in 69% of yield, mp 133-135° C. $^1$H-NMR (400 MHz, DMSO-d$_6$); 0.91 (t, 3H, J=7.4 Hz,), 1.29-1.34 (m, 2H), 1.65-1.70 (m, 2H), 2.35 (s, 3H), 2.69 (d, 3H, J=4.8 Hz), 3.03-3.05 (m, 1H), 3.14 (m, 1H), 7.53 (d, 1H, J=8.5 Hz), 7.67-7.69 (dd, 1H, J=2.0 Hz, 8.5 Hz), 7.73-7.76 (m, 1H), 7.91-7.96 (m 2H), 8.30 (s, 1H, J=2.0 Hz), 9.50 (s, 1H), 12.79 (s, 1H).

EXAMPLE 20

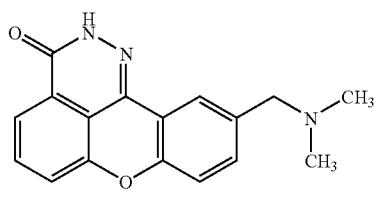

Prepared from the compound 14 and N-dimethylamine according to General Procedure D. Purification of compound by crystallization in ethanol gives a white solid product in 70% of yield. $^1$H-NMR (400 MHz, DMSO-d$_6$); 2.36 (s, 3H), 2.78 (d, 6H, J=4.8 Hz), 4.40 (m, 2H), 7.53 (d, 1H, J=8.5 Hz), 7.65-7.70 (m, 1H), 7.75 (m, 1H), 92-7.95 (m, 2H), 8.28 (m, 1H), 9.70 (s, 1H), 12.78 (s, 1H).

EXAMPLE 21

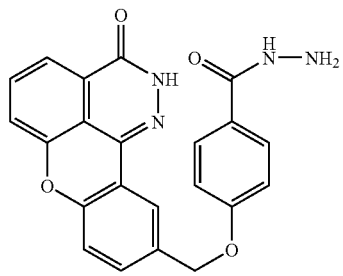

Prepared from the compound 14 and N-methylbutylamine according to General Procedure E. Purification of compound by crystallization in acetic acid gives a gray solid product in 59% of yield, Mp>300° C. (dec.). $^1$H-NMR (400 MHz, DMSO-d$_6$); 12.67 (s, 1H), 9.62 (s, 1H), 8.17 (d, J=2.0 Hz, 1H), 7.90 (m, 2H), 7.80 (d, J=8.8 Hz, 2H), 7.72 (dd, J=1.7 and 7.2 Hz, 1H), 7.64 (dd, J=2.1 and 8.6 Hz, 1H), 7.45 (d, J=8.5 Hz, 1H), 7.09 (d, J=8.8 Hz, 2H), 5.27 (s, 2H), 4.42 (br s, 2H).

EXAMPLE 22

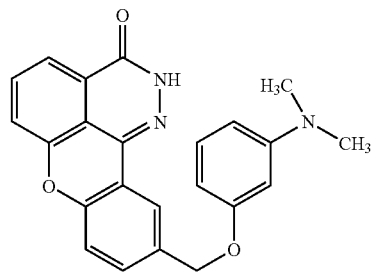

Prepared from the compound 14 and dimethylphenol according to General Procedure E. Purification of compound by crystallization in acetic acid gives a light yellow solid product in 50% of yield, mp>300° C. (dec.), $^1$H-NMR (400 MHz, DMSO-d$_6$); 12.65 (s, br, 1H), 8.16 (d, J=2.0 Hz, 1H), 7.91 (m, 2H), 7.72 (dd, J=7.1 and 2.0 Hz, 1H), 7.63 (dd, J=8.6 and 2.1 Hz, 1H), 7.44 (d, J=8.5 Hz, 1H), 7.07 (t, J=7.5 Hz, 1H), 6.33 (m, 3H), 5.17 (s, 2H), 2.37 (s, 6H).

EXAMPLE 23

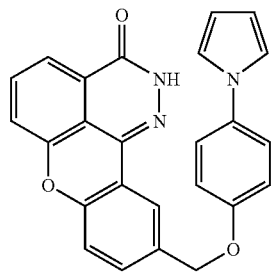

Prepared from the compound 14 and 4-(1-imidazole) phenol according to General Procedure E. Purification of compound by crystallization in ethanol gives a white solid product in 70% of yield. Mp>300° C. (dec.), $^1$H-NMR (400 MHz, DMSO-d$_6$); 12.66 (s, br, 1H), 8.18 (d, J=2 Hz, 1H), 7.91 (m, 2H), 7.73 (dd, J=7.1 and 1.9 Hz, 1H), 7.66 (dd, J=8.5 and 2.1 Hz, 1H), 7.48 (m, 3H), 7.25 (t, J=2.1 Hz, 2H), 7.12 (m, 2H), 6.22 (t, J=2.1 Hz, 2H), 5.25 (s, 2H)

EXAMPLE 24

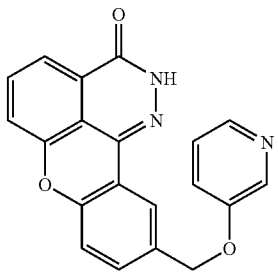

Prepared from the compound 14 and 3-hydroxypyridine according to General Procedure E. Purification of compound by crystallization in ethanol gives a yellow solid product in 57% of yield. Mp>300° C. (dec.). $^1$H-NNR (400 MHz, DMSO-d$_6$); 12.67 (s, br, 1H), 8.39 (d, J=2.9 Hz, 1H), 8.19 (d, J=2.8 Hz, 2H), 7.91 (m, 2H), 7.72 (dd, J=7.1 and 2.0 Hz, 1H), 7.66 (dd J=8.5 and 2.2 Hz, 1H), 7.49 (m, 2H), 7.35 (m, 1H), 5.30 (s, 2H).

EXAMPLE 25

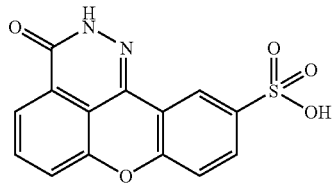

Prepared from the compound 11 (R=H) and 1.5 equivalent of hydrazine to give benzopyrano[4,3,2-de]phthalazine according to General Procedure C. To a solution of 0.3 g of benzopyrano[4,3,2-de]phthalazine in 7.5 mL of concentrate sulfuric acid is dropwise added 2.0 mL of fuming sulfuric acid at 0° C. The mixture is stirred for 3 hours at 0° C. and poured into 100 mL of ice-cold water. The precipitation is collected by filtration, washed with water to give of a white solid product, mp>300° C. (dec.). 1H-NMR (400 MHz, DMSO-d$_6$); 12.7 (s, 1H), 8.35 (s, 1H), 7.92-7.90 (m, H), 7.76-7.71 (m, 2H), 7.38 (d, 1 H).

EXAMPLE 26

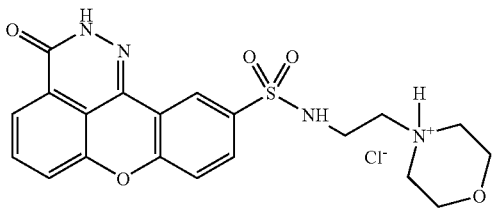

Prepared from the compound 16 and N-(2-aminoethyl) morpholine according to General Procedure B. Purification of compound by silica gel column chromatography provides sulfonamide 17. Condensation of compound 17 with hydrazine according to General Procedure C in ethanol affords a solid which is purified by crystallization in ethanol gives a white solid product in 70% of yield. To this amine compound (10 mmol) in dioxane (10 mL) is added 10 mmol of hydrochloric acid in dioxane at 60° C. White salt solid product is formed upon cooling the solution to room temperature. The solid is collected by filtration, mp 302-307° C. 1H-NMR (400 MHz, DMSO-$d_6$); 12.81 (s, 1H), 10.90 (s, 1H), 8.49 (d, 1 H 2.3 Hz), 8.30 (s, 1H), 7.99-7.92 (m, 3H), 7.78-7.75 (dd, 1H, 2.6 Hz, 6.5 Hz,), 7.65 (d, 1H, 8.8 Hz), 3.95-3.92 (m, 2H), 3.78-3.72 (t, 2H, 11.3 Hz), 3.43-3.39 (m, 2H), 3.33 (s, 4H), 3.10-3.08 (m, 2H).

EXAMPLE 27

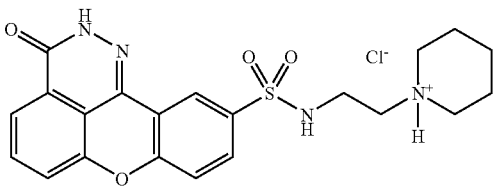

Prepared from the compound 16 and 1-(2-aminoethyl) piperidine according to General Procedure B. Purification of compound by silica gel column chromatography provides sulfonamide 17. Condensation of compound 17 with hydrazine according to General Procedure C in ethanol-water affords a solid which is purified by crystallization in ethanol gives a white solid product in 50% of yield. To this amine compound (10 mmol) in dioxane (10 mL) is added 11 mmol of hydrocloric acid in dioxane at 60° C. White solid product is formed upon cooling the solution to room temperature and collected by filtration, mp>300° C. (dec.). 1H-NMR (400 MHz, DMSO-$d_6$); 12.82 (s, 1H), 9.80 (s, 1H), 8.49 (d, 1H, 2.4 Hz), 8.26 (m, 1H), 7.96-7.94 (m, 3H), 7.78 (dd, 1H, 2.6 Hz, 6.5 Hz), 7.67 (d, 1H, 8.8 Hz), 3.20-3.17 (m, 2H), 3.13-3.12 (m, 2H), 2.89-2.87 (m, 2H), 1.75-1.68 (m, 6H), 1.45-1.30 (m, 2H).

EXAMPLE 28

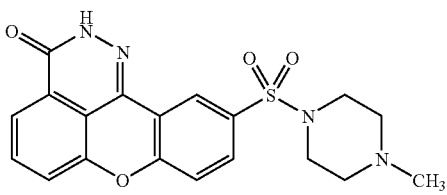

Prepared from the compound 16 and N-methylpiperazine according to General Procedure B. Purification of compound by silica gel column chromatography provides sulfonamide 17. Condensation of compound 17 with hydrazine according to General Procedure C in ethanol affords a solid which is purified by crystallization in ethanol gives a white solid product in 45% of yield, Mp>300° C. (dec.). 1H-NNR (400 MHz, DMSO-$d_6$); 12.82 (s, 1H), 10.55 (s, 1H), 8.36 (d, 1H, 2.3 Hz), 7.96-7.91 (m, 3H), 7.79 (dd, 1H, 2.7 Hz, 6.5 Hz), 7.71 (d, 1H, 8.7 Hz), 3.90-3.80 (bs, 2H), 3.50-3.40 (bs, 2H), 3.20-3.10 (bs, 2H), 2.85-2.70 (m, 5H).

EXAMPLE 29

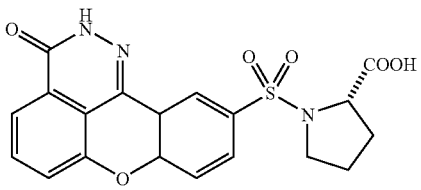

Prepared from the compound 16 and L-proline according to General Procedure B. Purification of compound by silica gel column chromatography provides sulfonamnide 17. The compound 17 is reacted with hydrazine according to General Procedure C in ethanol affords a solid which is purified by crystallization in ethanol gives a white solid product in 29% of yield, mp>300 (dec.)° C. 1H-NMR (400 MHz, DMSO-$d_6$); 12.78 (s, 1H), 8.41 (d, 1H, J=2.3 Hz), 7.99-7.92 (m, 3H), 7.79 (dd, 1H, J=5.6 Hz, 8.2 Hz), 7.63 (d, 1H, J=8.7 Hz), 4.14 (m, 1H), 3.41-3.32 (m, 2H), 1.99-1.90 (m, 1H), 1.90-1.33 (m, 2H), 1.68-1.63 (m, 1H).

EXAMPLE 30

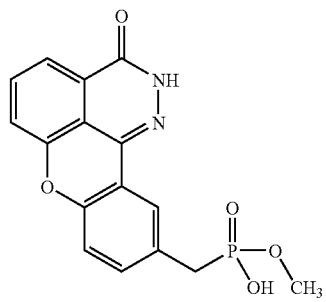

To a solution of compound 14 in m-xylene is added triethyl phosphite the mixture is refluxed for 2 hours and cooled to room temperature. The precipitation is collected by filtration to give phosphonic ester. Condensation of this compound with hydrazine according to General Procedure C in ethanol affords a solid which is purified by crystallization in ethanol gives a white solid product in 70% of yield, Mp 196-201° C. LRMS (fab. M+1)=345. 1H-NMR (400 MHz, DMSO-$d_6$); 7.36 (t, J=7.8 Hz, 1H), 7.23 (d, J=7.6 Hz, 1H), 7.08 (d, 7.7 Hz, 1H), 6.99 (s, 1H), 6.78 (d, J=8.0 Hz, 1H), 6.54 (d, J=8.4 Hz, 1H), 3.53 (d, J=10.4 Hz, 3H), 2.82 (d, J=20.1 Hz, 2H).

EXAMPLE 31

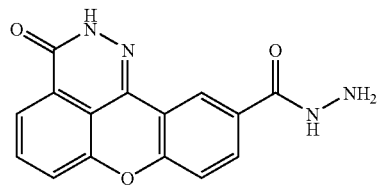

Prepared from the compound 11 (R=COOMe) and hydrazine according to General Procedure C. Purification of compound by crystallization in acetonitrile gives a whit solid (40% yield), mp>400° C. (dec.). $^1$H-NMR (400 MHz, DMSO-d$_6$); 12.73 (s, br, 1H); 9.99 (s, 1H); 8.57 (d, J=2.0 Hz, 1H); 7.98 (dd, J=5.5, 2.2 Hz, 1H); 7.92 (m, 2H); 7.33 (dd, J=6.5, 2.6 Hz, 1H); 7.47(d, J=8.7 Hz, 1H); 4.55 (s, 2H).

Other variations and modifications of this invention using the synthetic pathways described above will be obvious to those skilled in the art.

Methods of Using the Compounds of the Invention

The compounds of the present invention can treat or prevent tissue damage resulting from cell damage or death due to necrosis or apoptosis: can ameliorate neural or cardiovascular tissue damage, including that following focal ischemia. myocardial infarction, and reperfusion injury; can treat various diseases and conditions caused or exacerbated by PARP activity; can extend or increase the lifespan or proliferative capacin of cells; can alter the gene expression of senescent cells; and can radiosensitize cells. Generally, inhibition of PARP activity spares the cells from energy loss, preventing, in the case of neural cells, irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells. The present invention also relates to treating diseases and conditions in an animal which comprises administering to said animal a therapeutically effective amount of the above-identified compounds.

In particular, the present invention relates to a method of treating. preventing or inhibiting a neurological disorder in an animal, which comprises administering to said animal a therapeutically effective amount of the above-identified compounds. In a particularly preferred embodiment, the neurolcgical disorder is selected from the group consisting of peripheral neuropathy caused by physical injury or disease state, traumatic brain injury, physical damage to the spinal cord. stroke associated with brain damage, focal ischemia, global ischemia, reperfusion injury, demyelinating disease and neurological disorder relating to neurodegeneration. Another preferred embodiment is when the reperusion injury is a vascular stroke. Yet another preferred embodiment is when the peripheral neuropathy is caused by Guillain-Barre syndrome. Still another preferred embodiment is when the demyelinating disease and neurological disorder relates to neurodegeneration. Another preferred embodiment is when the reperfusion injur is a vascular stroke. Still another preferred embodiment is when the demyelinating disease is multiple sclerosis. Another preferred embodiment is when the neurological disorder relating to neurodegeneration is selected from the group consisting of Alzheimer's Disease. Parkinson's Disease, and amyotrophic lateral sclerosis.

Yet another preferred embodiment is a method of treating, preventing or inhibiting a cardiovascular disease in an animal, such as angina pectoris, invocardial infarction, cardiovascular ischemia, and cardiovascular tissue damage related to PARP activation, by administering to said animal an effective amount of the compounds of the present invention.

The present invention also contemplates the use of compound I, II, III, IV or V for inhibiting PARP activity, for treating, preventing or inhibiting tissue damage resulting from cell damage or death due to necrosis or apoptosis, for treating, preventing or inhibiting a neurological disorder in an animal.

In a particularly preferred embodiment the neurological disorder is selected from the group consisting of peripheral neuropathy caused by physical injury or disease state, traumatic brain injury, physical damage to the spinal cord, stroke associated with brain damage, focal ischeria, global ischemia, reperfusion injury, demyelinating disease and neurological disorder relating to neurodegeneration.

Another preferred embodiment is when the reperfusion injury is a vascular stroke. Yet another preferred embodiment is when the peripheral neuropathy is caused by Guillain-Barre syndrome. Still another preferred embodiment is when the demyelinating disease is multiple sclerosis. Another preferred embodiment is when the neurological disorder relating to neurodegeneration is selected from the group consisting of Alzheimer's Disease. Parkinson's Disease, and amyotrophic lateral sclerosis.

The present invention also contemplates the use of compound I, II, III, IV, or V in the preparation of a medicament for the treatment of any of the diseases and disorders in an animal described herein.

In a particular embodiment, the disease or disorder is a neurological disorder.

In a particularly preferred embodiment, the neurological disorder is selected from the group consisting of peripheral neuropathy caused by physical injure or disease state, traumatic brain injury, physical damage to the spinal cord, stroke associated with brain damage, focal ischemia, global ischemia, reperfusion injury, demyelinating disease and neurological disorder relating to neurodegeneration. Another preferred embodiment is when the reperfusion injui v is a vascular stroke. Yet another preferred embodiment is when the peripheral neuropathy is caused by Guillain-Barre syndrome.

Still another preferred embodiment is when the demyelinating disease is multiple sclerosis. Another preferred embodiment is when the neurological disorder relating to neurodegeneration is selected from the group consisting of Alzheimer's Disease, Parkinson's Disease, and amyotrophic lateral sclerosis.

The term "preventing neurodegeneration" includes the ability to prevent neurodegeneration in patients newly diagnosed as having a neurodegenerative disease, or at risk of developing a new degenerative disease and for preventing further neurodegeneration in patients who are already suffering from or have symptoms of a neurodegenerative disease.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

As used herein, the term "neural tissue damage resulting from ischemia and reperfusion injury" includes neurotoxicity, such as seen in vascular stroke and global and focal ischemia. As used herein, the term "neurodegenerative diseases," includes Alzheimer's disease. Parkinson's disease and Huntington's disease.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, preferably a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of; gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), or microwave radiation (1 mm to 30 cm).

Compositions and Methods for Effecting Neuronal Activity

Preferably, the compounds of the invention inhibit PARP activity and, thus, are believed to be useful for treating neural tissue damage, particularly damage resulting from cerebral ischemia and reperfusion injury or neurodeenerative diseases in animals. The term "nervous tissue" refers to the various components that make up the nervous system including, without limitation, neurons, neural support cells, glia, Schwann cells, vasculature contained within and supplying these structures, the central nervous system, the brain, the brain stem, the spinal cord, the junction of the central nervous system with the peripheral nervous system, the peripheral nervous system, and allied structures.

Further, according to the invention, am effective therapeutic amount of the compounds and compositions described above are administered to animals to effect a neuronal activity, particularly one that is not mediated by NMDA neurotoxicity. Such neuronal activity may consist of stimulation of damaged neurons, promotion of neuronal regeneration, prevention of neurodegenerauon and treatment of a neurological disorder. Accordingly, the present invention further relates to a method of effecting a neuronal activity in an animal, comprising administering an effective amount of the compound of formula I, II, III, IV, or V to said animal.

Examples of neurological disorders that are treatable by the method of using the present invention include, without limitation, trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barré syndrome; Alzheimer's disease; Huntington's Disease and Parkinson's disease.

The method of the present invention is particularly useful for treating a neurological disorder selected from the group consisting of: peripheral neuropathy caused by physical injury or disease state; head trauma, such as traumatic brain injury; physical danage to the spinal cord; stroke associated with brain damage, such as vascular stroke associated with hypoxia and brain damage, focal cerebral ischemia, global cerebral ischemia, and cerebral reperfusion injury; demyelinating diseases, such as multiple sclerosis; and neurological disorders related to neurodegeneration, such as Aklzheimer's Disease. Parkinson's Disease. Huntington's Disease and amyotrophic lateral sclerosis (ALS).

Treating Other PARP-Related Disorders

The compounds, compositions and methods of the present invention are particularly useful for treating or preventing tissue damage resulting from cell death or damage due to necrosis or apoptosis.

The compounds, compositions and methods of the invention can also be used to treat a cardiovascular disorder in an animal, by administering an effective amount of the compound of formula to the animal. As used herein, the term "cardiovascular disorders" refers to those disorders that can either cause ischemia or are caused by recerfusion of the heart. Examples include, but are not limited to, coronary artery disease, angina pectoris. myocardial infarction, cardiovascular tissue damage caused by cardiac arrest, cardiovascular tissue damage caused by cardiac bypass, cardiogenic shock, and related conditions that would be known by those of ordinary skill in the art or which involye dysfunction of or tissue damage to the heart or *vasculature, especially, but not limited to, tissue damage related to PARP activation.

For example, the methods of the invention are believed to be useful for treating cardiac tissue damage. particularly damage resulting from cardiac ischetnia or caused by reperfusion injury in animals. The methods of the invention are particularly useful for treating cardiovascular disorders selected from the group consisting of; coronary artere disease, such as atherosclerosis; angina pectoris; myocardial infarction; myocardial ischemia and cardiac arrest; cardiac bypass; and cardioaenic shock. The methods of the invention are particularly helpful in treating the acute forms of the above cardiovascular disorders.

Further, the methods of the invention can be used to treat tissue damage resulting from cell damage or death due to necrosis or apoptosis, neural tissue damage resulting from ischemia and reperfusion injury. neurological disorders and neurodegenerative diseases; to prevent or treat vascular stroke; to treat or prevent cardiovascular disorders; to treat other conditions and/or disorders such as age-related muscular degeneration. AIDS and other immune senescence diseases, arthritis, atherosclerosis, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells, or to radiosensitize tumor cells Further still, the methods of the invention can be used to treat cancer and to radiosensitize tumor cells. The term "cancer" is interpreted broadly. The compounds of the present invention can be "anti-cancer agents". which also encompasses "anti-tumor cell growth agents" and "anti-neoplastic agents". For example, the methods of the invention are useful for treating cancers and radiosensitizing twunor cells in cancers such as ACTH-producing tumors, acute lymphocytic leukemia, acute nonlymphocytic leukemia, cancer of the adrenal cortex. bladder cancer, brain cancer, breast cancer, cervical cancer, chronic lymphointic leukemia, chronic myelocytic leukemia, colorectal cancer, cutaneous T-cell lymphoma. endometrial cancer, esophageal cancer. Ewing's sarcoma, gallbladder cancer, hairy cell leukemia, head & neck cancer. Hodgkin's lymphoma. Kaposi's sarcoma, kidney cancer, liver cancer, lung cancer (small and/or non-small cell), malignant peritoneal effusion. malignant pleural effusion, melanoma, mesothelioma, multiple myeloma, neuroblastoma, non-Hodgkin's lymphoma, osteosarcoma ovarian cancer, ovary (germ cell) cancer, prostate cancer, pancreatic cancer, penile cancer, retinoblastona, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The term "radiosensitizer", as used herein, is defined as a molecule, preferably a low molecular weight molecule, administered to animals in thlerapeutically effective amounts to increase the sensitivit of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of; gamma-radiation ($10^{-20}$ to $10^{-13}$ m) x-ray radiation ($10^{-11}$ to $10^{-3}$ m), ultraviolet light (10 nm to 400 nm), visible light (400 nm to 700 nm), infrared radiation (700 nm to 1.0 mm), and microwave radiation (1 mm to 30 cm).

Radiosensitizers are known to increase the sensitivit of cancerous cells to the toxic effects of electromagnetic radiation. Several mechanisms for the mode of action of radiosensitizers have been suggested in the literature including; hypoxic cell radiosensitizers (e.g., 2-nitroimidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C. RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to; 5-fluorouracil. leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Pharmaceutical Compositions of the Invention

The present invention also relates to a pharmaceutical composition comprising (i) a therapeutically effective amount of the compound of formula I, II, III, IV or V and (ii) a pharmaceutically acceptable carrier.

The above discussion relating to the preferred enbodiments' utility and administration of the compounds of the present invention also applies to the pharmaceutical composition of the present invention.

The term "pharmaccutically acceptable carrier" as used herein refers to any carrier, diluent, excipient, suspending agent, lubricating agent, adjuvant, vehicle, delivery system, emulsifier, disintegrant, absorbent, preservative, surfactant, colorant flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous. intravenous, intramuscular, intraperitoneal, intmthecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline. Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

Formulations suitable for nasal or buccal administration (such as self-propelling powder dispensing formulations) may comprise about 0.1% to about 5% w/w, for example 1% w/w of active ingredient. The formulations for liwnan medical use of the present invention comprise an active ingredient in association with a pharmaceutically acceptable carrier therefore and optionally other therapeutic ingredient(s).

When administered orally, the composition will usually be formulated into unit dosage forms such as tablets, cacliets, powder, granules, beads, chewable lozenges, capsules, liquids, aqueous suspensions or solutions. or similar dosage forms, using conventional equipment and techniques known in the art. Such formulations typically include a solid, semisolid, or liquid carrier. Exemplar carriers include lactose, dextrose, sucrose, sorbitol, mannitol, sutarches, gum acacia, calcium phosphate, mineral oil, cocoa butter, oil of theobroma. alginates, tragacanth. gelatin. syrup. methyl cellulose, polyoxyethylene sorbitan monolaurate, methyl hydroxybenzoate, propyl hydroxybenzoate, talc, magnesium stearate, and the like.

The composition of the invenuton is preferably administered as a capsule or tablet containing a single or divided dose of the inhibitor. Preferably, the composition is administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-dosing. Such controlled release films are well known to the art. Particularly preferred are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly(hydroxyethylmethacrylate) or poly (vinylalcohol) also may be useful, but for shorter release cycles than the other polymer release systems, such as those mentioned above.

In a preferred embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer. or may be encapsulated in some way vwithin the polymer, or may be molded into a solid implant.

In one embodiment, the biodegradable polymer or polymer mixture is used to form a soft "depot" contaimnng the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be elininated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. The compositions may be sterilized and/or contain adjuvants, such as presenring, stabilizing, welling, or emulsifying agents, solution promoters, salts for regulating the osmotic pressure, and/or bulffers. In addition, they may also contain other therapeutically valuable substances. The compositions are prepared according to conventional mixing, granulating, or coating methods, and contain about 0.1 to 75% by weight, preferably about 1 to 50% by weight, of the active ingredient.

To be effective tlerapeutically as central nenous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds preferably include pharmaceutical dosage units comprising an efficacious quantity of active compound. By an efficacious quantity is meant a quantity sufficient to inhibit PARP and derive its beneficial effects through administration of one or more of the pharmaceutical dosage units. Preferably, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a phartnacologicafll acceptable salt thereof for a mamual sufferng from, or likely to suffer from, any of condition as described hereinbefore is in the range of about 0.1 mg/kg to about 100 mg/kg of the active ingredient compound, the most preferred dosage being about 1 to about 10 mg/kg.

It is understood. however, that a specific dose level for any particular patient will depend upon a varies of factors including the activity of the specific compound employed, the age, body, weight, general health, sex, diet, time of administration, rate of excretion, drug combination, and the severity of the particular disease being treated and form of administration.

It is understood that the ordinarily skilled physician or yeterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage form incorporating the compositions of the invention, the compounds may also be blended with conventional excipients such as binders, including gelatin, pregelatinized starch, and the like; lubricants, such as hydrogenated vegetable oil, sutearic acid, and the like; diluents, such as lactose, mannose, and sucrose; disintegrants, such as carbox.nmethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D. & C. dyes and lakes; flavorants; and sweeteners.

The present invention relates to the use of compounds I, II, III, IV or V in the preparation of a medicament for the treatment of any disease or disorder in an animal described herein.

PARP Assays $IC_{50}$

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0). 1 mM $MgCl_2$, 28 mM KCl, 28 mM NaCl, 0.1 mg/ml of DNase I activated herring sperm DNA (Sigma. Mo.), 3.0 micromolar [3 H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting. The compounds of this invention were found to have potent enzymatic activity in the range of a few 20 µM in $IC_{50}$ in this inhibition assay.

Using the PARP assay described above, approximate $IC_{50}$ values were obtained for the following compounds:

| Compound | $IC_{50}$ (µM) | Compound | $IC_{50}$ (µM) |
|---|---|---|---|
| (triethylamine salt) | 0.131 |  | 0.069 |

-continued
| Compound | IC₅₀ (μM) | Compound | IC₅₀ (μM) |
|---|---|---|---|
| 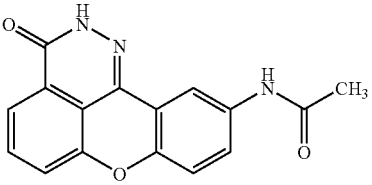 | 0.036 | 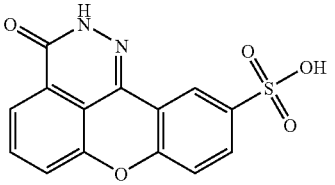 | 0.052 |
| 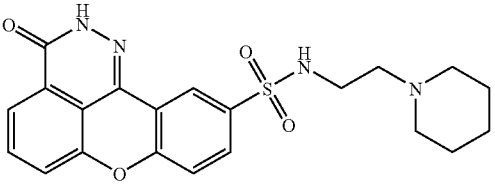 | 0.192 | 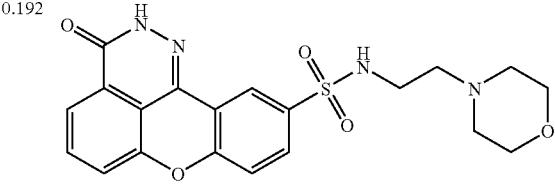 | 0.081 |
| 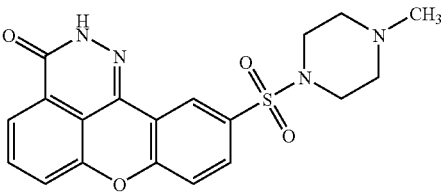 | 0.208 | 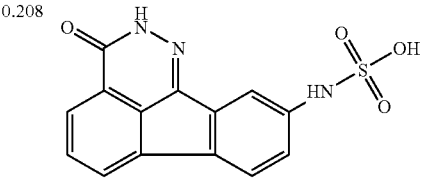 (sodium salt) | 0.040 |
| 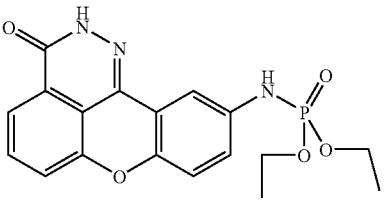 | 0.199 | 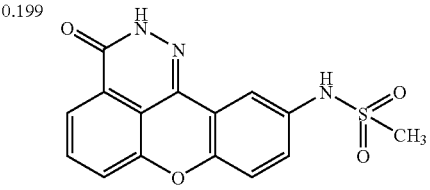 | 0.198 |
| 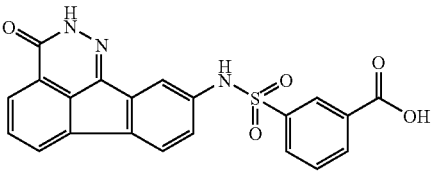 | 0.052 | 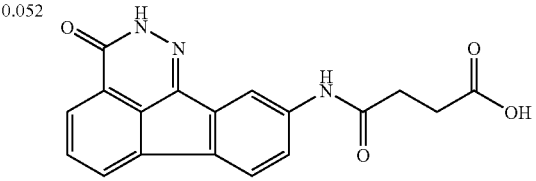 | 0.029 |
| 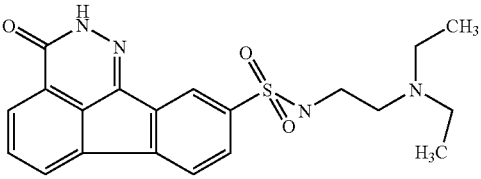 | 0.390 | 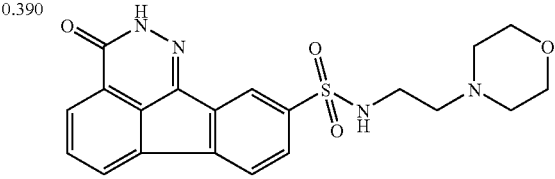 | 0.340 |
| 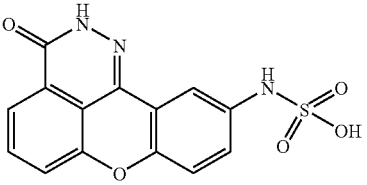 | 0.025 | 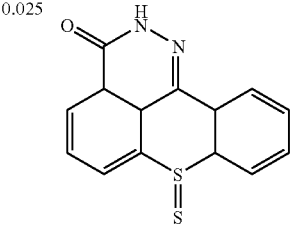 | 33 |

-continued
| Compound | IC$_{50}$ (μM) | Compound | IC$_{50}$ (μM) |
|---|---|---|---|
| 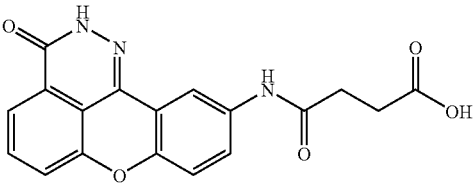 | 0.021 | 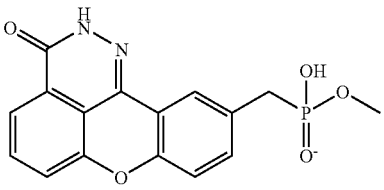 | |
| 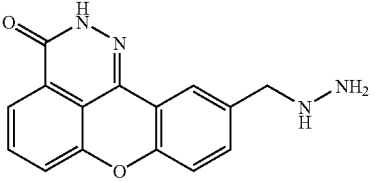 | 0.045 | 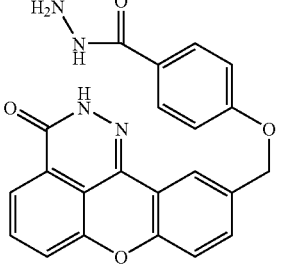 | 0.035 |
| 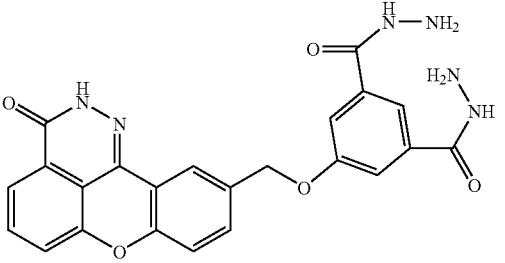 | 0.04 | 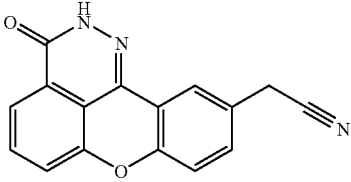 | 0.025 |
| 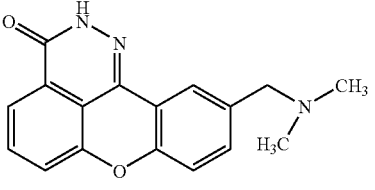 | 0.017 | 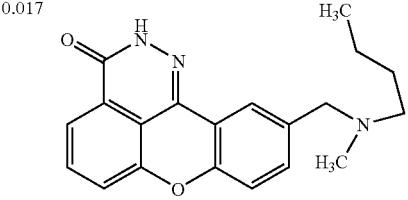 | 0.12 |
| 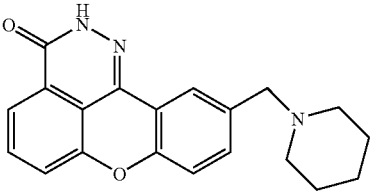 | 0.072 | 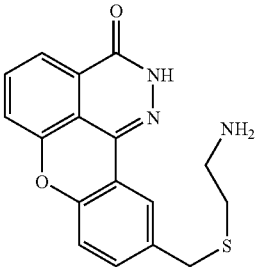 | 0.028 |

-continued
| Compound | IC$_{50}$ (μM) | Compound | IC$_{50}$ (μM) |
|---|---|---|---|
| 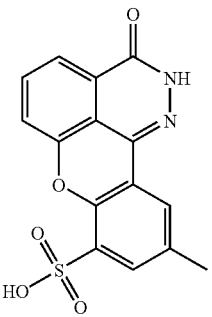 | 2.03 | 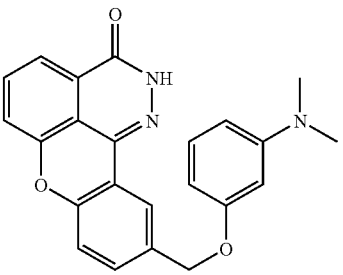 | 0.128 |
| 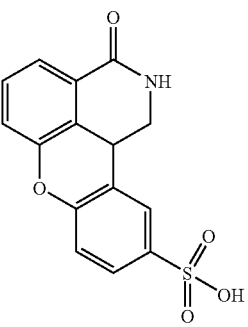 | 0.161 | 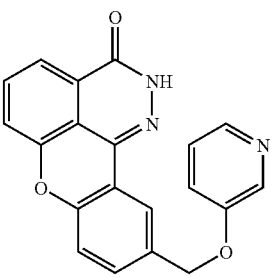 | 0.054 |
| 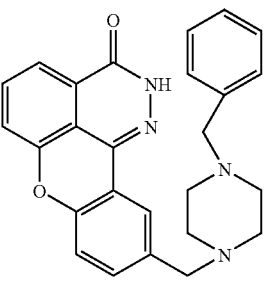 | 0.044 | 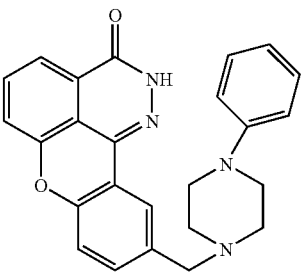 | 0.062 |
| 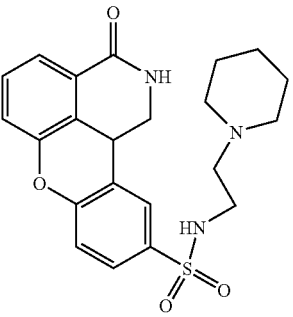 | 0.361 | 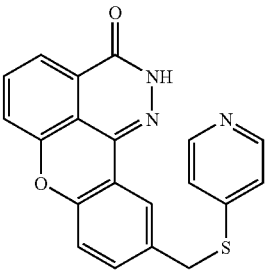 | 0.017 |
| 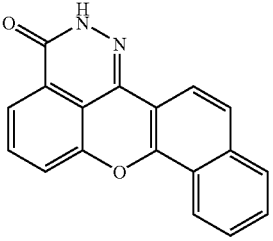 | 40 | 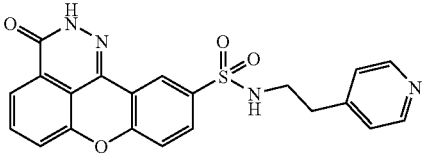 | 0.089 |

-continued

| Compound | IC₅₀ (μM) | Compound | IC₅₀ (μM) |
|---|---|---|---|
| (structure) | 25 | (structure) | 0.139 |
| (structure) | 0.1 | (structure) | 0.077 |
| (structure) | 11 | (structure) | 0.3610 |
| (structure) | 0.233 | (structure) | 0.144 |
| (structure) | 0.058 | (structure) | 0.595 |

| Compound | IC$_{50}$ (μM) | Compound | IC$_{50}$ (μM) |
|---|---|---|---|
| (structure) | 0.158 | (structure) | 0.059 |
| (structure) | 0.185 | (structure) | 0.037 |
| (structure) | 0.085 | (structure) | 0.018 |
| (structure) | 0.065 | (structure) | 0.023 |
| (structure) | 0.075 | | |

Focal cerebral ischemia

The following focal cerebral ischemia assay is useful for determining the PARP inhibiting effects of the compounds of the present invention. The following examples demonstrate that compunds related to those of the present invention are effective in inhibiting PARP activity.

Focal cerebral ischemia is produced by cauterization of the right distal MCA (middle cerebral artery) with bilateral temporary common carotid artery occlusion in male Long-Evans rats for 90 minutes. All procedures performed on the animals are approved byv the University Institutional Animal Care and Use Committee of the University of Pennsylvania. A total of 42 rats (weights; 230-340 g) obtained from Charles River were used in this study. The animals fasted overnight with free access to water prior to the surgical procedure.

Two hours prior to MCA occlusion, varying amounts (control, n=14; 5 mg/kg, n=7; 10 mg/kg, n=7; 20 mg/kg, n=7; and 40 mg/kg, n=7) of the compound. 3,4-dihydro-5-[4-(1-piperidinyl)-butoxy]-1(2H)-isoquinolinone ("DPQ") were dissolyed in dimethyl sulfoxide (DMSO) using a sonicator. A volume of 1.28 mg/kg of the resulting solution was injected intraperitoneally into fourteen rats.

The rats were then anesthetized with halothane (4% for induction and 0.8%-1.2% for the surgical procedure) in a mixture of 70% nitrous oxide and 30% oxygen. The body temperature was monitored by a rectal probe and maintained at 37.5±0.5° C. with a heating blanket regulated by a homeothennic blanket control unit (Harvard Apparatus Limited, Kent, U.K.). A catheter (PE-50) was placed into the tail artery, and arterial pressure was continuously monitored and recorded on a Grass polygraph recorder (Model 7D. Grass Instruments, Quincy, Mass.). Samples for blood gas analysis (arterial pH, $PaO_2$ and $PaCO_2$) were also taken from the tail artery catheter and measured with a blood gas analyzer (ABL 30, Radiometer, Copenhagen, Denmark). Arterial blood samples were obtained 30 minutes after MCA occlusion.

The head of the animal was positioned in a stereotaxic frame, and a right parietal incision between the right lateral canthus and the external auditory meatus was made. Using a dental drill constantly cooled with saline, a 3 mm burr hole was prepared over the cortex supplied by the right MCA. 4 mm lateral to the sagittal suture and 5 mm caudal to the coronal suture. The dura mater and a thin inner bone layer were kept care being taken to position the probe over a tissue area devoid of large blood vessels. The flow probe (tip diameter of 1 mm, fiber separation of 0.25 mm) was lowered to the bottom of the cranial burr hole using a micromanipulator. The probe was held stationary by a probe holder secured to the skull with dental cement. The microvascular blood flow in the right parietal cortex was continuously monitored with a laser Doppler flowmeter (FloLab, Moor, Devon, U.K., and Periflux 4001, Perimed, Stockholm, Sweden).

Focal cerebral isclemia was produced by cauterization of the distal portion of the right MCA with bilateral temporary common carotid artery (CCA) occlusion by the procedure of Chen et al., "A Model of Focal Ischemic Stroke in the Rat; Reproducible Extensive Cortical Infarction", Stroke 17; 738-43 (1986) and/or Liu et al., "Polyethylene Glycol-conjugated Superoxide Dismutase and Catalase Reduce Ischemic Brain Injury". Am. J. Physiol. 256;H589-93 (1989), both of which are hereby incorporated by reference.

Specifically, bilateral CCA's were isolated, and loops made from polyethylene (PE-10) catheter were careftilly passed around the CCA's for later remote occlusion. The incision made previously for placement of the laser doppler probe was extended to allow observation of the rostral end of the zygomatic arch at the fusion point using a dental drill, and the dura mater overlying the MCA was cut. The MCA distal to its crossing with the inferior cerebral vein was lifted by a fine stainless steel hook attached to a micromanipulator and, following bilateral CCA occlusion, the MCA was cauterized with an electrocoagulator. The burr hole was covered with a small piece of Gelform, and the wound was sutured to maintain the brain temperature within the normal or near-normal range.

After 90 minutes of occlusion, the carotid loops were released, the tail arterial catheter was removed, and all of the wounds were sutured. Gentarnicin sulfate (10 mg/ml) was topically applied to the wounds to prevent infection. The anesthetic was discontinued and the animal was returned to his cage after awakening. Water and food were allowed ad libitum.

Two hours after MCA occlusion, the animals were given the same doses of the PARP inhibitor as in the pre-treatment. Twenty-four hours after MCA occlusion, the rats were sacrificed with an intraperitoneal injection of pentobarbital sodium (150 mg/kg). The brain was carefully removed from the skull and cooled in ice-cold artificial CSF for five minutes. The cooled brain was then sectioned in the coronal plane at 2 mm intervals using a rodent brain matrix (RBM 4000C. ASI Instruments, Warren, Mich.). The brain slices were incubated in phosphate-buffered saline containing 27% 2,3,5-triphenyltetrazolium chloride (TTC) at 37° C. for ten minutes. Color photographs were taken of the posterior surface of the stained slices and were used to determine the damaged area at each cross-sectional level using a computer-based image analyzer (NIH Image 1.59). To avoid artifacts due to edema, the damaged area was calculated by subtracting the area of the normal tissue in the hemisphere ipsilateral to the stroke from the area of the hemisphere contralateral to the stroke, by the method of Swanson et al., "A Semiautomated Method for Measuring Brain Infarct Volume". J. Cereb. Blood Flow Mletabol, 10:290-93 (1990), the disclosure of which is hereby incorporated by reference. The total volume of infarction was calculated by summation of the damaged volume of the brain slices.

The cauterization of the distal portion of the right MCA with bilateral temporary CCA occlusion consistently produced a well-recognized cortical infarct in the right MCA territory of each test animal. There was an apparent uniformity in the distribution of the damaged area as measured by TTC staining in each group. as shown in FIG. 1.

In FIG. 1, the distribution of the cross-sectional infarct area at representative levels along the rostrocaudal axis was measured from the interaural line in non-treated animals and in animals treated with 10 mg/kg of 3,4-dihydro-5-[4-(1-piperidinyl)-butox]-1(2H)-isoquinolinone. The area of damage was expressed as mean±standard deviation. Significant differences between the 10 mg-treated group and the control group were indicated ($p<0.02$, $p<0.01$, $p<0.00$ 1). The 5 mg/kg and 20 mg/kg curves fell approximately halfway between the control and the 10 mg/kg curves, whereas the 40 mg/kg curve was close to the control. The 5, 20 and 40 mg/kg curves were omitted for clarity.

PARP inhibition led to a significant decrease in the damaged volume in the 5 mg/kg-treated group ($106.7 \pm 23.2$ $mm^3$, $p<0.001$), the 10 mg/kg-treated group ($76.4 \pm 16.8$ $mm^3$, $p<0.001$), and the 20 mg/kg-treated group ($110.2 \pm 42.0$ $mm^3$, $p<0.01$), compared to the control group ($165.2 \pm 34.0$ $mm^3$). The data are expressed as mean±standard deviation. The significance of differences between groups was determined using an analysis of variance (ANOVA) followed by Student's t-test for individual comparisons.

There was no significant difference between the control and the 40 mg/kg-treated group ($135.6 \pm 44.8$ $mm^3$). However, there were significant differences between the 5 mg/kg-treated group and the 10 mg/kg-treated group ($p<0.02$), and between the 10 mg/kg-treated group and the 40 mg/kg-treated group ($p<0.01$), as shown in FIG. 2.

Figure 2:
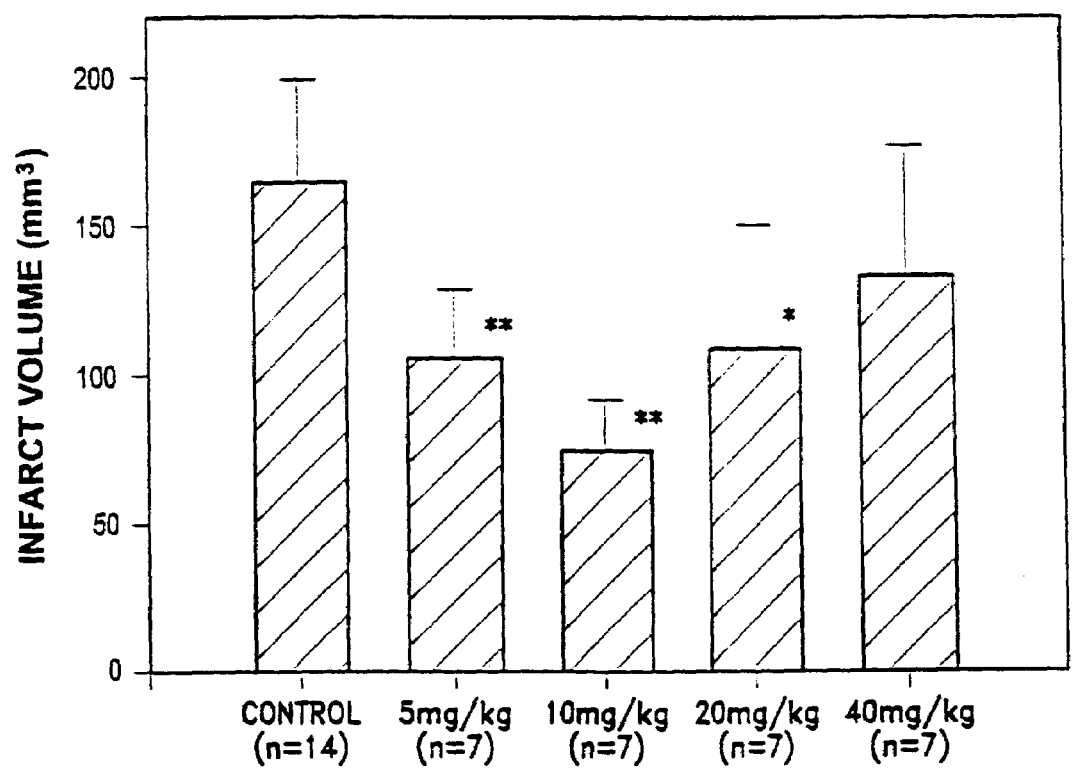
FIG. 2. Shows the effect of intraperitoneal administration of 3,4-dihydro-5-1-(1-piperidinyl)-butoxy]-1(2H)-isoquinolinone on the infarct volume.

In FIG. 2, the effect of intraperitoneal administration of 3,4-dihydro-5-[4-(1-piperidinyl)-butoxy]-1(2H)-isoquinolinone on the infarct volume was depicted graphically. The volumes of infarct were expressed as mean±standard deviation. Significant differences between the treated groups and the control group were indicated ($p<0.01$, $p<0.001$). It is not clear why a high dose (40 mg/kg) of the PARP inhibitor, 3,4-dihydro-5-[4-(1-piperidinyl)-butoxy]-1(2H)-isoquinolinone, was less neuroprotective. The U-shaped dose-response curve may suggest dual effects of the compound.

However, overall, the in vivo administration of the inhibitor led to a substantial reduction in infarct volume in the focal cerebral ischemia model in the rat. This result indicated that the activation of PARP plays an important role in the pathogenesis of brain damage in cerebral ischemia.

The values of arterial blood gases ($PaO_2$, $PaCO_2$ and pH) were within the physiological range in the control and treated groups with no significant differences in these parameters among the five groups, as shown below in Table III. A "steady state" MABP was taken following completion of the surgical preparation, just prior to occlusion, an "ischemia" MABP was taken as the average MABP during occlusion.

TABLE III

| | PaO$_2$ (mm Hg) | PaCO$_2$ (mm Hg) | pH | MABP (mm Hg) Steady State | Ischemia |
|---|---|---|---|---|---|
| Control group (n = 4) | 125 ± 21 | 38.6 ± 4.6 | 7.33 ± 0.05 | 79 ± 14 | 91 ± 13** |
| 5 mg/kg-treated group (n = 7) | 126 ± 20 | 38.0 ± 2.8 | 7.36 ± 0.02 | 78 ± 5 | 91 ± 12** |
| 10 mg/kg-treated group (n = 7) | 125 ± 16 | 39.3 ± 5.2 | 7.34 ± 0.03 | 80 ± 9 | 90 ± 14* |
| 20 mg/kg-treated group (n = 7) | 122 ± 14 | 41.3 ± 2.8 | 7.35 ± 0.23 | 79 ± 10 | 91 ± 12** |
| 40 mg/kg-treated group (n = 7) | 137 ± 17 | 39.5 ± 4.7 | 7.33 ± 0.24 | 78 ± 4 | 88 ± 12* |

*= Significantly different from the steady state value, $p < 0.05$.
**= Significantly different from the steady state value, $p < 0.01$.

There were no significant differences in any physiological parameter, including mean arterial blood pressure (MABP), prior to MCA and CCA occlusion among the five groups. Although MABP was significantly elevated following occlusion in all five groups, there were no significant differences in MABP during the occlusion period among the groups.

Since the blood flow values obtained from the laser doppler were in arbitrary units, only percent changes from the baseline (prior to occlusion) were reported. Right MCA and bilateral CCA occlusion produced a significant decrease in relative blood flow in the right parietal cortex to 20.8±7.7% of the baseline in the control group (n=5), 18.7±7.4% in the 5 mg/kg-treated group (n=7), 21.4±7.7% in the 10 mg/kg-treated group (n=7) and 19.3±11.2% in the 40 mg/kg-treated group (n=7). There were no significant differences in the blood flow response to occlusion among the four groups. In addition, blood flow showed no significant changes throughout the entire occlusion period in any group.

Following release of the carotid occlusions, a good recovery of blood flow (sometimes hyperemia) was observed in the right MCA territory of all animals. Reperfusion of the ischemic tissue resulted in the formation of NO and peroxnitrite, in addition to oxygen-derived free radicals. All of these radicals have been shown to cause DNA strand breaks and to activate PARP.

This example provided evidence that the related compounds of the present Invention are effective in inhibiing PARP activity.

Exemplified compounds of the present invention are tested for their ability to reduce focal cerebral ischemia in the following simplified procedure. Rats are allowed free access to water and rat chow (Wayne, Chicago, Ill.) until surgery. Housing and anesthesia concur with guidelines established by the institutional Animal Studies Committee, and are in accordance with the PHS Guide for the Care and Use of Laboratory Animals, USDA Regulations, and the AVMA Panel on Euthanasia guidelines.

The animals are anesthetized with isofluorane (induction, 3%; maintenance, 1.25% in a mixture of 30% O$_2$ and 70% NO$_2$ through a face mask. The rectal temperature is maintained at 37° C. with a homeothermic blanket (Harvard Apparatus, South Natick, Mass.). First, an iv catheter is inserted into the left femoral vein and the line run up through the nape of the neck for connection to a tethered swivel (Instech Laboratories, Plymouth Meeting, Pa.) and remote infusion pump (Stoelting Inc., Wood Dale, Ill.). In some cases, the right femoral artery is cannulated for monitoring arterial blood pressure and heart rate and for obtaining blood samples for arterial blood gas.

The right middle cerebral artery (MCA) is then exposed by making vertical skin incision midway between the right eye and ear and overlying skull is removed with a dental drill (Chen et al. 1986). After incision of the dura, the artery is coagulated at the level of the inferior cerebral vein with a bipolar cautery unit (Valleylab NS2000, Boulder, Colo.), and cut to prevent spontaneous reperfusion (Takahashi et al., 1997). Both common carotid arteries (CCAs) that had been previously isolated and freed of soft tissues and nerves are then ligated using non-traumatic ineurysm clips. After the wounds are closed with surgical clips, the animals are allowed to recover from anesthesia and returned to their cage which is warmed to 27° C. with a heated water underpad and humidified warm tent.

The PARP inhibitor to be tested is first administered 30 min after MCAO as an iv bolus, 10 mg/kg infused over 5 min, followed by a 12 hr continuous infusion of 2 mg/kg/hr (0.3 ml/hr). Ninety minutes after the MCAO, the animals are removed from the infusion tether, briefly reanesthetized with isofluorane, and the carotid clips are removed. The animal is returned to its warm cage and reconnected to the iv infusion pump for the duration of the experiment.

At 24 hrs after permanent MCAO, animals are sedated with ketamine and the heads removed by guillotine. Brains are removed, cooled in ice-cold saline, and sliced into 2 mm coronal sections using a rat brain matrice (Harvard Bioscience, South Natick, Mass.). The brain slices are incubated in phosphate-buffered saline (pH 7.4) containing 2% TTC at 37° C. for 10 min, and then stored in 10% neutral-buffered formalin. Cross-sectional area of the TTC-unstained region for each brain slice is determined using an image analyzer (MetaMorph, Universal Imaging Corp., West Chester. Pa.). The total volume of infarction in the right hemisphere is calculated by summation of the direct (TTC-negative) and indirect measures of the infarct areas in the component brain slices. The infarcted volumes in vehicle and drug-treated groups (n=8) are tested for significant statistical difference using an unpaired Student-t test.

Various doses of the compounds of the invention are tested in this model. The compounds are administered in either a single dose or a series of multiple doses, i.p, or i.v., at different times, both before or after the onset of ischemia. Compounds of the invention are expected to provide protection from ischemia in the range of about 0 to 80%.

Heart Ischemia/Reperfusion Injury

The experiments of the heart ischemia/reperfusion injury model is performed using female Sprague-Dawley rats weighing 250-300 g which are anesthetized with sodium pentobarbital at dose of 65 mg/kg intraperitoneally. The rectal temperature is maintained at 37° C. by using a homeothermic blanket system (Harvard Apparatus, South Natick, Mass.). The trachea is cannulated and the rat is ventilated with Room Air by using Harvard Rodent Ventilator (Harvard Apparatus, South Natick, Mass.). The left jugular vein is cannulated with PE-50 tubing for drug delivery. The right carotid artery is cannulated for BP measurement. The heart is exposed by opening the chest at the 4$^{th}$ left intercostal space. A main left branch of coronary artery (LAD) is occluded by 4-0 silk ligature for 30 min of ischemia and released for 90 min of reperfusion. During the experiment, arterial BP and EKG are monitored by Micro-Med Cardiovascular System (Louisville, Ky.).

At the end of reperfusion, the LAD coronary artery is re-occluded and about 2 ml of 5% Evans Blue dye is injected through i.v. line to distinguish the ischemic area from non-ischemic area of the heart. Then the heart is immediately taken off and frozen in the freezer. After at least 30 min of freezing, the heart is sliced into five sections with 2 mm thickness and stained in 1% TTC solution for 30 min at 37° C. The right ventricle is trimmed off. Infarct area, risk area and total left ventricular area in each face of the section are measured by using an image analysis system (BIOQUANT, Nashville, Tenn.). The infarct size is calculated as the percent total infarct volume of the total risk volume.

For drug treated group. Compounds are administered according to the following three protocols: 1. Single dose of compound is given 60 min prior to the onset of ischemia through i.p. injection. 2. Compound is delivered through i.v. bolus 1 min before the onset of ischemia followed by i.v. infusion until the end of reperfusion. 3. Compound is delivered through i.v. bolus 1 min before the onset of reperfusion followed by i.v. infusion until the end of reperfusion. For each drug-treated group, there is a corresponding vehicle treated group with n=6 or n=8. The difference between vehicle and drug treated groups is compared by using unpaired t-test with p<0.05. Various doses of compounds are tested in this model. The compounds are given in either single or multiple doses, i.p or i.v., at different times before or after the onset of ischemia. The compounds of this invention are expected to have ischemia/reperfusion injury protection in the range of 10 to 40 percent in this assay.

As a result of the PARP inhibition activity, the compounds of this invention are expected to protect against ischemia-induced degeneration of rat cortical neurons in vitro and thus may be useful in disorders arising from cerebral ischernia such as stroke, septic shock, or CNS degenerative disorders. They may also be useful in protecting the spinal cord following trauma. As an experimental result of ischemia/reperfusion injury in rats, the present invention is further directed to a method of prophylactic or therapeutic treatment of heart attack, cardiac arrest, cardiac bypass, diabetes, or risk of damage which comprises administering an effective amount of a compound of the present invention for PARP inhibition in unit dosage form.

In vitro Radiosensitization

In vitro radiosensitization may be measured with the use of a human prostate cancer cell line, PC-3s, which are plated in 6 well dishes and growin at monolayer cultures in RPMI1640 supplemented with 10% FCS. The cells are maintained at 37° C. in 5% $CO_2$ and 95% air. The cells are exposed to a dose response (0.1 mM to 0.1 µM) of 3 different PARP inhibitors prior to irradiation at one sublethal dose level. For all treatment groups, the six well plates are exposed at room temperature in a Seifert 250 kV/15 mA irradiator with a 0.5 mm Cu/1 mm. Cell viability is examined by exclusion of 0.4% trypan blue. Dye exclusion is assessed visually by microscopy and viable cell number was calculated by subtracting the number of cells from the viable cell number and dividing by the total number of cells. Cell proliferation rates are calculated by the amount of $^3$H-thymridine incorporation post-irradiation. The PARP inhibitors are expected to radiosensitize the cells.

Measuring kitered Gene Expression in mRNA Senescent Cells

Gene expression alteration may be measured with human fibroblast BJ cells which, at Population Doubling (PDL) 94. are plated in regular growth medium and then changed to low serum medium to reflect physiological conditions described in Linskens, et al., Nucleic Acids Res, 23:16: 3244-3251 (1995). A medium of DMEM/199 supplemented with 0.5% bovine calf serum is used. The cells are treated daily for 13 days. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West. Arch. Derm. 130:87-95 (1994). Elastin expression of the cells treated with the PARP inhibitor is expected to be significantly increased in comparison with the control cells. Elastin expression should be significantly higher in young cells compared to senescent cells, and thus treatment with the PARP inhibitor should cause elastin expression levels in senescent cells to change to levels similar to those found in much younger cells. Similarly, a beneficial effect should be seen in collagenase and collagen expression with treatment with the PARP inhibitors.

Measuring Altered Gene Expression of Protein in Senescent Cells

Gene expression alteration may be measured with approximately 105 BJ cells, at PDL 95-100 which are plated and grown in 15 cm dishes. The grouth medium is DMEM/199 supplemented with 10% bovice calf serum. The cells are treated daily for 24 hours with the PARP inhibitors of (100 µg/1 mL of medium) WO 99/11645. The cells are washed with phosphate buffered solution (PBS). then permeablized with 4% paraformaldehyde for 5 minutes, then washed with PBS, and treated with 100% cold methanol for 10 minutes. The methanol is removed and the cells are washed with PBS, and then treated with 10% serum to block nonspecific antibody binding. About 1 mL of the appropriate commercially available antibody solutions (1:500 dilution, Vector) is added to the cells and the mixture incubated for 1 hour. The cells are rinsed and washed three times with PBS. A secondary antibody, goat anti-mouse IgG (1 mL) with a biotin tag is added along with 1 mL of a solution containing streptavidin conjugated to alkaline phosphatase and 1 mL of NBT reagent (Vector). The cells are washed and changes in gene expression are noted colorimetrically. Four senescence-specific genes—collagen I, collagen III, collagenase, and interferon gamma—in senescent cells treated with the PARP inhibitor are monitored and the results should show a decrease in interferon gamma expression with no observable change in the expression levels of the other three gens, demonstrating that the PARP inhibitors can alter senescence-specific gene expression.

Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per $cm^2$ in 6-well tissue culture plates in DMEM/199 medium supplemented with 10% bovine calf serum and varying amounts (0.10 µM, and 1 mM; from a 100× stock solution in DMEM/M199 medium) of a PARP inhibitor. This process is repeated every 7 days until the cells appear to stop dividing. The untreated (control) cells reach senescence and stop dividing after about 40 days in culture. Treatment of cells with 10 µM 3-AB appears to have little or no effect in contrast to treatment with 100 µM 3-AB which appears lengthen the lifespan of the cells and treatment with 1 mM 3-AB which dramatically increases the lifespan and proliferative capacity of the cells. The cells treated with 1 mM 3-AB will still divide after 60 days in culture.

Neuroprotective Effects of PARP Inhibitors on Chronic Constriction Injury (CCI) in Rats Adult male Sprague-Dawley rats, 300-350 g, are anesthetized with intraperitoneal 50 mg/kg sodium pentobarbital. Nerve ligation is performed by exposing one side of the rat's sciatic nerves and dissecting a 5-7 mm-long nerve segment and closing with four loose ligatures at a 1.0-1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-wiithdrawal latency is defined as the time elapsed from the onset of radiant heat stimulation to withdrawal of the rat's hindpaw.

Mechanical hyperalgesia is assessed by placing the rat in a cage with a bottom made of perforated metal sheet with many small square holes. Duration of paw-withdrawal is recorded after pricking the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I-II, of rats 8 days after unilateral sciatic nerve ligation as compared with sham operated rats. Various doses of PARP inhibitors are tested in this model and shown to reduce both incidence of dark neurons and neuropathic pain behavior in CCI rats.

The invention being thus described, it will be obvious that the same may be varied in many ways. Such variations are not to be regarded as a departure from the spirit and scope of the invention, and all such modifications are intended to be included within the scope of the following claims. All references cited herein are incorporated in their entirety by reference herein.

We claim:
1. A compound of Formula I:

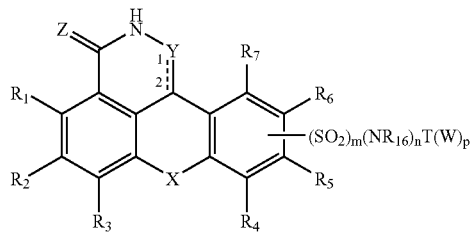

(I)

or a pharmaceutically acceptable salt, hyydrate, or mixtures thereof, wherein:
m is zero or one;
n is zero or one;
p is one or two;

Y is a direct bond, $-N(R_{10})-$, or $N_i$;
Z is O, or S;
X is $NR_{11}$, $-O-$, $-S-$, $CR_{12}R_{13}-$, a bond, $-CR_{12}=CR_{13}-$, or $-C(R_{12}R_{13})C(R_{14}R_{15})-$;
W is selected from $-CN$, $-(N(R_9)_2)$ where the $R_9$ substituents may be combined to form a heteroaryl or cycloaukyl optionally containing at least one hetero atom, $-P(O)_2-OR_9$, $-P(O)(OR_9)_2$, $-S(O)_2-R_9$, $-S(O)_3R_9$, $-C(O)-R_9$, $-C(O)-N(R_9)_2$, $-S(O)_2NR_9$, cycloalkyl optionally containing at least one heteroatom, and heteroaryl;
$R_1$, $R_2$, $R_3$, $R_4$, $R_5$, $R_6$, $R_7$, $R_8$, $R_{12}$, $R_{13}$, $R_{14}$, and $R_{15}$ and $R_{15}$ are independently: hydrogen, lower alkyl, cycloalkyl optionally containing at least one heteroatonil lower alkenyl, lower alkoxy, aryl, heteroaryl, aralkyl, heteroaralkyl, alkaryl, alkheteroaryl, hydroxy, amino, nitro, halo, nitroso, sulfo, sulfonic acid or carboxy;
each $R_9$ is independently: hydrogen, lower alkyl, cycloalkyl optionally containing at least one heteroatom, lower alkenyl, aryl, heteroaryl, aralkyl, heteroaralkyl, alkaryl, hydroxy, hydroxy-lower alkyl, alkoxy, amino, or carboxy;
$R_{10}$ and $R_{11}$ are independently: hydrogen, lower alkyl, lower alkenyl, aryl, aralkyl, alkaryl, halo, hydroxy, alkoxy, amino, or carboxy;
each $R_{16}$ is independently hydrogen or lower alkyl; and
T a divalent or trivalent organic radical independently selected from the group consisting of: lower alkylene, lower alkenylene, arylene, aralkylene, and alkarylene;
wherein one, two or three of the hydrogen atoms of said divalent or trivalent organic radical can be substituted by a moiety selected from the group consisting of: lower ($C_1$-$C_9$ straight or branched chain) alkyl, cycloalkyl, lower ($C_2$-$C_9$ straight or branched chain) alkenyl, cycloalkenyl, aryl, heteroaryl, aralkyl, heteroarylalkyl, alkaryl, alkheteroaryl, halo, trifluoromethyl, hydroxy, lower ($C_1$-$C_4$) alkoxy, amino, nitro, trifluoromethyl, alkenyloxy, phenoxy, and benzyloxy;
wherein one, two, or three carbon atoms in the divalent or trivalent organic radical can be replaced by a heteroatom-containing-moiety selected from the group consisting of: phenoxy, phenoxymethyl, phenoxycarbonyl, benzyloxy, $-O-$, $>C=O$, $-S-$, $-SO_2-$, $-NR_1SO_2-$, $-SO_2NR_1-$, $-NR_1-$, and $-PO_2-$;
wherein any of the lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, and alkaryl aroups can be independently substituted with one, two or three substituents selected from the group consisting of: lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, cycloalkenyl, aryl, heteroaryl, aralkyl, heteroaralkyl, alkaryl, alkheteroaryl, halo, trifluoromethyl, hydroxy, lower ($C_1$-$C_4$) alkoxy, carboxy, carbonyl, lower alkyl ester, amino, nitro, trifluoromethyl, alkenyloxy, phenoxy, benzyloxy,
wherein one, two, or three carbon atoms of any of the lower ($C_1$-$C_9$ straight or branched chain) alkyl, $C_3$-$C_8$ cycloalkyl optionally containing at least one heteroatom in place of a carbon atom, lower ($C_2$-$C_9$ straight or branched chain) alkenyl, aryl, heteroaryl, aralkyl, and alkaryl groups can be replaced by a hetero-atomcontaining-moiety selected from the group consisting of: —O—, >C=O, —S—, —SO$_2$—, —NR$_1$SO$_2$—, —SO$_2$NR$_1$—, N, —NR$_1$—, and —PO$_2$—.

2. A compound of claim 1 wherein m and n are zero, p is one, W is —CN and R$_1$-R$_7$ are hydrogen.

3. A compound of claim 1, wherein m and n are zero, p is one, W is —CN, T is —CH$_2$—, Z and X are oxygen, Y is N and R$_1$ to R$_7$ are hydrogen.

4. A compound of claim 1, wherein wherein p is one and W is —(N(R$_9$)$_2$).

5. A compound of claim 1 wherein p is one and W is selected from the group consisting of —P(O)$_2$—OR$_9$ and —P(O)(OR$_9$)$_2$.

6. A compound of claim 1 wherein p is one and W is selected from the group consisting of —S(O)$_2$—R$_9$, —S(O)$_2$OR$_9$ and —S(O)$_2$NR$_9$.

7. A compound of claim 1 wherein p is one and W is —C(O)R$_9$ or —C(O)N(R$_9$)$_2$.

8. A compound of claim 1 wherein p is one and W is a heteroaryl or a cycloalkyl optionally containing at least one heteroatom.

9. A compound of Formula (II)

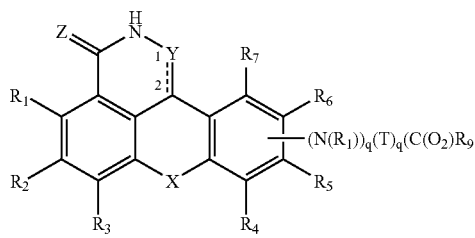

(II)

or a pharmaceutically acceptable salt hydrate, or mixtures thereof, wherein:
q is one;
Y is N;
Z is O;
X is —O—, or a bond;
R$_1$, R$_2$, R$_3$, R$_4$, R$_5$, R$_6$, and R$_7$ are independently: hydrogen, lower alkyl, lower alkenyl, cyloalkyl optionally containing at least one heteroatom, lower alkoxy, aryl, heteroaryl, aralkyl, heteroaralkyl, alkaryl, alkheteroarly, hydroxy, amino, nitro, halo, nitroso, or carboxy;
R$_9$ is hydrogen, lower alkyl, cycloalkyl optionally containing at least one heteroatom, lower alkenyl, aryl, heteroaryl, aralkyl, heteroaraklyl, alkaryl, alkheteroaryl, hydroxy, alkoxy, amino, or carboxy; and
T, is a divalent or trivalent organic radical independently selected from the group consisting of: lower alkylene, lower alkenylene, arylene, aralkylene, and alkarylene, wherein one, two or three of the hydrogen atoms of said divalent or trivalent organic radical can be substituted by a moiety selected from the group consisting of: lower alkyl, lower alkenyl, aryl, aralkyl, alkaryl, halo, trifluoromethyl, hydroxy, alkoxy, amino, nitro, trifluoromethyl, alkenyloxy, phenoxy, and benzyloxy;
wherein one, two, or three carbon atoms in the divalent or trivalent organic radical can be replaced by a heteroatom-containing-moiety selected from the group consisting of: penoxy, phenoxycarbonyl, benzyloxy, —O—, >C=O, —S—, —SO$_2$—, —NR$_1$SO$_2$—, —SO$_2$NR$_1$—, —NR$_1$—, and —PO$_2$—;
wherein the lower alkyl, cyloalkyl optionally containing at least one heteroatom, lower alkenyl, aryl, heteroaryl, aralkyl, heteroalkyl, alkaryl, and alkheteroaryl groups can be independently substituted with one, two or three substituents selected from the group consisting of: lower alkyl, cycolalkyl optionally containing at least one heteroatom, lower alkenyl, aryl, heteroaryl, aralkyl, heteroarakyl, alkaryl, alkheteroaryl, halo, trifluoromethyl, hydroxy, alkoxy, carboxy, carbonyl, lower alkyl ester, amino, nitro, trifluoromethyl, alkenyloxy, phenoxy, benzyloxy,
wherein one, two, or three carbon atoms of the one, two or three substituents selected from the group consisting of: lower alkyl, cycolalkyl optionally containing at least one heteroatom, lower alkenyl, aryl, heteroaryl, aralkyl, heteroaralkyl, alkaryl, alkheteroaryl, halo, trifluoromethyl, hydroxy, alkoxy, carboxy, carbonyl, lower alkyl ester, amino, nitro, trifluoromethyl, alkenyloxy, phenoxy, benzyloxy can be replaced by a heteroatom-containing-moiety selected from the group consisting of: —O—, >C=O, —S—, —SO$_2$—, —NR$_1$SO$_2$—, —SO$_2$NR$_1$—, —NR$_1$—, —NR$_1$—, and —PO$_2$—.

10. A compound according to Formula (III)

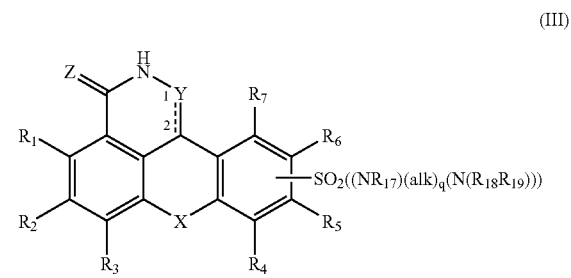

(III)

wherein
Z and X are oxygen;
Y is N;
q is zero or one;
"alk" is lower alkylene;
R$_{17}$, R$_{18}$ and R$_{19}$ are independently hydrogen or lower alkyl; or
R$_{17}$ and R$_{18}$ or R$_{18}$ and R$_{19}$ taken together can be a lower alkylene to form a heterocyclic ring; and
R$_1$, R$_2$, R$_3$, R$_4$, R$_5$, R$_6$, and R$_7$ are independently: hydrogen, lower alkyl, cycloalkyl optionally containing at least one hetero atom, lower alkenyl, lower alkoxy, aryl, heteroaryl, aralkyl, heteroaralkyl, alkaryl, alkheteroaryl, hydroxy, amino, nitro, halo, nitroso, or carboxy.

11. A pharmaceutical composition which comprises; (i) a therapeutically effective amount of a compound according to claim 1 and (ii) a pharmaceutically acceptable carrier.

12. The pharmaceutical composition of claim 11, wherein the carrier is a sterile solution, suspension or emulsion, in a single or divided dose.

13. The pharmaceutical composition of claim 11, wherein the carrier is a capsule or tablet containing a single or divided dose of said compound.

14. The pharmaceutical composition of claim 11, wherein the carrier comprises a biodegradable polymer.

15. The pharmaceutical composition of claim 14, wherein the biodegradable polymer releases the compound of formula I over a prolonged period of time.

16. The pharmaceutical composition of claim 11, wherein the carrier is a solid implant.

17. A method of inhibiting PARP activity, thereby treating neural tissue damage resulting from ischemia and reperfusion injury, or radiosensitizing, comprising: administering a therapeutically effective amount of a compound of claim 1.

18. The method of claim 17, wherein the compound is administered as a sterile solution, suspension or emulsion, in a single or divided dose.

19. The method of claim 17, wherein the compound is administered as a capsule or tablet containing a single or divided dose of said compound.

20. The method of claim 17, wherein the compound is administered with a biodegradable polymer.

21. The method of claim 20, wherein the biodegradable polymer releases the compound of formula I over a prolonged period of time.

22. The method of claim 17, wherein the compound is administered with a solid implant.

23. A method of treating cardiac tissue damage resulting from ischemia and reperfusion injury comprising administering a therapeutically effective amount of a compound of claim 1.

* * * * *